US010669596B2

(12) United States Patent
Mohamed et al.

(10) Patent No.: US 10,669,596 B2
(45) Date of Patent: Jun. 2, 2020

(54) METHODS FOR INDUCING CELL DIVISION OF POSTMITOTIC CELLS

(71) Applicant: The J. David Gladstone Institutes, A Testamentary Trust Established under the Will of J. David Gladstone, San Francisco, CA (US)

(72) Inventors: Tamer M. A. Mohamed, San Francisco, CA (US); Deepak Srivastava, San Francisco, CA (US)

(73) Assignee: The J. David Gladstone Institutes, a testamentary trust established under the Will of J. David Gladstone, San Francisco, CA (US)

( * ) Notice: Subject to any disclaimer, the term of this patent is extended or adjusted under 35 U.S.C. 154(b) by 5 days.

(21) Appl. No.: 15/564,752

(22) PCT Filed: Apr. 5, 2016

(86) PCT No.: PCT/US2016/026059

§ 371 (c)(1),
(2) Date: Oct. 6, 2017

(87) PCT Pub. No.: WO2016/164371

PCT Pub. Date: Oct. 13, 2016

(65) Prior Publication Data

US 2018/0112282 A1 Apr. 26, 2018

Related U.S. Application Data

(60) Provisional application No. 62/151,321, filed on Apr. 22, 2015, provisional application No. 62/144,244, filed on Apr. 7, 2015.

(51) Int. Cl.

| | |
|---|---|
| ***A61K 38/45*** | (2006.01) |
| ***A61K 35/39*** | (2015.01) |
| ***A61K 38/17*** | (2006.01) |
| ***A61P 9/10*** | (2006.01) |
| ***A61K 35/30*** | (2015.01) |
| ***A61K 35/34*** | (2015.01) |
| ***A61K 35/36*** | (2015.01) |
| *A61K 35/00* | (2006.01) |

(52) U.S. Cl.

CPC ...... *C12Y 207/11022* (2013.01); *A61K 35/30* (2013.01); *A61K 35/34* (2013.01); *A61K 35/36* (2013.01); *A61K 35/39* (2013.01); *A61K 38/1709* (2013.01); *A61K 38/45* (2013.01); *A61P 9/10* (2018.01); *A61K 35/00* (2013.01); *A61K 2300/00* (2013.01); *C12N 2310/111* (2013.01)

(58) Field of Classification Search

CPC ............ A61K 2300/00; A61K 38/1709; A61K 38/45; A61K 35/00; A61K 35/30; A61K 35/34; A61K 35/36; A61K 35/39; A61P 9/10; C12N 2310/111; C12Y 207/11022

See application file for complete search history.

(56) References Cited

U.S. PATENT DOCUMENTS

| | | | |
|---|---|---|---|
| 5,449,614 A | 9/1995 | Danos et al. | |
| 5,591,624 A | 1/1997 | Barber et al. | |
| 5,817,491 A | 10/1998 | Yee et al. | |
| 5,834,256 A | 11/1998 | Finer et al. | |
| 6,040,174 A | 3/2000 | Imler et al. | |
| 6,333,195 B1 | 12/2001 | Respess et al. | |
| 6,440,944 B2 | 8/2002 | Bruder et al. | |
| 6,872,528 B2 | 3/2005 | Klatzmann et al. | |
| 6,910,434 B2 | 6/2005 | Lundgren | |
| 6,995,009 B1 | 2/2006 | Kitamura et al. | |
| 7,070,994 B2 | 7/2006 | Barber et al. | |
| 7,078,387 B1 | 7/2006 | Leiden et al. | |
| 7,645,734 B2 | 1/2010 | Chaudhry et al. | |
| 8,217,157 B2 | 7/2012 | Chaudhry et al. | |
| 8,633,024 B2 | 1/2014 | D'Amour et al. | |
| 9,132,167 B2 | 9/2015 | Chaudhry et al. | |
| 9,220,721 B2 | 12/2015 | Aguirre et al. | |
| 2003/0060397 A1 | 3/2003 | Timsit et al. | |
| 2004/0038397 A1 | 2/2004 | Smith et al. | |
| 2004/0106647 A1 | 6/2004 | Schneider et al. | |
| 2007/0009496 A1* | 1/2007 | Adachi ............. | A61K 31/7088 424/93.21 |
| 2012/0121557 A1 | 5/2012 | Kuhn | |
| 2014/0021994 A1 | 1/2014 | Tanaka et al. | |

FOREIGN PATENT DOCUMENTS

| | | |
|---|---|---|
| JP | 2011021023 | 2/2011 |
| WO | WO 93/03769 | 3/1993 |
| WO | WO 93/09239 | 5/1993 |
| WO | WO 93/19191 | 9/1993 |
| WO | WO 94/12649 | 6/1994 |
| WO | WO 94/28938 | 12/1994 |
| WO | WO 95/00655 | 1/1995 |
| WO | WO 95/11984 | 5/1995 |
| WO | WO 00/78119 | 12/2000 |
| WO | 02095026 | 11/2002 |
| WO | WO 2005/000403 | 1/2005 |
| WO | 2005049822 | 6/2005 |

OTHER PUBLICATIONS

Li et al. Brain Research (1997) 765: 301-312 (Year: 1997).*
Yamamoto et al. (Eur. J. Pharmaceutics Biopharmaceutics (2009) 71: 484-489 (Year: 2009).*
Sanatamaria et al. Nature (2007) 448: 811-815 (Year: 2007).*
Bellanger et al. Oncogene (2007) 26: 7175-7184 (Year: 2007).*
"PIRES2-EGFP Vector Information," BD Biosciences Clontech. Retrieved from the internet on Jul. 6, 2016: <http://www.dmlim.net/vectors/pIRES2-EGFP/pIRES2-EGFp-map.pdf> (Oct. 3, 2002).

(Continued)

*Primary Examiner* — Susan M Hanley
(74) *Attorney, Agent, or Firm* — Schwegman Lundberg & Woessner, P.A.

(57) ABSTRACT

The present disclosure provides methods for inducing cell cycle reentry of postmitotic cell. The present disclosure further provides cells and compositions for treating diseases, such as cardiovascular diseases, neural disorders, hearing loss, and diabetes.

9 Claims, 16 Drawing Sheets

Specification includes a Sequence Listing.

(56) References Cited

OTHER PUBLICATIONS

Aguirre, A. et al. In vivo activation of a conserved microRNA program induces mammalian heart regeneration. Cell Stem Cell 15, 589-604, doi:10.1016/j.stem.2014.10.003 (2014).
Aguirre, A., Sancho-Martinez, I. & Izpisua Belmonte, J. C. Reprogramming toward heart regeneration: stem cells and beyond. Cell Stem Cell 12, 275-284, doi:10.1016/j.stem.2013.02.008 (2013).
Ahuja et al. "Cardiac myocyte cell cycle control in development, disease, and regeneration," Physiol Rev 87:521-544 (Apr. 2007).
Ali, S. R. et al. Existing cardiomyocytes generate cardiomyocytes at a low rate after birth in mice. Proc Natl Acad Sci U S A 111, 8850-8855, doi:10.1073/pnas.1408233111 (2014).
Ang, Y. S. et al. Disease Model of GATA4 Mutation Reveals Transcription Factor Cooperativity in Human Cardiogenesis. Cell 167, 1734-1749 e1722, doi:10.1016/j.cell.2016.11.033 (2016).
Arrasate, M. et al. "Automated microscope system for determining factors that predict neuronal fate," Proc Natl Acad Sci USA 102(10):3840-3845 (2005).
Artegiani et al., "Overexpression of cdk4 and cyclinD1 triggers greater expansion of neural stem cells in the adult mouse brain," J Exp Med. 208:937-48 (Apr. 11, 2011).
Bassermann, F., Eichner, R. & Pagano, M. The ubiquitin proteasome system—implications for cell cycle control and the targeted treatment of cancer. Biochim Biophys Acta 1843, 150-162, doi:10.1016/j.bbamcr.2013.02.028 (2014).
Bersell, K., Arab, S., Haring, B. & Kuhn, B. Neuregulin1/ErbB4 signaling induces cardiomyocyte proliferation and repair of heart injury. Cell 138, 257-270, doi:10.1016/j.cell.2009.04.060 (2009).
Bicknell, K. A., Coxon, C. H. & Brooks, G. Forced expression of the cyclin B1-CDC2 complex induces proliferation in adult rat cardiomyocytes. Biochem J 382, 411-416, doi:10.1042/BJ20031481 (2004).
Chaudhry, H. W. et al. Cyclin A2 mediates cardiomyocyte mitosis in the postmitotic myocardium. J Biol Chem 279, 35858-35866, doi:10.1074/jbc.M404975200 (2004).
Clardy, Susan M. et al. "Rapid, high efficiency isolation of pancreatic β-cells," Scientific Reports 5(13681):1-9 (Sep. 2, 2015).
D'Amour et al. "Efficient differentiation of human embryonic stem cells to definitive endoderm," Nature Biotech. 23:1534-1541 (Dec. 2005).
Eulalio, A. et al. Functional screening identifies miRNAs inducing cardiac regeneration. Nature 492, 376-381, doi:10.1038/nature11739 (2012).
Fededa, J. P. & Gerlich, D. W. Molecular control of animal cell cytokinesis. Nat Cell Biol 14, 440-447, doi:10.1038/ncb2482 (2012).
Fu et al. "Roles of Aurora kinases in mitosis and tumorigenesis," Mol Cancer Res 5(1):1-10 (Jan. 2007).
Fujimitsu, K., Grimaldi, M. & Yamano, H. Cyclin-dependent kinase 1-dependent activation of APC/C ubiquitin ligase. Science 352, 1121-1124, doi:10.1126/science.aad3925 (2016).
Galderisi et al. "Cell cycle regulation and neural differentiation," Oncogene 22(33): 5208-5219 (Aug. 2003).
Gemberling, M., Karra, R., Dickson, A. L. & Poss, K. D. Nrg1 is an injury-induced cardiomyocyte mitogen for the endogenous heart regeneration program in zebrafish. Elife 4, doi:10.7554/eLife.05871 (2015).
Guo et al. "In vivo direct reprogramming of reactive glial cells into functional neurons after brain injury and in an Alzheimer's disease model," Cell Stem Cell 14(2):188-202 (Feb. 6, 2014).
Heallen, T. et al. Hippo pathway inhibits Wnt signaling to restrain cardiomyocyte proliferation and heart size. Science 332, 458-461, doi:10.1126/science.1199010 (2011).
Huang, Y. et al. Igf Signaling is Required for Cardiomyocyte Proliferation during Zebrafish Heart Development and Regeneration. PloS one 8, e67266, doi:10.1371/journal.pone.0067266 (2013).
Hydbring, P., Malumbres, M. & Sicinski, P. Non-canonical functions of cell cycle cyclins and cyclin dependent kinases. Nat Rev Mol Cell Biol 17, 280-292, doi:10.1038/nrm.2016.27 (2016).
Ieda M. et al. Cardiac fibroblasts regulate myocardial proliferation through beta1 integrin signaling. Dev Cell 16, 233-244, doi:10.1016/j.devcel.2008.12.007 (2009).
Ieda M. et al. Direct reprogramming of fibroblasts into functional cardiomyocytes by defined factors. Cell 142, 375-386 (2010).
International Search Report and Written Opinion dated Aug. 15, 2016 for International Application No. PCT/US2016/026059.
Jopling, C. et al. Zebrafish heart regeneration occurs by cardiomyocyte dedifferentiation and proliferation. Nature 464, 606-609, doi:10.1038/nature08899 (2010).
Keirstead et al. "Human Embryonic Stem Cell-Derived Oligodendrocyte Progenitor Cell Transplants Remyelinate and Restore Locomotion after Spinal Cord Injury," J. Neurosci. 25(19):4694-4705 (May 11, 2005).
Kikuchi, K. et al. Primary contribution to zebrafish heart regeneration by gata4(+) cardiomyocytes. Nature 464, 601-605, doi:10.1038/nature08804 (2010).
Kim et al. Direct lineage reprogramming to neural cells, Curr Opinion Neurobiol. 22(5):778-784 (Oct. 2012).
Kwon C. et al. "Canonical Wnt signaling is a positive regulator of mammalian cardiac progenitors," Proc. Natl. Acad. Sci. 104(26):10894-10899 (Jun. 26, 2007).
Lestuzzi, C. Primary tumors of the heart. Curr Opin Cardiol 31, 593-598, . doi:10.1097/HCO.0000000000000335 (2016).
Li, P. et al. IGF signaling directs ventricular cardiomyocyte proliferation during embryonic heart development. Development 138, 1795-1805, doi:10.1242/dev.054338 (2011).
Li, V. C. & Kirschner, M. W. Molecular ties between the cell cycle and differentiation in embryonic stem cells. Proc Natl Acad Sci U S A 111, 9503-9508, doi:10.1073/pnas.1408638111 (2014).
Lian, X. et al. "Directed cardiomyocyte differentiation from human pluripotent stem cells by modulating Wnt/β-catenin signaling under fully defined conditions," Nat Protoc 8(1): 162-175 (2013).
Malumbres, M. & Barbacid, M. Cell cycle, CDKs and cancer: a changing paradigm. Nat Rev Cancer 9, 153-166, doi:10.1038/nrc2602 (2009).
Mohamed et al., "The tumour suppressor Ras-association domain family protein 1A (RASSF1A) regulates TNF-α signaling in cardiomyocytes," Cardiovasc Res. 1;103(1):47-59 (Jul. 2014).
Mohamed, T. M. et al. The plasma membrane calcium ATPase 4 signalling in cardiac fibroblasts mediates cardiomyocyte hypertrophy. Nat Commun 7, 11074, doi:10.1038/ncomms11074 (2016).
Morikawa, Y. et al. Actin cytoskeletal remodeling with protrusion formation is essential for heart regeneration in Hippo-deficient mice. Sci Signal 8, ra41, doi:10.1126/scisignal.2005781 (2015).
Ovejero-Benito et al., "Brain-derived neurotrophic factor-dependent cdk1 inhibition prevents G2/M progression in differentiating tetraploid neurons," PLoS One. 8:1-13 (May 31, 2013).
Perry, J. A. & Kornbluth, S. Cdc25 and Wee1: analogous opposites? Cell Div 2, 12, doi:10.1186/1747-1028-2-12 (2007).
Polizzotti, B. D. et al. Neuregulin stimulation of cardiomyocyte regeneration in mice and human myocardium reveals a therapeutic window. Sci Transl Med 7, 281ra245, doi:10.1126/scitranslmed.aaa5171 (2015).
Porrello, E. R. et al. Transient regenerative potential of the neonatal mouse heart. Science 331, 1078-1080, doi:10.1126/science.1200708 (2011).
Puente, B. N. et al. The oxygen-rich postnatal environment induces cardiomyocyte cell-cycle arrest through DNA damage response. Cell 157, 565-579, doi:10.1016/j.cell.2014.03.032 (2014).
Qian et al., "In vivo reprogramming of murine cardiac fibroblasts into induced cardiomyocytes," Nature 485(7400):593-8 (May 31, 2012).
Ravitz, M. J., Yan, S., Dolce, C., Kinniburgh, A. J. & Wenner, C. E. Differential regulation of p27 and cyclin D1 by TGF-beta and EGF in C3H 10T1/2 mouse fibroblasts. J Cell Physiol 168, 510-520, doi:10.1002/(SICI)1097-4652(199609)168:3<510::AID-JCP3>3.0.CO;2-S (1996).
Ronaghi et al. "Inner ear hair cell-like cells from human embryonic stem cells," Stem Cells and Dev. 23(11):1275-1284 (Mar. 10, 2014).
Rubart, M. & Field, L. J. Cardiac regeneration: repopulating the heart. Annu Rev Physiol 68, 29-49, doi:10.1146/annurev.physiol.68.040104.124530 (2006).

(56) References Cited

OTHER PUBLICATIONS

Salani et al. "Generation of skeletal muscle cells from embryonic and induced pluripotent stem cells as an in vitro model and for therapy of muscular dystrophies," J Cell Mol. Med. 16(7):1353-1364 (Jul. 2012).
Saxena et al. "Stromel cell-derived factor-1alpha is cardioprotective after myocardial infarction," Circulation 117: 2224-2231 (Apr. 21, 2008).
Senyo et al. "Cardiac regeneration based on mechanisms of cardiomyocyte proliferation and differentiation," Stem Cell Research 13,532-541 (Nov. 2014).
Shapiro, S. D. et al. Cyclin A2 induces cardiac regeneration after myocardial infarction through cytokinesis of adult cardiomyocytes. Sci Transl Med 6, 224ra227, doi:10.1126/scitranslmed.3007668 (2014).
Takeuchi, T. Regulation of cardiomyocyte proliferation during development and regeneration. Dev Growth Differ 56, 402-409, doi:10.1111/dgd.12134 (2014).
Tamamori-Adachi, M. et al. Cardiomyocyte proliferation and protection against post-myocardial infarction heart failure by cyclin D1 and Skp2 ubiquitin ligase. Cardiovasc Res 80, 181-190, doi:10.1093/cvr/cvn183 (2008).
Tian, Y. et al. A microRNA-Hippo pathway that promotes cardiomyocyte proliferation and cardiac regeneration in mice. Sci Transl Med 7, 279ra238, doi:10.1126/scitranslmed.3010841 (2015).
Vakifahmetoglu, H., Olsson, M. & Zhivotovsky, B. Death through a tragedy: mitotic catastrophe. Cell Death Differ 15, 1153-1162, doi:10.1038/cdd.2008.47 (2008).
Wang et al., "Systemic delivery of modified mRNA encoding herpes simplex virus 1 thymidine kinase for targeted cancer gene theraphy," Mol Ther. 21:358-67 (Dec. 11, 2012).
Xin, M. et al. Hippo pathway effector Yap promotes cardiac regeneration. Proc Natl Acad Sci USA 110, 13839-13844, doi:10.1073/pnas.1313192110 (2013).
Yin, V. P. & Poss, K. D. New regulators of vertebrate appendage regeneration. Current opinion in genetics & development 18, 381-386, doi:10.1016/j.gde.2008.06.008 (2008).
Zangi, L. et al. Modified mRNA directs the fate of heart progenitor cells and induces vascular regeneration after myocardial infarction. Nature biotechnology 31, 898-907, doi:10.1038/nbt.2682 (2013).
Zebrowski, D. C., Becker, R. & Engel, F. B. Towards regenerating the mammalian heart: challenges in evaluating experimentally induced adult mammalian cardiomyocyte proliferation. American journal of physiology 310, H1045-1054, doi:10.1152/ajpheart.00697.2015 (2016).
Zong, H., Espinosa, J. S., Su, H. H., Muzumdar, M. D. & Luo, L. Mosaic analysis with double markers in mice. Cell 121, 479-492, doi:10.1016/j.cell.2005.02.012 (2005).
Ali et al., "Adeno-Associated Virus Gene Transfer to Mouse Retina," Hum Gene Ther 9(1):81-86, (publication date: Jan. 1, 1998).
Ali et al., "Gene transfer into the mouse retina mediated by an adeno-associated viral vector," Hum Mol Genet. 5(5):591-594 (publication date: May 1996).
Arrasate et al., "Automated microscope system for determining factors that predict neuronal fate," Proc Natl Acad Sci USA 102(10):3840-3845 (publication date: Mar. 8, 2005, epublication date: Feb. 28, 2005).
Bennett et al., "Real-Time, Noninvasive In Vivo Assessment of Adeno-Associated Virus-Mediated Retinal Transduction," Invest Opthalmol Vis Sci 38(13):2857-2863 (publication date: Dec. 1997).
Bevis et al., "Rapidly maturing variants of the Discosoma red fluorescent protein (DsRed)," Nat. Biotechnol. 20(1):83-87 (publication date: Jan. 2002).
Bitter et al., "Expression and Secretion Vectors for Yeast," Methods in Enzymology, 153:516-544 (1987).
Borrás et al., "Adenoviral reporter gene transfer to the human trabecular meshwork does not alter aqueous humor outflow. Relevance for potential gene therapy of glaucoma," Gene Ther 6(4):515-524 (publication date: Apr. 1999).
Choi et al., "Establishment of Isolation and Expansion Protocols for Human Cardiac C-kit-Positive Progenitor Cells for Stem Cell Therapy," Transplantation Proceedings 45(1):420-426 (publication date: Jan.-Feb. 2013).
Clardy et al., "Rapid, high efficiency isolation of pancreatic β-cells," Scientific Reports 5:13681 (publication date: Sep. 2, 2015).
D'Amour et al., "Efficient differentiation of human embryonic stem cells to definitive endoderm," (2005) Nature Biotech. 23(12):1534-1541 (publication date: Dec. 2005, epublication date: Oct. 28, 2005).
Extended European Search Report dated Nov. 11, 2018 for European Application No. 16777144.3.
Felgner et al., "Lipofection: A highly efficient, lipid-mediated DNA-transfection procedure," Proc. Natl. Acad. Sci. 84(21):7413-7417 (publication date: Nov. 1, 1987).
Flannery et al., "Efficient photoreceptor-targeted gene expression in vivo by recombinant adeno-associated virus," Proc. Natl. Acad. Sci. 94(13):6916-6921 (publication date: Jun. 24, 1997).
Flotte et al., Stable in vivo expression of the cystic fibrosis transmembrane conductance regulator with an adeno-associated virus vector, Proc. Natl. Acad. Sci. 90:10613-10617 (publication date: Nov. 1993).
Franz et al., "Analysis of tissue-specific gene delivery by recombinant adenoviruses containing cardiac-specific promoters," Cardiovasc. Res. 35(3):560-566 (publication date: Sep. 1997).
Fu et al., "Roles of Aurora Kinases in Mitosis and Tumorigenesis," Mol Cancer Res 5(1):1-10 (publication date: Jan. 2007).
Galderisi et al., "Cell cycle regulation and neural differentiation," Oncogene 22(33): 5208-5219 (publication date: Aug. 11, 2003).
Gérard et al., "From quiescence to proliferation: Cdk oscillations drive the mammalian cell cycle," Frontiers in Physiol. 3(413):1-18 (publication date: Nov. 2, 2012).
Guo et al., "In Vivo Direct Reprogramming of Reactive Glial Cells into Functional Neurons after Brain Injury and in an Alzheimer's Disease Model," Cell Stem Cell 14(2):188-202 (publication date: Feb. 6, 2014, epublication date: Dec. 19, 2013).
Hunter et al., "Targeting Gene Expression to Specific Cardiovascular Cell Types in Transgenic Mice," Hypertension 22:608-617 (publication date: Oct. 1, 1993).
Ieda et al., "Cardiac Fibroblasts Regulate Myocardial Proliferation through β1 Integrin Signaling," Dev. Cell 16(2): 233-244 (publication date: Feb. 17, 2009).
Ieda et al., "Direct Reprogramming of Fibroblasts into Functional Cardiomyocytes," Cell 142(3):375-386 (publication date: Aug. 6, 2010).
Johnston et al., "Minimum Requirements for Efficient Transduction of Dividing and Nondividing Cells by Feline Immunodeficiency Virus Vectors," Journal of Virology, 73(6):4991-5000 (publication date: Jun. 1999).
Jomary et al., "Rescue of photoreceptor function by AAV-mediated gene transfer in a mouse model of inherited retinal degeneration," Gene Ther 4(7):683-690 (publication date: Jul. 1997).
Kanegae et al., "Efficient gene activation in mammalian cells by using recombinant adenovirus expressing site-specific Cre recombinase," Nucleic Acids Research 23(19):3816-3821 (publication date: Oct. 11, 1995).
Keirstead et al., "Human Embryonic Stem Cell-Derived Oligodendrocyte Progenitor Cell transplants Remyelinate and Restore Locomotion after Spinal Cord Injury," J. Neurosci. 25(19):4694-4705 (publication date: May 11, 2005).
Kim et al., "Direct lineage reprogramming to neural cells," Curr Opinion Neurobiol. 22(5):778-784 (publication date: Oct. 2012, epublication date: May 30, 2012).
Kim et al., "Direct reprogramming of mouse fibroblasts to neural progenitors," Proc. Natl. Acad. Sci. 108(19): 7838-7843 (publication date: May 10, 2011, epublication date: Apr. 26, 2011).
Kimatura et al., Retrovirus-mediated gene transfer and expression cloning: Powerful tools in functional genomics, Experimental Hematology 31:1007-1014 (publication date: Nov. 2003).
Kwon et al., "Canonical Wnt signaling is a positive regulator of mammalian cardiac progenitors," Proc. Natl. Acad. Sci. 104(26):10894-10899 (publication date: Jun. 26, 2007, epublication date: Jun. 18, 2007).

(56) References Cited

OTHER PUBLICATIONS

Li et al., "In Vivo Transfer of a Reporter Gene to the Retina Mediated by an Adenoviral Vector," Invest Opthalmol Vis Sci 35(5):2543-2549 (publication date: Apr. 1994).
Li et al., "Phenotype correction in retinal pigment epithelium in murine mucopolysaccharidosis VII by adenovirus-mediated gene transfer," Proc. Natl. Acad. Sci. 92:7700-7704 (publication date: Aug. 15, 1995).
Lian et al., "Directed cardiomyocyte differentiation from human pluripotent stem cells by modulating Wnt/β-catenin signaling under fully defined conditions," Nat Protoc 8(1): 162-175 (publication date: Jan. 2013, epublication date: Dec. 20, 2012).
Linn et al., "Conservation of an AE3 CI sup minus/HCO sub 3 sup minus Exchanger Cardiac-Specific Exon and Promoter Region and AE3 mRNA Expression Patterns in Murine and Human Hearts," Circ. Res. 76(4):584-591 (Apr. 1995).
Mendelson et al., "Expression and Rescue of a Nonselected Marker from an Integrated AAV Vector," Virol. 166(1):154-165 (Sep. 1988).
Miyoshi et al., "Development of a Self-Inactivating Lentivirus Vector," J. Virol. 72(10):8150-8157 (publication date: Oct. 1998).
Miyoshi et al., "Stable and efficient gene transfer into the retina using an HIV-based lentiviral vector," Proc. Natl. Acad. Sci. 94(19):10319-10323 (publication date: Sep. 16, 1997).
Mohammad et al., "Inner Ear Hair Cell-Like Cells from Human Embryonic Stem Cells," Stem Cells and Dev. 23(11):1275-1284 (publication date: Nov. 11, 2014, epublication date: Mar. 10, 2014).
Morgenstern et al., "Advanced mammalian gene transfer: high titre retroviral vectors with multiple drug selection markers and a complementary helper-free packaging cell line," Nucleic Acids Research 18(12):3587-3596 (publication date: Jun. 25, 1990).
Morita et al., "Plat-E: an efficient and stable system for transient packaging of retroviruses," Gene Therapy 7(12):1063-1066 (publication date: Jun. 2000).
Naldini et al., "In Vivo Gene Delivery and Stable Transduction of Nondividing Cells by a Lentiviral Vector," Science, 272:263-267 (publication date: Apr. 12, 1996).
Nègre et al., "Lentiviral Vectors Derived from Simian Immunodeficiency Virus," Current Topics in Microbiology and Immunology, 261:53-74 (2002).
Onishi et al., "Applications of retrovirus-mediated expression cloning," Experimental Hematology, 24(2):324-329 (publication date: Feb. 1996).
Parmacek et al., "A Novel Myogenic Regulatory Circuit Controls Slow/Cardiac Troponin C Gene Transcription in Skeletal Muscle," Mol. Cell. Biol. 14(3):1870-1885 (publication date: Mar. 1994).
Qian et al., "In vivo reprogramming of murine cardiac fibroblasts into induced cardiomyocytes," Nature 485(7400):593-598 (publication date: May 31, 2012).
Reiss et al., "Myocardial Infarction is Coupled with the Activation of Cyclins and cyclin-Dependent Kinases in Myocytes," Experimental Cell Research 225:44-54 (publication date: May 25, 1996).
Rivière et al., "Effects of retroviral vector design on expression of human adenosine deaminase in murine bone marrow transplant recipients engrafted with genetically modified cells," Proc. Natl. Acad. Sci., 92(15):6733-6737 (publication date: Jul. 1995).
Robbins et al., "In Vivo Definition of a Cardiac Specific Promoter and Its Potential Utility in Remodeling the Heart," Ann. N.Y. Acad. Sci. 752:492-505 (Mar. 1995).
Rolling et al., "Evaluation of Adeno-Associated Virus-Mediated Gene Transfer into the Rat Retina by Clinical Fluorescence Photography," Hum Gene Ther 10(4):641-648 (publication date: Mar. 1, 1999).
Ronaghi et al. "Inner ear hair cell-like cells from human embryonic stem cells," Stem Cells and Dev. 23(11):1275-1284 (publication date: Jun. 1, 2014, epublication date: Mar. 10, 2014).
Sakamoto et al., "A vitrectomy improves the transfection efficiency of adenoviral vector-mediated gene transfer to Muller cells," Hum Gene Ther 5(8):1088-1097 (publication date: Aug. 3, 1998).
Salani et al., "Generation of skeletal muscle cells from embryonic and induced pluripotent stem cells as an in vitro model and for therapy of muscular dystrophies," J Cell Mol. Med. 16(7):1353-1364 (publication date: Jul. 2012).
Samulski et al., "Helper-Free Stocks of Recombinant Adeno-Associated Viruses: Normal Integration Does Not Require Viral Gene Expression," J. Vir. 63(9):3822-3828 (publication date: Sep. 1989).
Sartorelli et al., "Myocardial activation of the human cardiac alpha-actin promoter by helix-loop-helix proteins," Proc. Natl. Acad. Sci. USA 89(9):4047-4051 (Publication date: May 1, 1992).
Saxena et al. "Stromel cell-derived factor-1alpha is cardioprotective after myocardial infarction," Circulation 117(17): 2224-2231 (publication date: Apr. 29, 2008, epublication date: Apr. 21, 2008).
Takahashi et al., "Rescue from Photoreceptor Degeneration in the rd Mouse by Human Immunodeficiency Virus Vector-Mediated Gene Transfer," J Virol 73(9):7812-7816 (publication date: Sep. 1999).
Takahashi et al., "Induction of pluripotent stem cells from adult human fibroblasts by defined factors," Cell 131(5):861-872 (publication date: Nov. 30, 2007).
Tamamori-Adachi, M. et al., "Critical Role of Cyclin D1 Nuclear Import in Cardiomyocyte Proliferation," Circulation Research 92(1):e12-9 (publication date: Jan. 10, 2003).
Yamagishi et al., "The Combinatorial Activities of Nkx2.5 and dHAND Are Essential for Cardiac Ventricle Formation," Dev Biol 239: 190-203 (publication date: Nov. 15, 2001).
Yazawa et al., "Current progress in suicide gene therapy for cancer," World J. Surg. 26(7):783-9 (epublication date: Apr. 15, 2002).
Yee et al., "Generation of high-titer pseudotyped retroviral vectors with very broad host range," Methods Cell Biol., Pt A:99-112 (1994).
Zangi et al., "Modified mRNA directs the fate of heart progenitor cells and induces vascular regeneration after myocardial infarction," Nature biotechnology 31(10):898-907 (publication date: Oct. 2013, epublication date: Sep. 8, 2013).
Zielke et al., "FUCCI sensors: powerful new tools for analysis of cell proliferation," WIREs Dev Biol 4:469-487 (publication date: Sep.-Oct. 2015, epublication date: Apr. 1, 2015).
"European Application Serial No. 16777144.3, Response filed May 30, 2019 to Extended European Search Report dated Nov. 6, 2018", 10 pgs.
"Japanese Application Serial No. 2018-503729, Amendment filed Apr. 4, 2019", w/ English Translation, 40 pgs.
"Japanese Application Serial No. 2018-503729, Notification of Reasons for Refusal dated Feb. 4, 2020", w Partial English Translation, 8 pgs.

* cited by examiner

| Gene | adult | Neonatal |
|---|---|---|
| AK029786 | 5.315104 | 0 |
| ANLN | -4 | 0 |
| Ap1g2 | -2.57465 | 0 |
| Aurora B | -2.24 | 0 |
| Brd8 | -2.15007 | 0 |
| Casp9 | -2.44964 | 0 |
| CCND1 | -4 | 0 |
| CDC5 | -2 | 0 |
| Cdh6 | -3.74212 | 0 |
| CDK10 | -3 | 0 |
| CDK2 | -2 | 0 |
| Cdk3 | -2.30523 | 0 |
| CDK4 | -2 | 0 |
| CENPA | -4 | 0 |
| Cops5 | -1.95796 | 0 |
| Ctbp1 | -3.29744 | 0 |
| Ddx5 | 1.529456 | 0 |
| Dlc1 | 1.568299 | 0 |
| E2F1 | -4 | 0 |
| Ensa | -2.13744 | 0 |
| Fgf8 | -2.82356 | 0 |
| Foxq1 | -1.86831 | 0 |
| Hif1a | 2.345299 | 0 |
| Hira | 1.695562 | 0 |
| Hoxa5 | 1.897914 | 0 |
| Hrasls3 | -2.96629 | 0 |
| Il15ra | 1.634971 | 0 |
| Kcnq3 | 1.987909 | 0 |
| Ki67 | -4 | 0 |
| KIF4A | -2.12 | 0 |
| Ltf | -4.64768 | 0 |
| Mllt10 | -2.86947 | 0 |
| Nup98 | 3.774005 | 0 |
| PLK1 | -3.15 | 0 |
| Plscr2 | 1.58689 | 0 |
| Ppgb | 1.683699 | 0 |
| PRC1 | -3.53 | 0 |
| Prkwnk1 | 3.283643 | 0 |
| Prlr | -2.29046 | 0 |
| Ranbp2 | -2.01118 | 0 |
| Rcn2 | -5.7697 | 0 |
| Sin3b | 1.556179 | 0 |
| Six2 | -2.75452 | 0 |
| Slc1a5 | 1.883835 | 0 |
| Slc4a4 | 1.580591 | 0 |
| Sln | -2.55444 | 0 |
| SMC1L1 | -3 | 0 |
| Sorcs3 | -3.09612 | 0 |
| Sorl1 | 1.579829 | 0 |
| Sox8 | -2.05888 | 0 |
| Statip1 | 2.39195 | 0 |
| Syngr2 | 1.606449 | 0 |
| Tcf20 | 2.069102 | 0 |
| Tia1 | -2.74685 | 0 |
| TOP3B | -2 | 0 |
| Trim17 | -2.04037 | 0 |
| Usf1 | 1.55958 | 0 |
| WEE1 | -3 | 0 |
| Wisp1 | -2.68672 | 0 |

SEQUENCE LISTING

<160> NUMBER OF SEQ ID NOS: 20

<210> SEQ ID NO 1
<211> LENGTH: 1923
<212> TYPE: DNA
<213> ORGANISM: Homo sapiens -continued

<400> SEQUENCE: 1

```
agcgcggtga gtttgaaact gctcgcactt ggcttcaaag ctggctcttg gaaattgagc      60
ggagagcgac gcggttgttg tagctgccgc tgcggccgcc gcggaataat aagccgggat     120
ctaccatacc cattgactaa ctatggaaga ttataccaaa atagagaaaa ttggagaagg     180
tacctatgga gttgtgtata agggtagaca caaaactaca ggtcaagtgg tagccatgaa     240
aaaaatcaga ctagaaagtg aagaggaagg ggttcctagt actgcaattc gggaaatttc     300
tctattaaag gaacttcgtc atccaaatat agtcagtctt caggatgtgc ttatgcagga     360
ttccaggtta tatctcatct ttgagtttct ttccatggat ctgaagaaat acttggattc     420
tatccctcct ggtcagtaca tggattcttc acttgttaag agttatttat accaaatcct     480
acaggggatt gtgttttgtc actctagaag agttcttcac agagacttaa aacctcaaaa     540
tctcttgatt gatgacaaag gaacaattaa actggctgat tttggccttg ccagagcttt     600
tggaatacct atcagagtat atacacatga ggtagtaaca ctctggtaca gatctccaga     660
agtattgctg gggtcagctc gttactcaac tccagttgac atttggagta taggcaccat     720
atttgctgaa ctagcaacta agaaaccact tttccatggg gattcagaaa ttgatcaact     780
cttcaggatt ttcagagctt tgggcactcc caataatgaa gtgtggccag aagtggaatc     840
tttacaggac tataagaata catttcccaa atggaaacca ggaagcctag catcccatgt     900
caaaaacttg gatgaaaatg gcttggattt gctctcgaaa atgttaatct atgatccagc     960
caaacgaatt tctggcaaaa tggcactgaa tcatccatat tttaatgatt tggacaatca    1020
gattaagaag atgtagcttt ctgacaaaaa gtttccatat gttatatcaa cagatagttg    1080
tgtttttatt gttaactctt gtctattttt gtcttatata tatttctttg ttatcaaact    1140
tcagctgtac ttcgtcttct aatttcaaaa atataactta aaaatgtaaa tattctatat    1200
gaatttaaat ataattctgt aaatgtgtgt aggtctcact gtaacaacta tttgttacta    1260
taataaaact ataatattga tgtcaggaat caggaaaaaa tttgagttgg cttaaatcat    1320
ctcagtcctt atggcagttt tattttcctg tagttggaac tactaaaatt taggaaaatg    1380
ctaagttcaa gtttcgtaat gctttgaagt atttttatgc tctgaatgtt taaatgttct    1440
catcagtttc ttgccatgtt gttaactata caacctggct aaagatgaat atttttctac    1500
tggtatttta atttttgacc taaatgttta agcattcgga atgagaaaac tatacagatt    1560
tgagaaatga tgctaaattt ataggagttt tcagtaactt aaaaagctaa catgagagca    1620
tgccaaaatt tgctaagtct tacaaagatc aagggctgtc cgcaacaggg aagaacagtt    1680
ttgaaaattt atgaactatc ttatttttag gtaggttttg aaagcttttt gtctaagtga    1740
attcttatgc cttggtcaga gtaataactg aaggagttgc ttatcttggc tttcgagtct    1800
gagtttaaaa ctacacattt tgacatagtg tttattagca gccatctaaa aaggctctaa    1860
tgtatattta actaaaatta ctagctttgg gaattaaact gtttaacaaa taaaaaaaaa    1920
aaa                                                                  1923
```

<210> SEQ ID NO 2
<211> LENGTH: 297
<212> TYPE: PRT
<213> ORGANISM: Homo sapiens

<400> SEQUENCE: 2

```
Met Glu Asp Tyr Thr Lys Ile Glu Lys Ile Gly Glu Gly Thr Tyr Gly
1               5                   10                  15

Val Val Tyr Lys Gly Arg His Lys Thr Thr Gly Gln Val Val Ala Met
            20                  25                  30

Lys Lys Ile Arg Leu Glu Ser Glu Glu Glu Gly Val Pro Ser Thr Ala
        35                  40                  45

Ile Arg Glu Ile Ser Leu Leu Lys Glu Leu Arg His Pro Asn Ile Val
    50                  55                  60

Ser Leu Gln Asp Val Leu Met Gln Asp Ser Arg Leu Tyr Leu Ile Phe
65                  70                  75                  80

Glu Phe Leu Ser Met Asp Leu Lys Lys Tyr Leu Asp Ser Ile Pro Pro
                85                  90                  95

Gly Gln Tyr Met Asp Ser Ser Leu Val Lys Ser Tyr Leu Tyr Gln Ile
            100                 105                 110

Leu Gln Gly Ile Val Phe Cys His Ser Arg Arg Val Leu His Arg Asp
        115                 120                 125

Leu Lys Pro Gln Asn Leu Leu Ile Asp Asp Lys Gly Thr Ile Lys Leu
    130                 135                 140

Ala Asp Phe Gly Leu Ala Arg Ala Phe Gly Ile Pro Ile Arg Val Tyr
145                 150                 155                 160

Thr His Glu Val Val Thr Leu Trp Tyr Arg Ser Pro Glu Val Leu Leu
                165                 170                 175

Gly Ser Ala Arg Tyr Ser Thr Pro Val Asp Ile Trp Ser Ile Gly Thr
            180                 185                 190

Ile Phe Ala Glu Leu Ala Thr Lys Lys Pro Leu Phe His Gly Asp Ser
        195                 200                 205

Glu Ile Asp Gln Leu Phe Arg Ile Phe Arg Ala Leu Gly Thr Pro Asn
    210                 215                 220

Asn Glu Val Trp Pro Glu Val Glu Ser Leu Gln Asp Tyr Lys Asn Thr
225                 230                 235                 240

Phe Pro Lys Trp Lys Pro Gly Ser Leu Ala Ser His Val Lys Asn Leu
                245                 250                 255

Asp Glu Asn Gly Leu Asp Leu Leu Ser Lys Met Leu Ile Tyr Asp Pro
            260                 265                 270

Ala Lys Arg Ile Ser Gly Lys Met Ala Leu Asn His Pro Tyr Phe Asn
        275                 280                 285

Asp Leu Asp Asn Gln Ile Lys Lys Met
    290                 295
```

<210> SEQ ID NO 3
<211> LENGTH: 2177
<212> TYPE: DNA
<213> ORGANISM: Homo sapiens

<400> SEQUENCE: 3

```
cgaacgcctt cgcgcgatcg ccctggaaac gcattctctg cgaccggcag ccgccaatgg     60

gaagggagtg agtgccacga acaggccaat aaggagggag cagtgcgggg tttaaatctg    120

aggctaggct ggctcttctc ggcgtgctgc ggcggaacgg ctgttggttt ctgctgggtg    180

taggtccttg gctggtcggg cctccggtgt tctgcttctc cccgctgagc tgctgcctgg    240

tgaagaggaa gccatggcgc tccgagtcac caggaactcg aaaattaatg ctgaaaataa    300

ggcgaagatc aacatggcag gcgcaaagcg cgttcctacg gcccctgctg caacctccaa    360
```

-continued

```
gcccggactg aggccaagaa cagctcttgg ggacattggt aacaaagtca gtgaacaact    420

gcaggccaaa atgcctatga agaaggaagc aaaaccttca gctactggaa aagtcattga    480

taaaaaacta ccaaaacctc ttgaaaaggt acctatgctg gtgccagtgc cagtgtctga    540

gccagtgcca gagccagaac ctgagccaga acctgagcct gttaaagaag aaaaactttc    600

gcctgagcct attttggttg atactgcctc tccaagccca atggaaacat ctggatgtgc    660

ccctgcagaa gaagacctgt gtcaggcttt ctctgatgta attcttgcag taaatgatgt    720

ggatgcagaa gatggagctg atccaaacct ttgtagtgaa tatgtgaaag atatttatgc    780

ttatctgaga caacttgagg aagagcaagc agtcagacca aaatacctac tgggtcggga    840

agtcactgga aacatgagag ccatcctaat tgactggcta gtacaggttc aaatgaaatt    900

caggttgttg caggagacca tgtacatgac tgtctccatt attgatcggt tcatgcagaa    960

taattgtgtg cccaagaaga tgctgcagct ggttggtgtc actgccatgt ttattgcaag   1020

caaatatgaa gaaatgtacc ctccagaaat tggtgacttt gcttttgtga ctgacaacac   1080

ttatactaag caccaaatca gacagatgga aatgaagatt ctaagagctt taaactttgg   1140

tctgggtcgg cctctacctt tgcacttcct tcggagagca tctaagattg gagaggttga   1200

tgtcgagcaa catactttgg ccaaatacct gatggaacta actatgttgg actatgacat   1260

ggtgcacttt cctccttctc aaattgcagc aggagctttt tgcttagcac tgaaaattct   1320

ggataatggt gaatggacac caactctaca acattacctg tcatatactg aagaatctct   1380

tcttccagtt atgcagcacc tggctaagaa tgtagtcatg gtaaatcaag gacttacaaa   1440

gcacatgact gtcaagaaca agtatgccac atcgaagcat gctaagatca gcactctacc   1500

acagctgaat tctgcactag ttcaagattt agccaaggct gtggcaaagg tgtaacttgt   1560

aaacttgagt tggagtacta tatttacaaa taaaattggc accatgtgcc atctgtacat   1620

attactgttg catttacttt taataaagct tgtggcccct tttacttttt tatagcttaa   1680

ctaatttgaa tgtggttact tcctactgta gggtagcgga aaagttgtct taaaaggtat   1740

ggtggggata tttttaaaaa ctccttttgg tttacctggg gatccaattg atgtatatgt   1800

ttatatactg ggttcttgtt ttatatacct ggcttttact ttattaatat gagttactga   1860

aggtgatgga ggtatttgaa aattttactt ccataggaca tactgcatgt aagccaagtc   1920

atggagaatc tgctgcatag ctctatttta aagtaaaagt ctaccaccga atccctagtc   1980

cccctgtttt ctgtttcttc ttgtgattgc tgccataatt ctaagttatt tacttttacc   2040

actatttaag ttatcaactt tagctagtat cttcaaactt tcactttgaa aaatgagaat   2100

tttatattct aagccagttt tcattttggt tttgtgtttt ggttaataaa acaatactca   2160

aatacaaaaa aaaaaaa                                                  2177


<210> SEQ ID NO 4
<211> LENGTH: 433
<212> TYPE: PRT
<213> ORGANISM: Homo sapiens

<400> SEQUENCE: 4

Met Ala Leu Arg Val Thr Arg Asn Ser Lys Ile Asn Ala Glu Asn Lys
1               5                   10                  15

Ala Lys Ile Asn Met Ala Gly Ala Lys Arg Val Pro Thr Ala Pro Ala
            20                  25                  30

Ala Thr Ser Lys Pro Gly Leu Arg Pro Arg Thr Ala Leu Gly Asp Ile
        35                  40                  45
```

```
Gly Asn Lys Val Ser Glu Gln Leu Gln Ala Lys Met Pro Met Lys Lys
    50                  55                  60

Glu Ala Lys Pro Ser Ala Thr Gly Lys Val Ile Asp Lys Lys Leu Pro
65                  70                  75                  80

Lys Pro Leu Glu Lys Val Pro Met Leu Val Pro Val Pro Val Ser Glu
                85                  90                  95

Pro Val Pro Glu Pro Glu Pro Glu Pro Glu Pro Glu Pro Val Lys Glu
            100                 105                 110

Glu Lys Leu Ser Pro Glu Pro Ile Leu Val Asp Thr Ala Ser Pro Ser
        115                 120                 125

Pro Met Glu Thr Ser Gly Cys Ala Pro Ala Glu Glu Asp Leu Cys Gln
    130                 135                 140

Ala Phe Ser Asp Val Ile Leu Ala Val Asn Asp Val Asp Ala Glu Asp
145                 150                 155                 160

Gly Ala Asp Pro Asn Leu Cys Ser Glu Tyr Val Lys Asp Ile Tyr Ala
                165                 170                 175

Tyr Leu Arg Gln Leu Glu Glu Glu Gln Ala Val Arg Pro Lys Tyr Leu
            180                 185                 190

Leu Gly Arg Glu Val Thr Gly Asn Met Arg Ala Ile Leu Ile Asp Trp
        195                 200                 205

Leu Val Gln Val Gln Met Lys Phe Arg Leu Leu Gln Glu Thr Met Tyr
    210                 215                 220

Met Thr Val Ser Ile Ile Asp Arg Phe Met Gln Asn Asn Cys Val Pro
225                 230                 235                 240

Lys Lys Met Leu Gln Leu Val Gly Val Thr Ala Met Phe Ile Ala Ser
                245                 250                 255

Lys Tyr Glu Glu Met Tyr Pro Pro Glu Ile Gly Asp Phe Ala Phe Val
            260                 265                 270

Thr Asp Asn Thr Tyr Thr Lys His Gln Ile Arg Gln Met Glu Met Lys
        275                 280                 285

Ile Leu Arg Ala Leu Asn Phe Gly Leu Gly Arg Pro Leu Pro Leu His
    290                 295                 300

Phe Leu Arg Arg Ala Ser Lys Ile Gly Glu Val Asp Val Glu Gln His
305                 310                 315                 320

Thr Leu Ala Lys Tyr Leu Met Glu Leu Thr Met Leu Asp Tyr Asp Met
                325                 330                 335

Val His Phe Pro Pro Ser Gln Ile Ala Ala Gly Ala Phe Cys Leu Ala
            340                 345                 350

Leu Lys Ile Leu Asp Asn Gly Glu Trp Thr Pro Thr Leu Gln His Tyr
        355                 360                 365

Leu Ser Tyr Thr Glu Glu Ser Leu Leu Pro Val Met Gln His Leu Ala
    370                 375                 380

Lys Asn Val Val Met Val Asn Gln Gly Leu Thr Lys His Met Thr Val
385                 390                 395                 400

Lys Asn Lys Tyr Ala Thr Ser Lys His Ala Lys Ile Ser Thr Leu Pro
                405                 410                 415

Gln Leu Asn Ser Ala Leu Val Gln Asp Leu Ala Lys Ala Val Ala Lys
            420                 425                 430

Val
```

<210> SEQ ID NO 5
<211> LENGTH: 1314
<212> TYPE: DNA
<213> ORGANISM: Homo sapiens

<400> SEQUENCE: 5

```
cggggcggga gatttgaaaa gtccttggcc agggcgcggc gtggcagatt cagttgtttg     60
cgggcggccg ggagagtagc agtgccttgg accccagctc tcctccccct ttctctctaa    120
ggatggccca gaaggagaac tcctacccct ggccctacgg ccgacagacg gctccatctg    180
gcctgagcac cctgccccag cgagtcctcc ggaaagagcc tgtcacccca tctgcacttg    240
tcctcatgag ccgctccaat gtccagccca cagctgcccc tggccagaag gtgatggaga    300
atagcagtgg gacacccgac atcttaacgc ggcacttcac aattgatgac tttgagattg    360
ggcgtcctct gggcaaaggc aagtttggaa acgtgtactt ggctcgggag aagaaaagcc    420
atttcatcgt ggcgctcaag gtcctcttca agtcccagat agagaaggag ggcgtggagc    480
atcagctgcg cagagagatc gaaatccagg cccacctgca ccatcccaac atcctgcgtc    540
tctacaacta tttttatgac cggaggagga tctacttgat tctagagtat gcccccgcg    600
gggagctcta caaggagctg cagaagagct gcacatttga cgagcagcga acagccacga    660
tcatggagga gttggcagat gctctaatgt actgccatgg gaagaaggtg attcacagag    720
acataaagcc agaaaatctg ctcttagggc tcaagggaga gctgaagatt gctgacttcg    780
gctggtctgt gcatgcgccc tccctgagga ggaagacaat gtgtggcacc ctggactacc    840
tgcccccaga gatgattgag gggcgcatgc acaatgagaa ggtggatctg tggtgcattg    900
gagtgctttg ctatgagctg ctggtgggga acccaccctt tgagagtgca tcacacaacg    960
agacctatcg ccgcatcgtc aaggtggacc taaagttccc cgcttccgtg cccatgggag   1020
cccaggacct catctccaaa ctgctcaggc ataacccctc ggaacggctg cccctggccc   1080
aggtctcagc ccacccttgg gtccgggcca actctcggag ggtgctgcct ccctctgccc   1140
ttcaatctgt cgcctgatgg tccctgtcat tcactcgggt gcgtgtgttt gtatgtctgt   1200
gtatgtatag gggaaagaag ggatccctaa ctgttccctt atctgttttc tacctcctcc   1260
tttgtttaat aaaggctgaa gctttttgta ctcatgaaaa aaaaaaaaaa aaaa         1314
```

<210> SEQ ID NO 6
<211> LENGTH: 344
<212> TYPE: PRT
<213> ORGANISM: Homo sapiens

<400> SEQUENCE: 6

```
Met Ala Gln Lys Glu Asn Ser Tyr Pro Trp Pro Tyr Gly Arg Gln Thr
1               5                   10                  15

Ala Pro Ser Gly Leu Ser Thr Leu Pro Gln Arg Val Leu Arg Lys Glu
            20                  25                  30

Pro Val Thr Pro Ser Ala Leu Val Leu Met Ser Arg Ser Asn Val Gln
        35                  40                  45

Pro Thr Ala Ala Pro Gly Gln Lys Val Met Glu Asn Ser Ser Gly Thr
    50                  55                  60

Pro Asp Ile Leu Thr Arg His Phe Thr Ile Asp Asp Phe Glu Ile Gly
65                  70                  75                  80

Arg Pro Leu Gly Lys Gly Lys Phe Gly Asn Val Tyr Leu Ala Arg Glu
                85                  90                  95

Lys Lys Ser His Phe Ile Val Ala Leu Lys Val Leu Phe Lys Ser Gln
            100                 105                 110

Ile Glu Lys Glu Gly Val Glu His Gln Leu Arg Arg Glu Ile Glu Ile
        115                 120                 125
```

-continued

```
Gln Ala His Leu His His Pro Asn Ile Leu Arg Leu Tyr Asn Tyr Phe
    130                 135                 140

Tyr Asp Arg Arg Arg Ile Tyr Leu Ile Leu Glu Tyr Ala Pro Arg Gly
145                 150                 155                 160

Glu Leu Tyr Lys Glu Leu Gln Lys Ser Cys Thr Phe Asp Glu Gln Arg
                165                 170                 175

Thr Ala Thr Ile Met Glu Glu Leu Ala Asp Ala Leu Met Tyr Cys His
            180                 185                 190

Gly Lys Lys Val Ile His Arg Asp Ile Lys Pro Glu Asn Leu Leu Leu
        195                 200                 205

Gly Leu Lys Gly Glu Leu Lys Ile Ala Asp Phe Gly Trp Ser Val His
    210                 215                 220

Ala Pro Ser Leu Arg Arg Lys Thr Met Cys Gly Thr Leu Asp Tyr Leu
225                 230                 235                 240

Pro Pro Glu Met Ile Glu Gly Arg Met His Asn Glu Lys Val Asp Leu
                245                 250                 255

Trp Cys Ile Gly Val Leu Cys Tyr Glu Leu Leu Val Gly Asn Pro Pro
            260                 265                 270

Phe Glu Ser Ala Ser His Asn Glu Thr Tyr Arg Arg Ile Val Lys Val
        275                 280                 285

Asp Leu Lys Phe Pro Ala Ser Val Pro Met Gly Ala Gln Asp Leu Ile
    290                 295                 300

Ser Lys Leu Leu Arg His Asn Pro Ser Glu Arg Leu Pro Leu Ala Gln
305                 310                 315                 320

Val Ser Ala His Pro Trp Val Arg Ala Asn Ser Arg Arg Val Leu Pro
                325                 330                 335

Pro Ser Ala Leu Gln Ser Val Ala
            340
```

<210> SEQ ID NO 7
<211> LENGTH: 2860
<212> TYPE: DNA
<213> ORGANISM: Mus musculus

<400> SEQUENCE: 7

```
actcggcctc taagctcctg gagttgctgc gtccgcgcag tccggaactg cggtgtggcc      60

ccagccggga cagagagggt ccgtcgtaac ctgttgagta actatggaag actatatcaa     120

aatagagaaa attggagaag gtacttacgg tgtggtgtat aagggtagac acagagtcac     180

tggccagata gtggccatga agaagatcag acttgaaagc gaggaagaag gagtgcccag     240

tactgcaatt cgggaaatct ctctattaaa agaacttcga catccaaata tagtcagcct     300

gcaggatgtg ctcatgcagg actccaggct gtatctcatc tttgagttcc tgtccatgga     360

cctcaagaag tacctggact ccatccctcc tgggcagttc atggattctt cactcgttaa     420

gagttactta caccaaatcc tccagggaat tgtgttttgc cactcccggc gagttcttca     480

cagagacttg aaacctcaaa atctattgat tgatgacaaa ggaacaatca aactggctga     540

tttcggcctt gccagagcgt ttggaatacc gatacgagtg tacacacacg aggtagtgac     600

gctgtggtac cgatctccag aagtgttgct gggctcggct cgttactcca ctccggttga     660

catctggagt atagggacca tatttgcaga actggccacc aagaagccgc ttttccacgg     720

cgactcagag attgaccagc tcttcaggat cttcagagct ctgggcactc ctaacaacga     780

agtgtggcca gaagtcgagt ccctgcagga ctacaagaac acctttccca agtggaagcc     840

ggggagcctc gcatcccacg tcaagaacct ggacgagaac ggcttggatt tgctctcaaa     900
```

-continued

```
aatgctagtc tatgatcctg ccaaacgaat ctctggcaaa atggccctga agcacccgta    960

ctttgatgac ttggacaatc agattaagaa gatgtagccc tctggatgga tgtccctgtc   1020

tgctggtcgt aggggaagat cgtgttgttt accgttggct ctcttcctgt cttgtatagt   1080

tttctttgtt tgtaaactgt catctggact tttcttaatt tcctacgtat aacttaatta   1140

acatgtaaat attattccat atgaatttaa atataattct gtatatgtgc agatgtcact   1200

gtggtggctg ttaattacta taacacaagt gttaattact acaacataag acttgagtct   1260

ccctagactt cccagcagcc attcctgcag ctcggagcac agttgaagga gctgagctca   1320

ggcctcgtga tgctttcaag tgcctccgtg ttctggatat atatgattcc tggtcagttt   1380

cttgccattt ggaaactaca acccacctac ggacagtgtt tttctacttg tgcttaagca   1440

gttgggatga gaaggccaaa gacccgagga tgtctagagt aatgaccccc agatggaagt   1500

gcaccaaagc tggctgggtt tcacagctag agatcagggg ctgtccagag caggacagct   1560

tagaacattt atgaagactc cctattttta ggtttgttgt aaagctgttg tctagttgga   1620

ttcctgtgct ctgcatggtc agaggtaggt tagaggattt gccttggctt ctaaatccaa   1680

tttgaaaact gcttaaaatc tcctgtcctc tcttagcagt gtctaaaaat gtccttgtcc   1740

aaatatttag ctgagattcc tcactttgga aaaggagccg tatcgctgtg ctgcttagtg   1800

taattcttag aagcagcctg acttatctgc tagcagtcaa agggatgcct gagacgactg   1860

ctcctcttag aactaaaggc tggatgcttt aagtttgtct actgtttgga ggatctcggt   1920

aagactgagc ccctgttcct gtggccacct cagtttacca gtacctcagc ctcagcctcc   1980

tgcatttgct ggagtcaggg aaggtcccca gccctgagcc ctgacgctcc tgattgtaga   2040

gactgtcagt tggaggtaaa acgttcattg aagtagtcag cagccacatg catttagggc   2100

actccagtgt cagagaccat cctggaggtt tctaaccctg ccgctggcag tctactccca   2160

agacagatca gttagagtgg tcagcaaaca ccaactgctg cagaaacctg tgttggtgtg   2220

gttccctgct gctgctggga actgggccca agactagaga gcttggggct gcggttgatc   2280

atgggttctg ttcctgcatt acaccttgaa atccaagcct tctaatatct cccttcggat   2340

cataagttgt gaatttggtc ctccgccccc gccaggtttt ctatacttgg gtttgtcttg   2400

ctgacatttt caagagtcct gactaagacg gtgattagtg tgacatgact tgagaactac   2460

cgatttgaag cacacttgaa gttaacaaat tctctcatga ttatactttt aactttttat   2520

aagattgctt gagctcaccc agatctctgt tgggaagtaa ctgggtaaca aaagccgttg   2580

cactggtttg acagctaaca actgttggta ctttgtattc agaaggaatg aggtagcgat   2640

tgaatggctg ggtgttgttt tccacagttt atacactaaa aatttgggta gccaggaggt   2700

agtggcgcgc aatctttaat ctcagcagag gcagtcctat ctcttgagtt ggaggccagc   2760

ctgcctgagt tccagaccag ccagggctac aggaagaagt cttaaaaaaa tttttttcc   2820

ctgtggatgt aaacccatga gaatgactgc tgtatctatc                         2860
```

```
<210> SEQ ID NO 8
<211> LENGTH: 297
<212> TYPE: PRT
<213> ORGANISM: Mus musculus

<400> SEQUENCE: 8

Met Glu Asp Tyr Ile Lys Ile Glu Lys Ile Gly Glu Gly Thr Tyr Gly
1               5                   10                  15

Val Val Tyr Lys Gly Arg His Arg Val Thr Gly Gln Ile Val Ala Met
            20                  25                  30
```

-continued

```
Lys Lys Ile Arg Leu Glu Ser Glu Glu Glu Gly Val Pro Ser Thr Ala
        35                  40                  45

Ile Arg Glu Ile Ser Leu Leu Lys Glu Leu Arg His Pro Asn Ile Val
    50                  55                  60

Ser Leu Gln Asp Val Leu Met Gln Asp Ser Arg Leu Tyr Leu Ile Phe
65                  70                  75                  80

Glu Phe Leu Ser Met Asp Leu Lys Lys Tyr Leu Asp Ser Ile Pro Pro
                85                  90                  95

Gly Gln Phe Met Asp Ser Ser Leu Val Lys Ser Tyr Leu His Gln Ile
            100                 105                 110

Leu Gln Gly Ile Val Phe Cys His Ser Arg Arg Val Leu His Arg Asp
        115                 120                 125

Leu Lys Pro Gln Asn Leu Leu Ile Asp Asp Lys Gly Thr Ile Lys Leu
    130                 135                 140

Ala Asp Phe Gly Leu Ala Arg Ala Phe Gly Ile Pro Ile Arg Val Tyr
145                 150                 155                 160

Thr His Glu Val Val Thr Leu Trp Tyr Arg Ser Pro Glu Val Leu Leu
                165                 170                 175

Gly Ser Ala Arg Tyr Ser Thr Pro Val Asp Ile Trp Ser Ile Gly Thr
            180                 185                 190

Ile Phe Ala Glu Leu Ala Thr Lys Lys Pro Leu Phe His Gly Asp Ser
        195                 200                 205

Glu Ile Asp Gln Leu Phe Arg Ile Phe Arg Ala Leu Gly Thr Pro Asn
    210                 215                 220

Asn Glu Val Trp Pro Glu Val Glu Ser Leu Gln Asp Tyr Lys Asn Thr
225                 230                 235                 240

Phe Pro Lys Trp Lys Pro Gly Ser Leu Ala Ser His Val Lys Asn Leu
                245                 250                 255

Asp Glu Asn Gly Leu Asp Leu Leu Ser Lys Met Leu Val Tyr Asp Pro
            260                 265                 270

Ala Lys Arg Ile Ser Gly Lys Met Ala Leu Lys His Pro Tyr Phe Asp
        275                 280                 285

Asp Leu Asp Asn Gln Ile Lys Lys Met
    290                 295


<210> SEQ ID NO 9
<211> LENGTH: 2316
<212> TYPE: DNA
<213> ORGANISM: Mus musculus

<400> SEQUENCE: 9

ggaacggctg ttagtgttta gctgtggata gccagaggtt agggtgtctt ctcgaatcgg      60

ggaacctctg attttggagg agccatggcg ctcagggtca ctaggaacac gaaaattaac     120

gcagaaaata aggccaaggt cagtatggca ggcgccaagc gtgtgcctgt gacagttact     180

gctgcttcca agcccgggct gagaccgaga actgctcttg gagacattgg taataaagtc     240

agcgaagagc tacaggcaag agtgcctctg aaaagggaag caaaaacgct aggtactgga     300

aaaggtactg ttaaagccct accaaaacct gtagagaagg tgcctgtgtg tgaaccagag     360

gtggaacttg ctgagcctga gcctgaacct gaacttgaac atgttagaga agagaagctt     420

tctcctgaac ctattttggt tgataatccc tctccaagcc cgatggaaac atctggatgt     480

gcgcctgcag aagagtatct gtgtcaggct ttctctgatg taatccttgc agtgagtgac     540

gtagacgcag atgatggggc tgacccaaac ctctgtagtg aatatgtgaa agatatctat     600
```

-continued

```
gcttatctcc gacaactgga ggaagagcag tcagttagac caaaatacct acagggtcgt    660

gaagtgactg gaaacatgag agctatcctc attgactggc taatacaggt tcagatgaaa    720

tttaggctgc ttcaggagac catgtacatg actgtgtcca ttattgatcg gttcatgcag    780

aacagttgtg tgcccaagaa gatgctacag ctggtcggtg taacggccat gtttattgca    840

agcaaatatg aggagatgta ccctccagaa ataggtgact tcgcctttgt gactaacaac    900

acgtacacta agcaccagat cagacagatg gagatgaaga ttctcagagt tctgaacttc    960

agcctgggtc gccctctgcc tctgcacttc ctccgtagag catctaaagt cggagaggtt   1020

gacgtcgagc agcacacttt ggccaaatac ctcatggagc tctccatgct ggactacgac   1080

atggtgcatt ttgctccttc tcaaattgca gctggggctt tctgcttagc gctgaaaatt   1140

cttgacaacg gtgaatggac accaactctg cagcactacc tatcctacag tgaagactcc   1200

ctgcttcctg ttatgcagca cctggctaag aatgtagtca tggtgaactg tggcctcaca   1260

aagcacatga ctgtcaagaa caagtatgca gcatctaagc atgctaagat cagcacgctg   1320

gcacagctga actgtacact agttcagaat ttgtctaagg ccgtgacaaa ggcataactc   1380

caatagactg ctacatctgc agatgcagtt ggcaccatgt gccgcctgta cataggatac   1440

ctaccgtgtt tacttgctct tcaataaagg ttgtgacttc tcattttaca tagcttaact   1500

catttgaatg ttgttgcttc tgagtttagg ctaacggaag ttgtcgaatt taggagtata   1560

ttaaaaactg catctagttt taacagtgga tccaactaat gtatatatct gtagcctata   1620

tgtctatata catccttcac tgtgtgtcct tatatcatca tgtcttctgc ctcactctag   1680

tttaaactct aaatctacca gctagtcctt tgttccattt tccagtggtt gccaccttta   1740

accactgtct cttggtttgt caactttcag atctgaaacc aagtatcttt ttttatgtaa   1800

ttatttattt gttcttaatt ggaaaatagg atgttcaaaa ttaaaggtgt gttttaaaaa   1860

gaatttgccc ccaagtctca ctatcaacag ataagggtgt attcttgtat atcctgtata   1920

gatataatca tgcatatact cccaaggaga tattttata tgggttcatt ttatcaacag   1980

tattcctatc agcattcctt tcaatgccta tattgcattt cctagtgtga acaaactgtg   2040

tgtaacatag tcattccctc ggtgggattc aagtgcattc tctcagtgcc ctccacagtg   2100

ttcttaaatg atgtttaatg tcttgcttgg cttcattcat agtagctctt ccaggggtgt   2160

gctttgaatt ctgacagcca gatgggtgtg gctgccacca taccaaggcg ccactcctgt   2220

cttgtaatgc cacctggaaa agaatcctgt ctcatttgct gttttaattt atacatctga   2280

tatcaagttg aataaaattt attggtggaa agcttt                            2316


<210> SEQ ID NO 10
<211> LENGTH: 430
<212> TYPE: PRT
<213> ORGANISM: Mus musculus

<400> SEQUENCE: 10

Met Ala Leu Arg Val Thr Arg Asn Thr Lys Ile Asn Ala Glu Asn Lys
1               5                   10                  15

Ala Lys Val Ser Met Ala Gly Ala Lys Arg Val Pro Val Thr Val Thr
            20                  25                  30

Ala Ala Ser Lys Pro Gly Leu Arg Pro Arg Thr Ala Leu Gly Asp Ile
        35                  40                  45
```

```
Gly Asn Lys Val Ser Glu Glu Leu Gln Ala Arg Val Pro Leu Lys Arg
    50                  55                  60

Glu Ala Lys Thr Leu Gly Thr Gly Lys Gly Thr Val Lys Ala Leu Pro
65                  70                  75                  80

Lys Pro Val Glu Lys Val Pro Val Cys Glu Pro Glu Val Glu Leu Ala
                85                  90                  95

Glu Pro Glu Pro Glu Pro Glu Leu Glu His Val Arg Glu Glu Lys Leu
            100                 105                 110

Ser Pro Glu Pro Ile Leu Val Asp Asn Pro Ser Pro Ser Pro Met Glu
        115                 120                 125

Thr Ser Gly Cys Ala Pro Ala Glu Glu Tyr Leu Cys Gln Ala Phe Ser
    130                 135                 140

Asp Val Ile Leu Ala Val Ser Asp Val Asp Ala Asp Asp Gly Ala Asp
145                 150                 155                 160

Pro Asn Leu Cys Ser Glu Tyr Val Lys Asp Ile Tyr Ala Tyr Leu Arg
                165                 170                 175

Gln Leu Glu Glu Glu Gln Ser Val Arg Pro Lys Tyr Leu Gln Gly Arg
            180                 185                 190

Glu Val Thr Gly Asn Met Arg Ala Ile Leu Ile Asp Trp Leu Ile Gln
        195                 200                 205

Val Gln Met Lys Phe Arg Leu Leu Gln Glu Thr Met Tyr Met Thr Val
    210                 215                 220

Ser Ile Ile Asp Arg Phe Met Gln Asn Ser Cys Val Pro Lys Lys Met
225                 230                 235                 240

Leu Gln Leu Val Gly Val Thr Ala Met Phe Ile Ala Ser Lys Tyr Glu
                245                 250                 255

Glu Met Tyr Pro Pro Glu Ile Gly Asp Phe Ala Phe Val Thr Asn Asn
            260                 265                 270

Thr Tyr Thr Lys His Gln Ile Arg Gln Met Glu Met Lys Ile Leu Arg
        275                 280                 285

Val Leu Asn Phe Ser Leu Gly Arg Pro Leu Pro Leu His Phe Leu Arg
    290                 295                 300

Arg Ala Ser Lys Val Gly Glu Val Asp Val Glu Gln His Thr Leu Ala
305                 310                 315                 320

Lys Tyr Leu Met Glu Leu Ser Met Leu Asp Tyr Asp Met Val His Phe
                325                 330                 335

Ala Pro Ser Gln Ile Ala Ala Gly Ala Phe Cys Leu Ala Leu Lys Ile
            340                 345                 350

Leu Asp Asn Gly Glu Trp Thr Pro Thr Leu Gln His Tyr Leu Ser Tyr
        355                 360                 365

Ser Glu Asp Ser Leu Leu Pro Val Met Gln His Leu Ala Lys Asn Val
    370                 375                 380

Val Met Val Asn Cys Gly Leu Thr Lys His Met Thr Val Lys Asn Lys
385                 390                 395                 400

Tyr Ala Ala Ser Lys His Ala Lys Ile Ser Thr Leu Ala Gln Leu Asn
                405                 410                 415

Cys Thr Leu Val Gln Asn Leu Ser Lys Ala Val Thr Lys Ala
            420                 425                 430
```

<210> SEQ ID NO 11
<211> LENGTH: 1957
<212> TYPE: DNA
<213> ORGANISM: Mus musculus

<400> SEQUENCE: 11
ggagattcga aagcgtccgg gtcgcggggt aaaccggttc tccgtgtgcg agcgcctagt 60
ggcgtaggct gcggctttgc ggggaactgc gggggctgca gtggtccacg gggctgatcg 120
ggttccgttg ggcggatcca cgtgcccgct atccgcctgg aaggagaggt gcaggagtac 180
ccccgacctt ggctgcgtgc tgactcgctt ccttctgccc gcccaggctt gcactccccg 240
gggatctgcc tctgcatctc ttgccttcgc tgttgtttcc ctctctgtcc agctcccctc 300
ccgctctcgc cctggagaat ggctcagaag gagaacgcct acccgtggcc ctacggctca 360
aagacgtctc agtctggcct gaacacgttg tcccagagag tcctacggaa ggagcccgcc 420
acgacatctg cgcttgctct cgtgaaccgg ttcaacagcc agtccacagc tgcccctggc 480
cagaagttgg ctgagaacaa gagtcagggc tccactgcct cgcaaggatc ccagaacaag 540
cagcctttca ctattgacaa ctttgagatt gggcgtcctt tgggcaaagg caaatttgga 600
aacgtgtact tggctcggga gaagaagagc cgtttcatcg tggcactcaa gatcctcttc 660
aagtctcaga ttgagaagga gggggtagag caccagcttc gccgagagat cgaaatccag 720
gcgcacctga aacatcccaa catccttcaa ctctacaact acttctacga ccagcagagg 780
atctacttaa tcctggaata cgcccctcgc ggggaactct acaaggaact gcagaagagt 840
cggaccttcg atgagcagcg gactgccacg atcatggagg aactgtcaga tgccctgacc 900
tactgccaca agaagaaggt aattcacaga gacataaagc cggagaacct gctgttaggt 960
ctgcagggag aactgaagat tgcagacttt ggctggtcgg tgcatgcccc atccctgagg 1020
aggaagacca tgtgcggcac gctggactat ctgcccccag agatgattga ggggcgcatg 1080
cataatgaaa tggtagatct atggtgcatc ggggtgctct gctatgaact gatggtgggg 1140
aacccaccct tcgagagccc tagccacagt gagacgtatc gtcggattgt caaggtggac 1200
ctgaagttcc cctcttctgt gccttcgggc gcccaggacc tcatctccaa gctgctcaaa 1260
cataacccct ggcaacggct gcccctggcg gaggttgcag ctcacccttg ggtccgggcc 1320
aactcaagga gggttctgcc tccctctgcc ctttagcctg ctccttggtt ttttgtccct 1380
gtcatttttc agtgttcttt gtatgtctgt gtatgtgttc tgagaagggg tgggaactgg 1440
aaactattcc tagctccagt tctaggggat ctgatctctc ttctgacctc tacaggcaaa 1500
attaggcacc cctgtggtgc acatatatgc acaccaaaca catgaagtta caaacaaaca 1560
acaaacacac agatagtgct ggagagatgg ctcggtagtt aaaagcactg gctgctcttc 1620
ccaggaacct agaactcaat tctagcacta catggtgctc acgaccactg tctgtaacac 1680
ccagtcctgg ggaatctggg gccttcgagc ctctgcagac actaggcatg gatgtggtat 1740
acatgtatgc aggcaaaaca cccatgcact gacttttaag aaaccctcta gtctgattcc 1800
tttcaatttg tcaaatgttg aatgttattt ttaaaatatt ataagccatt taatacaatt 1860
tttctttgaa acatggtata gcctagtctg tcttaaattc agaaaaatta tgaagaacaa 1920
cattttataa taaagtctta aatgtttcat gtttttg 1957

<210> SEQ ID NO 12
<211> LENGTH: 345
<212> TYPE: PRT
<213> ORGANISM: Mus musculus

<400> SEQUENCE: 12

```
Met Ala Gln Lys Glu Asn Ala Tyr Pro Trp Pro Tyr Gly Ser Lys Thr
1               5                   10                  15

Ser Gln Ser Gly Leu Asn Thr Leu Ser Gln Arg Val Leu Arg Lys Glu
            20                  25                  30

Pro Ala Thr Thr Ser Ala Leu Ala Leu Val Asn Arg Phe Asn Ser Gln
        35                  40                  45

Ser Thr Ala Ala Pro Gly Gln Lys Leu Ala Glu Asn Lys Ser Gln Gly
    50                  55                  60

Ser Thr Ala Ser Gln Gly Ser Gln Asn Lys Gln Pro Phe Thr Ile Asp
65                  70                  75                  80

Asn Phe Glu Ile Gly Arg Pro Leu Gly Lys Gly Lys Phe Gly Asn Val
                85                  90                  95

Tyr Leu Ala Arg Glu Lys Lys Ser Arg Phe Ile Val Ala Leu Lys Ile
            100                 105                 110

Leu Phe Lys Ser Gln Ile Glu Lys Glu Gly Val Glu His Gln Leu Arg
        115                 120                 125

Arg Glu Ile Glu Ile Gln Ala His Leu Lys His Pro Asn Ile Leu Gln
    130                 135                 140

Leu Tyr Asn Tyr Phe Tyr Asp Gln Gln Arg Ile Tyr Leu Ile Leu Glu
145                 150                 155                 160

Tyr Ala Pro Arg Gly Glu Leu Tyr Lys Glu Leu Gln Lys Ser Arg Thr
                165                 170                 175

Phe Asp Glu Gln Arg Thr Ala Thr Ile Met Glu Glu Leu Ser Asp Ala
            180                 185                 190

Leu Thr Tyr Cys His Lys Lys Lys Val Ile His Arg Asp Ile Lys Pro
        195                 200                 205

Glu Asn Leu Leu Leu Gly Leu Gln Gly Glu Leu Lys Ile Ala Asp Phe
    210                 215                 220

Gly Trp Ser Val His Ala Pro Ser Leu Arg Arg Lys Thr Met Cys Gly
225                 230                 235                 240

Thr Leu Asp Tyr Leu Pro Pro Glu Met Ile Glu Gly Arg Met His Asn
                245                 250                 255

Glu Met Val Asp Leu Trp Cys Ile Gly Val Leu Cys Tyr Glu Leu Met
            260                 265                 270

Val Gly Asn Pro Pro Phe Glu Ser Pro Ser His Ser Glu Thr Tyr Arg
        275                 280                 285

Arg Ile Val Lys Val Asp Leu Lys Phe Pro Ser Ser Val Pro Ser Gly
    290                 295                 300

Ala Gln Asp Leu Ile Ser Lys Leu Leu Lys His Asn Pro Trp Gln Arg
305                 310                 315                 320

Leu Pro Leu Ala Glu Val Ala Ala His Pro Trp Val Arg Ala Asn Ser
                325                 330                 335

Arg Arg Val Leu Pro Pro Ser Ala Leu
            340                 345
```

<210> SEQ ID NO 13
<211> LENGTH: 1041
<212> TYPE: DNA
<213> ORGANISM: Homo sapiens

<400> SEQUENCE: 13

```
gttcgttgca acaaattgat gagcaatgct tttttataat gccaactttg tacaaaaaag      60

ttggcatggc tacctctcga tatgagccag tggctgaaat tggtgtcggt gcctatggga     120
```

-continued

```
cagtgtacaa ggcctgtgat ccccacagtg gccactttgt ggccctcaag agtgtgagag    180

tccccaatgg aggaggaggt ggaggaggcc ttcccatcag cacagttcgt gaggtggctt    240

tactgaggcg actggaggct tttgagcatc ccaatgttgt ccggctgatg gacgtctgtg    300

ccacatcccg aactgaccgg gagatcaagg taaccctggt gtttgagcat gtagaccagg    360

acctaaggac atatctggac aaggcacccc caccaggctt gccagccgaa acgatcaagg    420

atctgatgcg ccagtttcta agaggcctag atttccttca tgccaattgc atcgttcacc    480

gagatctgaa gccagagaac attctggtga caagtggtgg aacagtcaag ctggctgact    540

ttggcctggc cagaatctac agctaccaga tggcacttac acccgtggtt gttacactct    600

ggtaccgagc tcccgaagtt cttctgcagt ccacatatgc aacacctgtg gacatgtgga    660

gtgttggctg tatctttgca gagatgtttc gtcgaaagcc tctcttctgt ggaaactctg    720

aagccgacca gttgggcaaa atctttgacc tgattgggct gcctccagag gatgactggc    780

ctcgagatgt atccctgccc cgtggagcct ttcccccag agggccccgc ccagtgcagt    840

cggtggtacc tgagatggag gagtcgggag cacagctgct gctggaaatg ctgactttta    900

acccacacaa gcgaatctct gcctttcgag ctctgcagca ctcttatcta cataaggatg    960

aaggtaatcc ggagtgccca actttcttgt acaaagttgg cattataaga aagcattgct   1020

tatcaatttg ttgcaacgaa c                                              1041
```

```
<210> SEQ ID NO 14
<211> LENGTH: 303
<212> TYPE: PRT
<213> ORGANISM: Homo sapiens

<400> SEQUENCE: 14

Met Ala Thr Ser Arg Tyr Glu Pro Val Ala Glu Ile Gly Val Gly Ala
1               5                   10                  15

Tyr Gly Thr Val Tyr Lys Ala Arg Asp Pro His Ser Gly His Phe Val
            20                  25                  30

Ala Leu Lys Ser Val Arg Val Pro Asn Gly Gly Gly Gly Gly Gly Gly
        35                  40                  45

Leu Pro Ile Ser Thr Val Arg Glu Val Ala Leu Leu Arg Arg Leu Glu
    50                  55                  60

Ala Phe Glu His Pro Asn Val Val Arg Leu Met Asp Val Cys Ala Thr
65                  70                  75                  80

Ser Arg Thr Asp Arg Glu Ile Lys Val Thr Leu Val Phe Glu His Val
                85                  90                  95

Asp Gln Asp Leu Arg Thr Tyr Leu Asp Lys Ala Pro Pro Pro Gly Leu
            100                 105                 110

Pro Ala Glu Thr Ile Lys Asp Leu Met Arg Gln Phe Leu Arg Gly Leu
        115                 120                 125

Asp Phe Leu His Ala Asn Cys Ile Val His Arg Asp Leu Lys Pro Glu
    130                 135                 140

Asn Ile Leu Val Thr Ser Gly Gly Thr Val Lys Leu Ala Asp Phe Gly
145                 150                 155                 160

Leu Ala Arg Ile Tyr Ser Tyr Gln Met Ala Leu Thr Pro Val Val Val
                165                 170                 175

Thr Leu Trp Tyr Arg Ala Pro Glu Val Leu Leu Gln Ser Thr Tyr Ala
            180                 185                 190

Thr Pro Val Asp Met Trp Ser Val Gly Cys Ile Phe Ala Glu Met Phe
        195                 200                 205
```

-continued

```
Arg Arg Lys Pro Leu Phe Cys Gly Asn Ser Glu Ala Asp Gln Leu Gly
    210                 215                 220

Lys Ile Phe Asp Leu Ile Gly Leu Pro Pro Glu Asp Asp Trp Pro Arg
225                 230                 235                 240

Asp Val Ser Leu Pro Arg Gly Ala Phe Pro Pro Arg Gly Pro Arg Pro
                245                 250                 255

Val Gln Ser Val Val Pro Glu Met Glu Glu Ser Gly Ala Gln Leu Leu
            260                 265                 270

Leu Glu Met Leu Thr Phe Asn Pro His Lys Arg Ile Ser Ala Phe Arg
        275                 280                 285

Ala Leu Gln His Ser Tyr Leu His Lys Asp Glu Gly Asn Pro Glu
    290                 295                 300


<210> SEQ ID NO 15
<211> LENGTH: 4304
<212> TYPE: DNA
<213> ORGANISM: Homo sapiens

<400> SEQUENCE: 15

cacacggact acaggggagt tttgttgaag ttgcaaagtc ctggagcctc cagagggctg      60

tcggcgcagt agcagcgagc agcagagtcc gcacgctccg gcgaggggca gaagagcgcg     120

agggagcgcg gggcagcaga agcgagagcc gagcgcggac ccagccagga cccacagccc     180

tccccagctg cccaggaaga gccccagcca tggaacacca gctcctgtgc tgcgaagtgg     240

aaaccatccg ccgcgcgtac cccgatgcca acctcctcaa cgaccgggtg ctgcgggcca     300

tgctgaaggc ggaggagacc tgcgcgccct cggtgtccta cttcaaatgt gtgcagaagg     360

aggtcctgcc gtccatgcgg aagatcgtcg ccacctggat gctggaggtc tgcgaggaac     420

agaagtgcga ggaggaggtc ttcccgctgg ccatgaacta cctggaccgc ttcctgtcgc     480

tggagcccgt gaaaaagagc cgcctgcagc tgctgggggc cacttgcatg ttcgtggcct     540

ctaagatgaa ggagaccatc cccctgacgg ccgagaagct gtgcatctac accgacaact     600

ccatccggcc cgaggagctg ctgcaaatgg agctgctcct ggtgaacaag ctcaagtgga     660

acctggccgc aatgaccccg cacgatttca ttgaacactt cctctccaaa atgccagagg     720

cggaggagaa caaacagatc atccgcaaac acgcgcagac cttcgttgcc ctctgtgcca     780

cagatgtgaa gttcatttcc aatccgccct ccatggtggc agcggggagc gtggtggccg     840

cagtgcaagg cctgaacctg aggagcccca acaacttcct gtcctactac cgcctcacac     900

gcttcctctc cagagtgatc aagtgtgacc cggactgcct ccgggcctgc caggagcaga     960

tcgaagccct gctggagtca agcctgcgcc aggcccagca gaacatggac cccaaggccg    1020

ccgaggagga ggaagaggag gaggaggagg tggacctggc ttgcacaccc accgacgtgc    1080

gggacgtgga catctgaggg cgccaggcag gcgggcgcca ccgccacccg cagcgagggc    1140

ggagccggcc ccaggtgctc ccctgacagt ccctcctctc cggagcattt tgataccaga    1200

agggaaagct tcattctcct tgttgttggt tgtttttttcc tttgctcttt ccccccttcca    1260

tctctgactt aagcaaaaga aaaagattac ccaaaaactg tctttaaaag agagagagag    1320

aaaaaaaaaa tagtatttgc ataaccctga gcggtggggg aggagggttg tgctacagat    1380

gatagaggat tttatacccc aataatcaac tcgtttttat attaatgtac ttgtttctct    1440

gttgtaagaa taggcattaa cacaaaggag gcgtctcggg agaggattag gttccatcct    1500

ttacgtgttt aaaaaaaagc ataaaaacat tttaaaaaca tagaaaaatt cagcaaacca    1560

tttttaaagt agaagagggt tttaggtaga aaaacatatt cttgtgcttt tcctgataaa    1620
```

-continued

```
gcacagctgt agtggggttc taggcatctc tgtactttgc ttgctcatat gcatgtagtc   1680
actttataag tcattgtatg ttattatatt ccgtaggtag atgtgtaacc tcttcacctt   1740
attcatggct gaagtcacct cttggttaca gtagcgtagc gtgcccgtgt gcatgtcctt   1800
tgcgcctgtg accaccaccc caacaaacca tccagtgaca aaccatccag tggaggtttg   1860
tcgggcacca gccagcgtag cagggtcggg aaaggccacc tgtcccactc ctacgatacg   1920
ctactataaa gagaagacga aatagtgaca taatatattc tatttttata ctcttcctat   1980
ttttgtagtg acctgtttat gagatgctgg ttttctaccc aacggccctg cagccagctc   2040
acgtccaggt tcaacccaca gctacttggt ttgtgttctt cttcatattc taaaaccatt   2100
ccatttccaa gcactttcag tccaataggt gtaggaaata gcgctgtttt tgttgtgtgt   2160
gcagggaggg cagttttcta atggaatggt ttgggaatat ccatgtactt gtttgcaagc   2220
aggactttga ggcaagtgtg ggccactgtg gtggcagtgg aggtggggtg tttgggaggc   2280
tgcgtgccag tcaagaagaa aaaggtttgc attctcacat tgccaggatg ataagttcct   2340
ttcctttcct ttaaagaagt tgaagtttag gaatcctttg gtgccaactg gtgtttgaaa   2400
gtagggacct cagaggttta cctagagaac aggtggtttt taagggttat cttagatgtt   2460
tcacaccgga aggtttttaa acactaaaat atataattta tagttaaggc taaaaagtat   2520
atttattgca gaggatgttc ataaggccag tatgatttat aaatgcaatc tccccttgat   2580
ttaaacacac agatacacac acacacacac acacacacaa accttctgcc tttgatgtta   2640
cagatttaat acagtttatt tttaaagata gatcctttta taggtgagaa aaaaacaatc   2700
tggaagaaaa aaaccacaca aagacattga ttcagcctgt ttggcgtttc ccagagtcat   2760
ctgattggac aggcatgggt gcaaggaaaa ttagggtact caacctaagt tcggttccga   2820
tgaattctta tcccctgccc cttcctttaa aaaacttagt gacaaaatag acaatttgca   2880
catcttggct atgtaattct tgtaattttt atttaggaag tgttgaaggg aggtggcaag   2940
agtgtggagg ctgacgtgtg agggaggaca ggcgggagga ggtgtgagga ggaggctccc   3000
gaggggaagg ggcggtgccc acaccgggga caggccgcag ctccattttc ttattgcgct   3060
gctaccgttg acttccaggc acggtttgga aatattcaca tcgcttctgt gtatctcttt   3120
cacattgttt gctgctattg gaggatcagt tttttgtttt acaatgtcat atactgccat   3180
gtactagttt tagttttctc ttagaacatt gtattacaga tgcctttttt gtagtttttt   3240
tttttttat gtgatcaatt ttgacttaat gtgattactg ctctattcca aaaaggttgc   3300
tgtttcacaa tacctcatgc ttcacttagc catggtggac ccagcgggca ggttctgcct   3360
gctttggcgg gcagacacgc gggcgcgatc ccacacaggc tggcgggggc cggccccgag   3420
gccgcgtgcg tgagaaccgc gccggtgtcc ccagagacca ggctgtgtcc ctcttctctt   3480
ccctgcgcct gtgatgctgg gcacttcatc tgatcggggg cgtagcatca tagtagtttt   3540
tacagctgtg ttattctttg cgtgtagcta tggaagttgc ataattatta ttattattat   3600
tataacaagt gtgtcttacg tgccaccacg gcgttgtacc tgtaggactc tcattcggga   3660
tgattggaat agcttctgga atttgttcaa gttttgggta tgtttaatct gttatgtact   3720
agtgttctgt ttgttattgt tttgttaatt acaccataat gctaatttaa agagactcca   3780
aatctcaatg aagccagctc acagtgctgt gtgccccggt cacctagcaa gctgccgaac   3840
caaaagaatt tgcaccccgc tgcgggccca cgtggttggg gccctgccct ggcagggtca   3900
tcctgtgctc ggaggccatc tcgggcacag gcccaccccg ccccacccct ccagaacacg   3960
```

```
gctcacgctt acctcaacca tcctggctgc ggcgtctgtc tgaaccacgc gggggccttg   4020

agggacgctt tgtctgtcgt gatggggcaa gggcacaagt cctggatgtt gtgtgtatcg   4080

agaggccaaa ggctggtggc aagtgcacgg ggcacagcgg agtctgtcct gtgacgcgca   4140

agtctgaggg tctgggcggc gggcggctgg gtctgtgcat ttctggttgc accgcggcgc   4200

ttcccagcac caacatgtaa ccggcatgtt tccagcagaa gacaaaaaga caaacatgaa   4260

agtctagaaa taaaactggt aaaaccccaa aaaaaaaaaa aaaa                    4304


<210> SEQ ID NO 16
<211> LENGTH: 295
<212> TYPE: PRT
<213> ORGANISM: Homo sapiens

<400> SEQUENCE: 16

Met Glu His Gln Leu Leu Cys Cys Glu Val Glu Thr Ile Arg Arg Ala
1               5                   10                  15

Tyr Pro Asp Ala Asn Leu Leu Asn Asp Arg Val Leu Arg Ala Met Leu
            20                  25                  30

Lys Ala Glu Glu Thr Cys Ala Pro Ser Val Ser Tyr Phe Lys Cys Val
        35                  40                  45

Gln Lys Glu Val Leu Pro Ser Met Arg Lys Ile Val Ala Thr Trp Met
    50                  55                  60

Leu Glu Val Cys Glu Glu Gln Lys Cys Glu Glu Glu Val Phe Pro Leu
65                  70                  75                  80

Ala Met Asn Tyr Leu Asp Arg Phe Leu Ser Leu Glu Pro Val Lys Lys
                85                  90                  95

Ser Arg Leu Gln Leu Leu Gly Ala Thr Cys Met Phe Val Ala Ser Lys
            100                 105                 110

Met Lys Glu Thr Ile Pro Leu Thr Ala Glu Lys Leu Cys Ile Tyr Thr
        115                 120                 125

Asp Asn Ser Ile Arg Pro Glu Glu Leu Leu Gln Met Glu Leu Leu Leu
    130                 135                 140

Val Asn Lys Leu Lys Trp Asn Leu Ala Ala Met Thr Pro His Asp Phe
145                 150                 155                 160

Ile Glu His Phe Leu Ser Lys Met Pro Glu Ala Glu Glu Asn Lys Gln
                165                 170                 175

Ile Ile Arg Lys His Ala Gln Thr Phe Val Ala Leu Cys Ala Thr Asp
            180                 185                 190

Val Lys Phe Ile Ser Asn Pro Pro Ser Met Val Ala Ala Gly Ser Val
        195                 200                 205

Val Ala Ala Val Gln Gly Leu Asn Leu Arg Ser Pro Asn Asn Phe Leu
    210                 215                 220

Ser Tyr Tyr Arg Leu Thr Arg Phe Leu Ser Arg Val Ile Lys Cys Asp
225                 230                 235                 240

Pro Asp Cys Leu Arg Ala Cys Gln Glu Gln Ile Glu Ala Leu Leu Glu
                245                 250                 255

Ser Ser Leu Arg Gln Ala Gln Gln Asn Met Asp Pro Lys Ala Ala Glu
            260                 265                 270

Glu Glu Glu Glu Glu Glu Glu Glu Val Asp Leu Ala Cys Thr Pro Thr
        275                 280                 285

Asp Val Arg Asp Val Asp Ile
    290                 295
```

```
<210> SEQ ID NO 17
<211> LENGTH: 1365
<212> TYPE: DNA
<213> ORGANISM: Mus musculus

<400> SEQUENCE: 17

gtgggggtga gggggcctct ctagctcgcg gcctgtgtct atggtctggc ccgaagcgtc     60

cagctgcccg ggaccgatcc ccggtgtatg gcgccgcagg aaccggctcc cgggcccaga    120

taaagggcca cctccagagc tcttagccga gcgtaagatc ccctgcttcg agaatggctg    180

ccactcgata tgaacccgtg gctgaaattg gtgtcggtgc ctatgggacg gtgtacaaag    240

cccgagatcc ccacagtggc cactttgtgg ccctcaagag tgtgagagtt cctaatggag    300

gagcagctgg agggggcctt cccgtcagca cagttcgtga ggtggccttg ttaaggaggc    360

tggaggcctt tgaacatccc aatgttgtac ggctgatgga tgtctgtgct acttcccgaa    420

ctgatcggga catcaaggtc accctagtgt ttgagcatat agaccaggac ctgaggacat    480

acctggacaa agcacctcca ccgggcctgc cggttgagac cattaaggat ctaatgcgtc    540

agtttctaag cggcctggat tttcttcatg caaactgcat tgttcaccgg gacctgaagc    600

cagagaacat tctagtgaca agtaatggga ccgtcaagct ggctgacttt ggcctagcta    660

gaatctacag ctaccagatg gccctcacgc ctgtggtggt tacgctctgg taccgagctc    720

ctgaagttct tctgcagtct acatacgcaa cacccgtgga catgtggagc gttggctgta    780

tctttgcaga gatgttccgt cggaagcctc tcttctgtgg aaactctgaa gccgaccagt    840

tggggaaaat ctttgatctc attggattgc ctccagaaga cgactggcct cgagaggtat    900

ctctacctcg aggagccttt gcccccagag ggcctcggcc agtgcagtca gtggtgccag    960

agatggagga gtctggagcg cagctgctac tggaaatgct gacctttaac ccacataagc   1020

gaatctctgc cttccgagcc ctgcagcact cctacctgca caaggaggaa agcgacgcag   1080

agtgagaaga ggggctgcct ttcccagtct tggtggagaa accctcgctg aagcggcagc   1140

ctctgtttcc ccccaaggct gtggagaatc ctccagtttt ttacagagaa tattttaagc   1200

cttaaataac aagtccccac ctctccttac gaggttcacc cccattaccc tcccctagct   1260

ctacactaaa gggcaggtgt atctgtcttc ttccctccct gatttatact gggatctttt   1320

ttatacagga aaacaagaca agacaaaaaa aaaaaaaaaa aaaaa                   1365


<210> SEQ ID NO 18
<211> LENGTH: 303
<212> TYPE: PRT
<213> ORGANISM: Mus musculus

<400> SEQUENCE: 18

Met Ala Ala Thr Arg Tyr Glu Pro Val Ala Glu Ile Gly Val Gly Ala
1               5                   10                  15

Tyr Gly Thr Val Tyr Lys Ala Arg Asp Pro His Ser Gly His Phe Val
            20                  25                  30

Ala Leu Lys Ser Val Arg Val Pro Asn Gly Gly Ala Ala Gly Gly Gly
        35                  40                  45

Leu Pro Val Ser Thr Val Arg Glu Val Ala Leu Leu Arg Arg Leu Glu
    50                  55                  60

Ala Phe Glu His Pro Asn Val Val Arg Leu Met Asp Val Cys Ala Thr
65                  70                  75                  80

Ser Arg Thr Asp Arg Asp Ile Lys Val Thr Leu Val Phe Glu His Ile
                85                  90                  95
```

-continued

```
Asp Gln Asp Leu Arg Thr Tyr Leu Asp Lys Ala Pro Pro Pro Gly Leu
            100                 105                 110

Pro Val Glu Thr Ile Lys Asp Leu Met Arg Gln Phe Leu Ser Gly Leu
        115                 120                 125

Asp Phe Leu His Ala Asn Cys Ile Val His Arg Asp Leu Lys Pro Glu
    130                 135                 140

Asn Ile Leu Val Thr Ser Asn Gly Thr Val Lys Leu Ala Asp Phe Gly
145                 150                 155                 160

Leu Ala Arg Ile Tyr Ser Tyr Gln Met Ala Leu Thr Pro Val Val Val
                165                 170                 175

Thr Leu Trp Tyr Arg Ala Pro Glu Val Leu Leu Gln Ser Thr Tyr Ala
            180                 185                 190

Thr Pro Val Asp Met Trp Ser Val Gly Cys Ile Phe Ala Glu Met Phe
        195                 200                 205

Arg Arg Lys Pro Leu Phe Cys Gly Asn Ser Glu Ala Asp Gln Leu Gly
    210                 215                 220

Lys Ile Phe Asp Leu Ile Gly Leu Pro Pro Glu Asp Asp Trp Pro Arg
225                 230                 235                 240

Glu Val Ser Leu Pro Arg Gly Ala Phe Ala Pro Arg Gly Pro Arg Pro
                245                 250                 255

Val Gln Ser Val Val Pro Glu Met Glu Glu Ser Gly Ala Gln Leu Leu
            260                 265                 270

Leu Glu Met Leu Thr Phe Asn Pro His Lys Arg Ile Ser Ala Phe Arg
        275                 280                 285

Ala Leu Gln His Ser Tyr Leu His Lys Glu Glu Ser Asp Ala Glu
    290                 295                 300
```

```
<210> SEQ ID NO 19
<211> LENGTH: 3796
<212> TYPE: DNA
<213> ORGANISM: Mus musculus

<400> SEQUENCE: 19

ttttctctgc ccggctttga tctctgctta acaacagtaa cgtcacacgg actacagggg      60

agttttgttg aagttgcaaa gtcctgcagc ctccagaggg ctgtcggcgc agtagcagag     120

agctacagac tccgcgcgct ccggagaccg gcagtacagc gcgaggcagc gcgcgtcagc     180

agccgccacc ggagcccaac cgagaccaca gccctcccca gacggccgcg ccatggaaca     240

ccagctcctg tgctgcgaag tggagaccat ccgccgcgcg taccctgaca ccaatctcct     300

caacgaccgg gtgctgcgag ccatgctcaa gacggaggag acctgtgcgc cctccgtatc     360

ttacttcaag tgcgtgcaga aggagattgt gccatccatg cggaaaatcg tggccacctg     420

gatgctggag gtctgtgagg agcagaagtg cgaagaggag gtcttcccgc tggccatgaa     480

ctacctggac cgcttcctgt ccctggagcc cttgaagaag agccgcctgc agctgctggg     540

ggccacctgc atgttcgtgg cctctaagat gaaggagacc attcccttga ctgccgagaa     600

gttgtgcatc tacactgaca actctatccg gcccgaggag ctgctgcaaa tggaactgct     660

tctggtgaac aagctcaagt ggaacctggc cgccatgact ccccacgatt tcatcgaaca     720

cttcctctcc aaaatgccag aggcggatga gaacaagcag accatccgca agcatgcaca     780

gacctttgtg gccctctgtg ccacagatgt gaagttcatt tccaacccac cctccatggt     840

agctgctggg agcgtggtgg ctgcgatgca aggcctgaac ctgggcagcc ccaacaactt     900

cctctcctgc taccgcacaa cgcactttct ttccagagtc atcaagtgtg acccggactg     960
```

-continued

```
cctccgtgcc tgccaggaac agattgaagc ccttctggag tcaagcctgc gccaggccca   1020
gcagaacgtc gaccccaagg ccactgagga ggagggggaa gtggaggaag aggctggtct   1080
ggcctgcacg cccaccgacg tgcgagatgt ggacatctga gggccaccgg gcaggcggga   1140
gccaccaagt agtggcaccc gcaaagagga aggagccagc ccgggtgctc ctgacgacgt   1200
ccccccttggg gacatgttgt taccagaaga ggaagttttg ttctctttgt tggttgtttt   1260
tccttaatct ttctcctttc tatctgattt aagcaaaaga gaaaaaaata tctgaaagct   1320
gtcttaaaga gagagagaga gagatagaat ctgcatcacc ctgagagtag ggagccaggg   1380
ggtgctacaa aaatagaatt ctgtacccca gtaatcaact agttttctat taatgtgctt   1440
gtctgttcta agagtaggat taacacaggg gaagtcttga gaaggagttt tgattctttt   1500
atatgttttt aaaaaaaagc ttaagaaaca ttgctttaaa aaggaaggaa aaaaaataca   1560
gcaaaccatt gttaaagtag aagagttttt aggttgagaa atgtactctg ctttgctgaa   1620
aagccacagc ttaggccctc agcctcactc cctggcttgc tcagtgccta cagccctgtt   1680
acctgatacc tgtgctttat cccaggggtg ggcagacctc ttaaccttat agatggtcag   1740
tgcgacctct agtggtctca tggcgtgtgg cacaaccccc ctccccaggg ctcagcttaa   1800
tgtgccctct ccccccaaca acctgcaggt tcacagcacc agccacacag cggtagggat   1860
gaaatagtga cataatatat tctatttttg taaccttcct attttgtagc tctgtttaga   1920
gagatgctgg tttttgcctg aaggccctgc agcctgccca catcaggtta aacccacagc   1980
ttttgtgtgt ggtttgtttt gttgtgtttt ctttctctat gttccaaaac cattccattt   2040
caaagcactt ttggtcagct agctggaggc agtgttgctg gtgtgtgttg gggggagggg   2100
ttctaatgga atggatgggg atgtccacac acgcattcag atggctgtac aacaggttgt   2160
agggctggta gtatgaggtg cttgggaagt tttgttgggt caagaagaga gaactctgtt   2220
ctcgcaccac cgggatctgt cctgcaaagt tgaagggatc ctttggtgcc agctggtgtt   2280
tggaagtagg aaccatgatg gcattacctg gacaaggaga ttggggacaa ctcttaagtc   2340
tcacacagga ggcttttaaa cactaaaatg tctaatttat acttaaggct acagaagagt   2400
atttatggga aaggctgccc atgaccagtg tgactcaaag caatgtgatc tcccttgatt   2460
caaacgcaca cctctgccct gctggagaag gtttagggcc atgtctgaga gattggtctt   2520
tcattgggca acgggggggg gggggggtc cttaaaaaaa aaaaaccaca aagacagaga   2580
tttggtctgc ttgactttcc caacccaatt ggccccattg gagagccatc caaactgagg   2640
aaaattaggg gactccaaaa gagtttgatt ctggcacatt cttgccgctg cccccaagtt   2700
aacaacagta ggtaatttgc acacctctgg ctctgtgcct ttctattagg actttttggc   2760
agaaggtgga gagcgggagg cttaagaggg gatgtgaggg aagaggtgaa ggtgggacca   2820
catgggacag gccacggctc ctctcatggc gctgctaccg atgactccca ggatcccaga   2880
cgttcagaac cagattctca ttgctttgta tctttcacgt tgttttcgct gctattggag   2940
ggtcagtttt gttttgtttt gttttacaat gtcagactgc catgttcaag ttttaatttc   3000
ctcatagagt gtatttacag atgccctttt ttgtactttt ttttttaatt gtgatctatt   3060
ttggcttaat gtgattaccg ctgtattcca aaaaaaaaaa aaaaacaggt tcctgttcac   3120
aatacctcat gtatcatcta gccatgcacg agcctggcag gcaggtgggc ggtctgcctc   3180
cagggatcct gggaccctga tggcgatcgt cctgtcatgc tgggcccttc atttgatctg   3240
ggacatagca tcacagcagt cagggcacct ggattgttct gttatcgata ttgtttcttg   3300
tagcggcctg ttgtgcatgc caccatgctg ctggcccggg gggatttgct ctgagtctcc   3360
```

-continued

```
ggtgcatcat ttaatctgtt aggttctagt gttccgtctt gttttgtgtt aattacagca   3420

ttgtgctaat gtaaagactc tgcctttgcg aagccagctg cagtgctgta ggcccccaag   3480

ttccctagca agctgccaaa ccaaaacggg caccaccagc tcagctgagg catcccagcc   3540

aggcaggacc cttgagggcc gctgtatcca tggtgatggg gtgaggtttt ggccaaaagg   3600

ccaaagactg gtggtgggtc cacggaatct gccctgtgac atgaaaggct ttgaggggct   3660

ctggctggtg gccaggttgg ctttttgtat ttctggttga cacaccatgg cgcttcccag   3720

cacagacatg tgaccagcat ggtccaggaa aaaaaaaaag acaaaaaatc tagaaaataa   3780

aattggtaaa atctca                                                    3796


<210> SEQ ID NO 20
<211> LENGTH: 295
<212> TYPE: PRT
<213> ORGANISM: Mus musculus

<400> SEQUENCE: 20

Met Glu His Gln Leu Leu Cys Cys Glu Val Glu Thr Ile Arg Arg Ala
1               5                   10                  15

Tyr Pro Asp Thr Asn Leu Leu Asn Asp Arg Val Leu Arg Ala Met Leu
            20                  25                  30

Lys Thr Glu Glu Thr Cys Ala Pro Ser Val Ser Tyr Phe Lys Cys Val
        35                  40                  45

Gln Lys Glu Ile Val Pro Ser Met Arg Lys Ile Val Ala Thr Trp Met
    50                  55                  60

Leu Glu Val Cys Glu Glu Gln Lys Cys Glu Glu Glu Val Phe Pro Leu
65                  70                  75                  80

Ala Met Asn Tyr Leu Asp Arg Phe Leu Ser Leu Glu Pro Leu Lys Lys
                85                  90                  95

Ser Arg Leu Gln Leu Leu Gly Ala Thr Cys Met Phe Val Ala Ser Lys
            100                 105                 110

Met Lys Glu Thr Ile Pro Leu Thr Ala Glu Lys Leu Cys Ile Tyr Thr
        115                 120                 125

Asp Asn Ser Ile Arg Pro Glu Glu Leu Leu Gln Met Glu Leu Leu Leu
    130                 135                 140

Val Asn Lys Leu Lys Trp Asn Leu Ala Ala Met Thr Pro His Asp Phe
145                 150                 155                 160

Ile Glu His Phe Leu Ser Lys Met Pro Glu Ala Asp Glu Asn Lys Gln
                165                 170                 175

Thr Ile Arg Lys His Ala Gln Thr Phe Val Ala Leu Cys Ala Thr Asp
            180                 185                 190

Val Lys Phe Ile Ser Asn Pro Pro Ser Met Val Ala Ala Gly Ser Val
        195                 200                 205

Val Ala Ala Met Gln Gly Leu Asn Leu Gly Ser Pro Asn Asn Phe Leu
    210                 215                 220

Ser Cys Tyr Arg Thr Thr His Phe Leu Ser Arg Val Ile Lys Cys Asp
225                 230                 235                 240

Pro Asp Cys Leu Arg Ala Cys Gln Glu Gln Ile Glu Ala Leu Leu Glu
                245                 250                 255

Ser Ser Leu Arg Gln Ala Gln Gln Asn Val Asp Pro Lys Ala Thr Glu
            260                 265                 270
```

-continued

```
Glu Glu Gly Glu Val Glu Glu Glu Ala Gly Leu Ala Cys Thr Pro Thr
        275                 280                 285

Asp Val Arg Asp Val Asp Ile
    290                 295
```

METHODS FOR INDUCING CELL DIVISION OF POSTMITOTIC CELLS

CROSS-REFERENCE TO RELATED PATENT APPLICATIONS

This application is a 371 U.S. National Stage Application of International Patent Application No. PCT/US2016/026059 filed Apr. 5, 2016, which claims priority from U.S. Provisional Application 62/144,244, filed Apr. 7, 2015 and U.S. Provisional Application 62/151,321, filed Apr. 22, 2015 which are incorporated herein by reference in their entireties.

BACKGROUND

Regenerative medicine is the replacement, engineering and regeneration of cells, tissues and organs to gain or restore normal cellular function. Much of the regenerative medicine field is concentrated on cellular replacement therapies, particularly stem cell-based therapies. One property of stem cells that makes them uniquely suited for cell-based applications is their ability to proliferate in culture for prolonged periods of time. This proliferative capacity offers a source of starting material from which to derive sufficient numbers of cells for use in cell-based applications. However, as cells age, even many stem cells grown in culture, their proliferative capacity tends to decrease.

In addition, many adult cells, including cardiomyocytes, neurons, and skeletal muscle, are considered to be postmitotic cells that achieve growth through hypertrophy rather than hyperplasia. Postmitotic cells are unable, or have an extremely limited ability, to divide or regenerate. As such, many organs containing these postmitotic cells are severely restricted in their ability to adequately repair or restore function after any significant injury.

It would be beneficial to provide methods for reinitiating postmitotic cell division to regenerate cells and/or replace damaged cells. Such capabilities would be useful for both in vitro culturing and screening as well as in vivo applications for the treatment of numerous diseases and disorders.

SUMMARY

This disclosure is predicated on the discovery that certain agents can induce proliferation and/or cell cycle reentry of postmitotic cells and is directed, in part, to methods of inducing proliferation and/or cell cycle reentry of a postmitotic cell, comprising contacting the postmitotic cell with an effective amount of a composition comprising at least one cyclin-dependent kinase (CDK) and at least one cyclin, or equivalents of each thereof, thereby inducing proliferation and/or cell cycle reentry of the postmitotic cell.

One aspect of the disclosure provides an isolated, proliferative postmitotic cell modified to overexpress at least one CDK and at least one cyclin, or an equivalent of each thereof. Another aspect of the disclosure provides an isolated, proliferative postmitotic cell modified to overexpress CDK1 and CCNB1, or an equivalent of each thereof.

One aspect of the disclosure provides a method for treating a cardiovascular disease comprising administering to a subject in need thereof, an effective amount of a composition that increases the expression of CDK1 and CCNB1, or an equivalent of each thereof.

Another aspect of the disclosure provides a method for treating a neurological disease comprising administering to a subject in need thereof an effective amount of a composition that increases the expression of CDK1 and CCNB1, or equivalents thereof.

In some embodiments, the methods further comprise contacting the cell with an effective amount of a CDK activator, a transforming growth factor β inhibitor, or combinations thereof. In some embodiments, the CDK activator is a CDK1 activator.

In some embodiments, the contacting is conducted in vitro or in vivo.

In some embodiments, the postmitotic cell is selected from the group consisting of a cardiomyocyte, a neural cell, a pancreatic cell, a hair cell, and a skeletal muscle cell. In one preferred embodiment, the proliferative postmitotic cells are proliferative cardiomyocytes. In some embodiments, the proliferative cardiomyocytes are modified to overexpress CDK1 and CCNB1, or equivalents thereof. In other embodiments, the proliferative cardiomyocytes are modified to overexpress CDK4, CCND1, or both. In another preferred embodiment, the proliferative postmitotic cells are proliferative neural cells. In some embodiments, the proliferative neural cells are modified to overexpress CDK1 and CCNB1, or equivalents of each thereof. In other embodiments, the proliferative neural cells are modified to overexpress CDK4, CCND1, or both.

In some embodiments, the composition comprises at least one nucleic acid. In some embodiments, the cyclin-dependent kinase (CDK) and/or the cyclin is encoded by a nucleic acid. In some embodiments, the at least one nucleic acid is a modified mRNA. In other embodiments, the at least one nucleic acid is constitutively expressed.

In some embodiments, the cyclin is selected from the group consisting of cyclinA, cyclinB, cyclinD, and cyclinE. In some embodiments, the cyclinB is cyclinB1 (CCNB1). In some embodiments, the cyclinD is cyclinD1 (CCND1).

In some embodiments, the CDK is selected from the group consisting of CDK1, CDK2, CDK3, CDK4, and CDK6. In one preferred embodiment, the CDK is CDK1. In another preferred embodiment, the CDK is CDK4. In some embodiments, wherein the CDK is constitutively expressed.

In some embodiments, the CDK is CDK1 and the cyclin is CCNB1.

In some embodiments, the composition further comprises CDK4, CCND1, or both.

In some embodiments, the cells are further modified to overexpress CDK4, CCND1, or both.

In some embodiments, the methods comprise administering an effective amount of a composition that increases the expression of CDK4, CCND1, or both.

Another aspect provides a method for treating a cardiovascular disease comprising administering to a subject in need thereof, an effective amount of a composition that increases the expression of CDK1 and CCNB1, or an equivalent of each thereof.

A further aspect provides a method for treating a cardiovascular disease comprising administering to a subject in need thereof, an effective amount of a population of the proliferative postmitotic cells disclosed and described herein.

A further aspect provides a method for treating a neurological disease comprising administering to a subject in need thereof, an effective amount of a population of the proliferative postmitotic cells disclosed and described herein.

In yet a further aspect is provided a method for treating a neurological disease comprising administering to a subject in need thereof an effective amount of a composition that increases the expression of CDK1 and CCNB1, or equivalents thereof.

DETAILED DESCRIPTION

Figure 1:
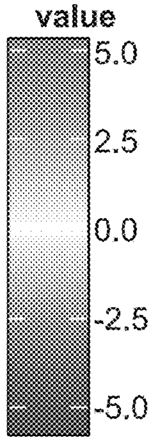
FIG. 1 depicts selected microarray data showing differentially expressed genes related to cell cycle regulation between neonatal (newborn P0) and adult (6 week-old) mouse cardiac cells. Data are represented as $\log_2$, comparing adult and newborn cardiac cells.

It is to be understood that this disclosure is not limited to particular embodiments described, as such may, of course, vary. It is also to be understood that the terminology used herein is for the purpose of describing particular embodiments only, and is not intended to be limiting, since the scope of this disclosure will be limited only by the appended claims.

The detailed description of the disclosure is divided into various sections only for the reader's convenience and disclosure found in any section may be combined with that in another section. Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present invention, the preferred methods and materials are now described. All publications mentioned herein are incorporated by reference to disclose and describe the methods and/or materials in connection with which the publications are cited.

The practice of the present disclosure will employ, unless otherwise indicated, conventional techniques of tissue culture, immunology, molecular biology, cell biology and recombinant DNA, which are within the skill of the art. See, e.g., Sambrook and Russell eds. (2001) Molecular Cloning: A Laboratory Manual, 3rd edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, 5th edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; IRL Press (1986) Immobilized Cells and Enzymes; Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Herzenberg et al. eds (1996) Weir's Handbook of Experimental Immunology; Manipulating the Mouse Embryo: A Laboratory Manual, 3rd edition (2002) Cold Spring Harbor Laboratory Press; Sohail (2004) Gene Silencing by RNA Interference: Technology and Application (CRC Press); Sell (2013) Stem Cells Handbook.

All numerical designations, e.g., pH, temperature, time, concentration, and molecular weight, including ranges, are approximations which are varied (+) or (−) by increments of 0.1 or 1.0, where appropriate. It is to be understood, although not always explicitly stated that all numerical designations are preceded by the term "about." It also is to be understood, although not always explicitly stated, that the reagents described herein are merely exemplary and that equivalents of such are known in the art.

It must be noted that as used herein and in the appended claims, the singular forms "a", "an", and "the" include plural referents unless the context clearly dictates otherwise. Thus, for example, reference to "a cardiomyocyte" includes a plurality of cardiomyocytes.

I. Definitions

As used herein the following terms have the following meanings.

The term "about" when used before a numerical designation, e.g., temperature, time, amount, concentration, and such other, including a range, indicates approximations which may vary by (+) or (−) 10%, 5% or 1%.

"Administration," "administering" and the like, when used in connection with a composition of the disclosure refer both to direct administration, which may be administration to cardiac cells in vitro, administration to cardiac cells in vivo, administration to a subject by a medical professional or by self-administration by the subject and/or to indirect administration, which may be the act of prescribing a composition of the disclosure. When used herein in reference to a cell, refers to introducing a composition to the cell. Typically, an effective amount is administered, which amount can be determined by one of skill in the art. Any method of administration may be used. For example, if a composition of nucleic acids or polypeptides are being administered to a postmitotic cell, the skilled artisan may use transduction, transfection, or the like to administer the nucleic acids or polypeptides to the cell. In addition, small molecules may be administered to the cells by, for example, addition of the small molecules to the cell culture media or injection in vivo to site of cardiac injury. "Administration, "administering" and the like as used herein in reference to a subject in need thereof refers to introducing a composition of proliferation and/or cell cycle reentry factors or proliferative postmitotic cells into a subject in need thereof. Administration to a subject can be achieved by, for example, intravascular injection, intramyocardial delivery, intracranial delivery, and the like.

As used herein, the term "cell cycle reentry" refers to the process of a postmitotic cardiac cell reinitiating at least one stage of the cell cycle, for example, DNA synthesis, mitosis, karyokinesis and cytokinesis.

As used herein the term "cardiac cell" refers to any cell present in the heart that provides a cardiac function, such as heart contraction or blood supply, or otherwise serves to maintain the structure of the heart. Cardiac cells as used herein encompass cells that exist in the epicardium, myocardium or endocardium of the heart. Cardiac cells also include, for example, cardiac muscle cells or cardiomyocytes, and cells of the cardiac vasculatures, such as cells of a coronary artery or vein. Other non-limiting examples of cardiac cells include epithelial cells, endothelial cells, fibroblasts, cardiac stem or progenitor cells, cardiac conducting cells and cardiac pacemaking cells that constitute the cardiac muscle, blood vessels and cardiac cell supporting structure. Cardiac cells may be derived from stem cells, including, for example, embryonic stem cells or induced pluripotent stem cells. The cells can be of any appropriate species, e.g., an animal such as a mammal, e.g., a canine, an equine, a feline, or a human cell.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

As used herein, the term "derived" means differentiated from, reprogrammed from, isolated from or otherwise purified. For example, a cardiomyocyte derived from a fibroblast is a cardiomyocyte that has been reprogrammed in vitro or in vivo from a fibroblast, for example, by overexpressing the GMT cocktail of factors.

As used herein the term "effective amount" and the like in reference to an amount of a composition of proliferation and/or cell cycle reentry factors refers to an amount that is sufficient to induce proliferation and/or cell cycle reentry of cardiac cells (e.g., cardiomyocytes). The cells are contacted with amounts of the composition of proliferation and/or cell cycle reentry factors effective to induce cell cycle reentry and/or proliferation. When used herein in reference to administration to a subject in need thereof, the terms "effective amount" mean an amount of a composition of proliferation and/or cell cycle reentry factors or postmitotic cells induced to proliferate and/or reenter the cell cycle which treat a disease. An effective amount can be administered in one or more administrations, applications or dosages. Such delivery is dependent on a number of variables including the time period which the individual dosage unit is to be used, the bioavailability of the composition, the route of administration, etc. It is understood, however, that specific amounts of the compositions (e.g., of proliferation and/or cell cycle reentry factors or proliferative cardiac cells) for any particular subject depends upon a variety of factors including the activity of the specific agent employed, the age, body weight, general health, sex, and diet of the subject, the time of administration, the rate of excretion, the composition combination, severity of the particular disease being treated and form of administration.

As used herein, the term "equivalents thereof" refers to a polypeptide or nucleic acid sequence that differs from a reference polypeptide or nucleic acid sequence (i.e., a cyclin protein or fragment thereof consistent with embodiments of the present disclosure), but retains essential properties (i.e., biological activity). A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, deletions, additions, fusions and truncations in the polypeptide encoded by the reference sequence. Generally, differences are limited so that the sequences of the reference polypeptide and the variant are closely similar overall and, in many regions, identical.

As used herein, "induce," "inducing" and the like when used in reference to proliferation and/or cell cycle reentry means that postmitotic cells replicate at a faster rate and/or more frequently. In some embodiments of this and other aspects described herein, postmitotic cell proliferation is increased by at least 5%, 10%, 20%, 30%, 40%, 50%, 50%, 70%, 80%, 90%, 1-fold, 1.1-fold, 1.5-fold, 2-fold, 3-fold, 4-fold, 5-fold, 10-fold, 50-fold, 100-fold or more higher relative to an untreated control. The % or fold increase in postmitotic cell proliferation can be determined by measuring the number of replicating postmitotic cells following administration of a composition capable of stimulating proliferation and/or cell cycle reentry, as described herein, relative to a control where the postmitotic cells are not in contact with the composition. Increase in proliferation can also be based on ratios of replicating cells to total number of cells in the respective treated and untreated control. In some embodiments, total number of cells in the treated and untreated controls is used to determine the proliferation. Cell proliferation can be determined using the BrdU incorporation method (and similar methods, for example, EdU incorporation) described in Yamagishi et al. (2001) *Dev Biol* 239: 190-203, the content of which is incorporated herein by reference. Other methods of detecting cell proliferation include use of antibodies to Ki67 for G1, S, G2 and M-phase and phospho histone 3 (PHH3) for M-phase of the cell cycle.

As used herein the term "isolated" with reference to a cell, refers to a cell that is in an environment different from that in which the cell naturally occurs, e.g., where the cell naturally occurs in a multicellular organism, and the cell is removed from the multicellular organism, the cell is "isolated." An isolated modified postmitotic cell can be present in a mixed population of genetically modified postmitotic cells, or in a mixed population comprising genetically modified postmitotic cells and postmitotic cells that are not genetically modified. For example, an isolated genetically modified postmitotic cell can be present in a mixed population of genetically modified postmitotic cells in vitro, or in a mixed in vitro population comprising genetically modified postmitotic cells and postmitotic cells that are not genetically modified. The term "isolated" as used herein with respect to nucleic acids, such as DNA or RNA, refers to molecules separated from other DNAs or RNAs, respectively that are present in the natural source of the macromolecule. The term "isolated nucleic acid" is meant to include nucleic acid fragments which are not naturally occurring as fragments and would not be found in the natural state. The term "isolated" is also used herein to refer to polypeptides, proteins that are isolated from other cellular proteins and is meant to encompass both purified and recombinant polypeptides. In other embodiments, the term "isolated" means separated from constituents, cellular and otherwise, in which the cell, tissue, polynucleotide, peptide, polypeptide, protein, antibody or fragment(s) thereof, which are normally associated in nature. For example, an isolated cell is a cell that is separated form tissue or cells of dissimilar phenotype or genotype. As is apparent to those of skill in the art, a non-naturally occurring polynucleotide, peptide, polypeptide, protein, does not require "isolation" to distinguish it from its naturally occurring counterpart.

As used herein, the term "nucleic acid" and "polynucleotide" are used interchangeably and refer to a polymeric form of nucleotides of any length, either deoxyribonucleotides or ribonucleotides, or analogs thereof. Non-limiting examples of polynucleotides include linear and circular nucleic acids, messenger RNA (mRNA), cDNA, recombinant polynucleotides, vectors, probes, and primers.

The terms "polypeptide," "peptide," and "protein," are used interchangeably herein and refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues, immunologically tagged proteins, and the like.

The term "proliferation" as used herein refers to growth and division of postmitotic cells. In some embodiments, the term "proliferation" is used herein in reference to postmitotic cells refers to a group of postmitotic cells that increase in number over a period of time. The term "proliferation and/or cell cycle reentry factors" refers to any agent that can induce, alone or in combination with additional agents, a postmitotic cell to undergo or enter DNA synthesis, mitosis, karyokinesis and/or cytokinesis.

As used herein, the term "progenitor cell" refers to a cell that is committed to differentiate into a specific type of cell or to form a specific type of tissue. A progenitor cell, like a stem cell, can further differentiate into one or more kinds of cells, hut is more mature than a stem cell such that it has a more limited/restricted differentiation capacity.

As used herein the term "subject" refers to a mammal, preferably a human, but includes and is not limited to non-human primates, murines (i.e., mice and rats), canines, felines, equines, bovines, ovines, porcines, caprines, etc. In some embodiments, the subject is a human subject.

"Treatment," "treating," and "treat" are defined as acting upon a disease, disorder, or condition with an agent to reduce or ameliorate harmful or any other undesired effects of the disease, disorder, or condition and/or its symptoms. "Treatment," as used herein, covers the treatment of a subject in need thereof, and includes treatment of cardiovascular disease (e.g., heart failure, myocardial ischemia, hypoxia, stroke, myocardial infarction and chronic ischemic heart disease), a neurological disease (e.g., epilepsy, Alzheimer disease and other dementias, cerebrovascular diseases including stroke, migraine and other headache disorders, multiple sclerosis, Parkinson's disease, neuroinfections, brain tumors, traumatic disorders), diabetes, or hearing impairment or loss. "Treating" or "treatment of" a condition or subject in need thereof refers to (1) taking steps to obtain beneficial or desired results, including clinical results such as the reduction of symptoms; (2) preventing the disease, for example, causing the clinical symptoms of the disease not to develop in a patient that may be predisposed to the disease but does not yet experience or display symptoms of the disease; (3) inhibiting the disease, for example, arresting or reducing the development of the disease or its clinical symptoms; (4) relieving the disease, for example, causing regression of the disease or its clinical symptoms; or (5) delaying the disease. For one purpose of this invention, beneficial or desired clinical results include, but are not limited to, inducing proliferation of a cardiac cell, inducing cell cycle reentry, and/or promoting myocardial regeneration. For another purpose of this invention, beneficial or desired clinical results include, but are not limited to, inducing proliferation of a neuron, inducing cell cycle reentry, and/or promoting neuronal regeneration.

The term "vector" is used herein to refer to a nucleic acid molecule capable of transferring or transporting another nucleic acid molecule. The transferred nucleic acid is generally linked to, for example, the vector nucleic acid molecule. A vector may include sequences that direct autonomous replication in a cell, or may include sequences sufficient to allow integration into cardiac cell DNA. Useful vectors include, for example, plasmids (e.g., DNA plasmids or RNA plasmids), transposons, cosmids, bacterial or yeast artificial chromosomes and viral vectors. Useful viral vectors include, for example, adenoviruses, retroviruses, particularly replication defective retroviruses, and lentiviruses.

As used herein, the term "viral vector" refers either to a nucleic acid molecule that includes virus-derived nucleic acid elements that typically facilitate transfer of the nucleic acid molecule or integration into the genome of a cell or to a viral particle that mediates nucleic acid transfer. Viral particles will typically include various viral components and sometimes also cell components in addition to nucleic acid(s). The term "viral vector" may also refer either to a virus or viral particle capable of transferring a nucleic acid into a cell or to the transferred nucleic acid itself. Viral vectors and transfer plasmids contain structural and/or function genetic elements that are primarily derived from a virus. The viral vector may be a hybrid vector, LTR or other nucleic acid containing both retroviral (e.g., lentiviral) sequences and non-retroviral viral sequences. A hybrid vector may refer to a vector or transfer plasmid comprising retroviral (e.g., lentiviral) sequences for reverse transcription, replication, integration and/or packaging.

The term "adenoviral vector" as used herein, refers to any adenoviral vector that includes exogenous DNA which encodes a polypeptide inserted into its genome. The vector must be capable of replicating and being packaged when any deficient essential genes are provided in trans. An adenoviral vector desirably contains at least a portion of each terminal repeat required to support the replication of the viral DNA, preferably at least about 90% of the full ITR sequence, and the DNA required to encapsidate the genome into a viral capsid. Many suitable adenoviral vectors have been described in the art. U.S. Pat. No. 6,440,944; see U.S. Pat. No. 6,040,174 (replication defective E1 deleted vectors and specialized packaging cell lines). In some embodiments, the adenoviral expression vector is one that is replication defective in normal cells. In other embodiments, an adenoviral vector refers to an adeno-associated viral (AVV) vector. In some embodiments, the adenoviral expression vector is pseudotyped to enhance targeting.

The term "retroviral vector" refers to a viral vector or plasmid containing structural and functional genetic elements, or portions thereof, that are primarily derived from a retrovirus.

The term "lentiviral vector" refers to a viral vector or plasmid containing structural and functional genetic elements, or portions thereof, that are primarily derived from a lentivirus.

The terms "lentiviral vector" or "lentiviral expression vector" may be used to refer to lentiviral transfer plasmids and/or infectious lentiviral particles. It is understood that nucleic acid sequence elements such as cloning sites, promoters, regulatory elements, heterologous nucleic acids, etc. are present in RNA form in the lentiviral particles of the invention and are present in DNA form in the DNA plasmids of the invention.

The term "genetic modification" refers to a permanent or transient genetic change induced in a cell following introduction of new nucleic acid (i.e., nucleic acid exogenous to the cell). Genetic change can be accomplished by incorporation of the new nucleic acid into the genome of the cardiac cell, or by transient or stable maintenance of the new nucleic acid as an extrachromosomal element. Where the cell is a eukaryotic cell, a permanent genetic change can be achieved by introduction of the nucleic acid into the genome of the cell. Suitable methods of genetic modification include viral infection, transfection, conjugation, protoplast fusion, electroporation, particle gun technology, calcium phosphate precipitation, direct microinjection, and the like.

The terms "regenerate," "regeneration" and the like as used herein in the context of injured cells or tissue shall be given their ordinary meanings and shall also refer to the process of growing and/or developing new cells or tissue (e.g., cardiac) in tissue that has been injured, for example, injured due to ischemia, infarction, reperfusion, or other disease. In some embodiments, tissue regeneration comprises activation and/or enhancement of cell proliferation. In some embodiments, tissue regeneration comprises activation and/or enhancement of cell migration.

The term "stem cells" refer to cells that have the capacity to self-renew and to generate differentiated progeny. The term "pluripotent stem cells" refers to stem cells that can give rise to cells of all three germ layers (endoderm, mesoderm and ectoderm), but do not have the capacity to give rise to a complete organism. In some embodiments, the compositions for inducing proliferation and/or cell cycle reentry can be used on a population of stem cells to increase proliferation rates. In other embodiments, the compositions do not increase proliferation rates of stem cells.

The term "induced pluripotent stem cells" shall be given its ordinary meaning and shall also refer to differentiated mammalian somatic cells (e.g., adult somatic cells, such as skin) that have been reprogrammed to exhibit at least one characteristic of pluripotency. See, for example, Takahashi et al. (2007) *Cell* 131(5):861-872, Kim et al. (2011) *Proc. Natl. Acad. Sci.* 108(19): 7838-7843, Sell (2013) Stem Cells Handbook.

The term "postmitotic cell" is a cell that does not exhibit mitosis or cellular division. Non-limiting examples of postmitotic cells include differentiated cells that comprise the brain (e.g., neurons), heart (e.g., cardiomyocytes) and skeletal muscle. As used herein, the term "proliferative postmitotic cell" refers to a postmitotic cell that has been induced to proliferate and/or reenter the cell cycle. For example, a proliferative cardiomyocyte is a cardiomyocyte, having none or limited proliferative capacity, that has been induced to proliferate and/or reenter the cell cycle. A proliferative postmitotic cell (e.g., proliferative cardiomyocyte) may undergo any number of cell divisions, for example, one, two, three, four, five, six, seven, eight, nine, ten, fifteen, twenty, or more cell divisions before again exiting the cell cycle and returning to a postmitotic state.

II. Methods of Inducing Proliferation and/or Cell Cycle Reentry of Postmitotic Cells As will be apparent to the skilled artisan upon reading this disclosure, the present disclosure provides methods of inducing proliferation and/or cell cycle reentry of a postmitotic cell, the methods comprising, or alternatively consisting essentially of, or yet further consisting of, contacting the postmitotic cell with an effective amount of a composition in an amount effective to stimulate proliferation and/or cell cycle reentry of the postmitotic cell (e.g., one or more proliferation and/or cell cycle reentry factors). The cell can be from any species, an animal, a mammal, e.g., a canine, a feline, a murine, a rat, or a human cell.

In some embodiments, the contacting is conducted in vitro or in vivo.

In one aspect this disclosure provides, methods of inducing proliferation and/or cell cycle reentry of a postmitotic cell (e.g., a postmitotic cardiomyocyte), the method comprising, or alternatively consisting essentially of, or yet further consisting of, contacting the postmitotic cell with an effective amount of a composition to stimulate proliferation and/or cell cycle reentry of the postmitotic cell. The composition is capable of increasing expression of at least one gene encoding a cyclin-dependent kinase (CDK), a cyclin, an aurora kinase, actin binding protein anillin (ANLN), a cell division cycle (CDC) protein, a cadherin, a COPS signalosome complex subunit, a cullin, a GTPase-activating protein, a protein regulator of cytokinesis and/or WNT1-inducible signaling pathway protein or equivalents thereof. The cell can be from any species, an animal, a mammal, e.g., a canine, a feline, a murine, a rat, or a human cell.

In some embodiments, the postmitotic cell is selected from the group consisting of a cardiomyocyte, a neural cell, a pancreatic cell, a hair cell, and a skeletal muscle cell.

Cardiac Cells

The cardiac cells of the present disclosure include any cells present in the heart that provide a cardiac function. Cardiac cells encompass cells that exist in the epicardium, myocardium or endocardium of the heart. Cardiac cells also include, for example, cardiac muscle cells or cardiomyocytes, and cells of the cardiac vasculatures, such as cells of a coronary artery or vein. Other non-limiting examples of cardiac cells include epithelial cells, endothelial cells, fibroblasts, cardiac stem or progenitor cells, cardiac conducting cells and cardiac pacemaking cells that constitute the cardiac muscle, blood vessels and cardiac cell supporting structure.

Cardiac cells can be derived from cardiac or non-cardiac cells. Cardiac cells can be from or derived from any of a variety of tissue sources. For example, stem cells, cardiac fibroblasts, foreskin fibroblast, dermal fibroblasts, lung fibroblasts, etc. The cardiac cells can be embryonic, fetal, or post-natal (e.g., adult) cardiac cells. In a preferred embodiment, the cardiac cells are adult cardiac cells. In some embodiments, the cardiac cells are derived from stem cells.

Non-cardiac cells can be differentiated into cardiac cells in vitro or in vivo using any method available to one of skill in the art. For example, see methods described in leda M. et al. (2010) *Cell* 142(3):375-386 and Kwon C. et al. *Proc. Natl. Acad. Sci.* (2007) 104(26):10894-10899.

In certain embodiments, the cardiac cells are cardiomyocytes. In certain embodiments, the cardiomyocytes are adult postmitotic cardiomyocytes. In another aspect, the adult postmitotic cardiomyocytes have no or low proliferative capacity. In some embodiments, the cardiomyocyte is a mononucleated cell. In other embodiments, the cardiomyocyte is multi-nucleated.

Where the cells for modification are a population of cardiac cells, the population of cells is composed of at least about 60% cardiac cells, at least about 65% cardiac cells, at least about 70% cardiac cells, at least about 75% cardiac cells, at least about 80% cardiac cells, at least about 85% cardiac cells, at least about 90% cardiac cells, at least about 95% cardiac cells, at least about 98% cardiac cells, at least about 99% cardiac cells, or greater than 99% cardiac cells.

Neural Cells

The neural cells of the present disclosure include any cells present in the nervous system that provide a neural function. Neural cells encompass cells that exist in the brain (e.g., cerebrum, cerebellum, and brainstem) and spinal cord, as well as cells of the peripheral nervous system, including sensory neurons. Neural cells also include, for example, neurons, oligodendrocytes, and astrocytes. Non-limiting examples of neurons include, motor neurons, pyramidal neuron, purkinje cells, retinal neuron, olfactory neuron, touch and pain sensory neuron, and amacrine cells.

Neural cells can be derived from neural or non-neural cells. Neural cells can be from or derived from any of a variety of tissue sources. For example, stem cells, fibroblasts, foreskin fibroblast, dermal fibroblasts, lung fibroblasts, etc. The neural cells can be embryonic, fetal, or post-natal (e.g., adult) neural cells. In a preferred embodiment, the neural cells are adult neural cells. In some embodiments, the neural cells are derived from stem cells (e.g., neural stem cells).

Non-neural cells can be differentiated into neural cells in vitro or in vivo using any method available to one of skill in the art. For example, see methods described in Guo et al. (2014) *Cell Stem Cell* 14(2):188-202; Keirstead et al. (2005) *J Neurosci.* 25(19):4694-4705; Kim et al. (2012) *Curr Opinion Neurobiol.* 22(5):778-784.

In certain embodiments, the neural cells are neurons. In certain embodiments, the neurons are adult postmitotic neurons. In preferred embodiments, the adult postmitotic neurons have no or low proliferative capacity.

Where the cells for modification are a population of neural cells, the population of cells is composed of at least about 60% neural cells, at least about 65% neural cells, at least about 70% neural cells, at least about 75% neural cells, at least about 80% neural cells, at least about 85% neural cells, at least about 90% neural cells, at least about 95% neural cells, at least about 98% neural cells, at least about 99% neural cells, or greater than 99% neural cells.

Pancreatic Cells

The pancreatic cells of the present disclosure include any cells present in the pancreas that provide a pancreatic function. Examples of pancreatic cells include cells within the islets of Langerhans (e.g., alpha cells, beta cells, delta cells, PP cells and epsilon cells) and acinar cells. In some embodiments, the pancreatic cells are pancreatic progenitor cells.

Pancreatic cells can be derived from pancreatic or non-pancreatic cells. Pancreatic cells can be from or derived from any of a variety of tissue sources. For example, stem cells, fibroblasts, foreskin fibroblast, dermal fibroblasts, lung fibroblasts, etc. The pancreatic cells can be embryonic, fetal, or post-natal (e.g., adult) pancreatic cells. In a preferred embodiment, the pancreatic cells are adult pancreatic cells. In some embodiments, the pancreatic cells are derived from stem cells.

Non-pancreatic cells can be differentiated into pancreatic cells in vitro or in vivo using any method available to one of skill in the art. For example, see methods described in D'Amour et al. (2005) *Nature Biotech.* 23:1534-1541 and U.S. Pat. No. 8,633,024.

In certain embodiments, the pancreatic cells are beta cells or beta cell precursors. In certain embodiments, the beta cells are adult beta cells. In preferred embodiments, the adult postmitotic pancreatic cells have no or low proliferative capacity.

Where the cells for modification are a population of pancreatic cells, the population of cells is composed of at least about 60% pancreatic cells, at least about 65% pancreatic cells, at least about 70% pancreatic cells, at least about 75% pancreatic cells, at least about 80% pancreatic cells, at least about 85% pancreatic cells, at least about 90% pancreatic cells, at least about 95% pancreatic cells, at least about 98% pancreatic cells, at least about 99% pancreatic cells, or greater than 99% pancreatic cells.

Hair Cells

Hair cells of the present disclosure include inner hair cells (stereocilia) and outer hair cells. Hair cells can be derived from hair or non-hair cells. Hair cells can be from or derived from any of a variety of tissue sources. For example, stem cells, fibroblasts, foreskin fibroblast, dermal fibroblasts, lung fibroblasts, etc. The hair cells can be embryonic, fetal, or post-natal (e.g., adult) hair cells. In a preferred embodiment, the hair cells are adult hair cells. In some embodiments, the hair cells are derived from stem cells. Non-hair cells can be differentiated into hair cells in vitro or in vivo using any method available to one of skill in the art. For example, see methods described in Mohammad et al. (2014) *Stem Cells and Dev.* 23(11):1275-1284. In preferred embodiments, the adult postmitotic hair cells have no or low proliferative capacity.

Where the cells for modification are a population of hair cells, the population of cells is composed of at least about 60% hair cells, at least about 65% hair cells, at least about 70% hair cells, at least about 75% hair cells, at least about 80% hair cells, at least about 85% hair cells, at least about 90% hair cells, at least about 95% hair cells, at least about 98% hair cells, at least about 99% hair cells, or greater than 99% hair cells.

Skeletal Muscle Cells

Skeletal muscle cells of the present disclosure refer to cells of the muscle fibers. Skeletal muscle cells can be derived from skeletal muscle cells or non-skeletal muscle cells. Skeletal muscle cells can be from or derived from any of a variety of tissue sources. For example, stem cells, fibroblasts, foreskin fibroblast, dermal fibroblasts, lung fibroblasts, etc. The skeletal muscle cells can be embryonic, fetal, or post-natal (e.g., adult) skeletal muscle cells. In a preferred embodiment, the skeletal muscle cells are adult skeletal muscle cells. In some embodiments, the skeletal muscle cells are derived from stem cells. Non-skeletal muscle cells can be differentiated into muscle cells in vitro or in vivo using any method available to one of skill in the art. For example, see methods described in Salani et al. (2012) *J Cell Mol. Med.* 16(7):1353-1364. In preferred embodiments, the adult postmitotic skeletal muscle cells have no or low proliferative capacity.

Where the cells for modification are a population of skeletal muscle cells, the population of cells is composed of at least about 60% skeletal muscle cells, at least about 65% skeletal muscle cells, at least about 70% skeletal muscle cells, at least about 75% skeletal muscle cells, at least about 80% skeletal muscle cells, at least about 85% skeletal muscle cells, at least about 90% skeletal muscle cells, at least about 95% skeletal muscle cells, at least about 98% skeletal muscle cells, at least about 99% skeletal muscle cells, or greater than 99% skeletal muscle cells.

In some embodiments the postmitotic cells are endogenous postmitotic cells such that the cells are within the subject and the methods of inducing proliferation and/or cell cycle reentry are by in vivo modification. In other embodiments, the postmitotic cells are exogenous and the postmitotic cells are modified in vitro.

The postmitotic cells that are induced to proliferate and/or reenter the cell cycle can be from any of a variety of sources. Mammalian postmitotic cells (e.g., human, canine, feline or murine) can be used. In some embodiments, the postmitotic cells are mammalian cardiomyocytes. In some embodiments, the postmitotic cells can be derived from stem cells (e.g., pluripotent stem cells, induced pluripotent stem cells, reprogrammed cardiac cells, cardiac stem cells, neural stem cells). In some embodiments, embryonic stem cells are expressly excluded.

The postmitotic cells can be obtained from a living subject. The cells can be obtained from tissue taken from a living subject. The cells can be obtained from a recently deceased subject who is considered a suitable tissue donor. In some embodiments, the subject is screened for various genetic disorders, viral infections, etc. to determine whether the subject is a suitable source of cells. In general, a cell that is suitable for use in the present invention is non-transformed (e.g., exhibits normal cell proliferation) and is otherwise normal (e.g., exhibits normal karyotype).

Postmitotic cells can be derived from tissue of a non-embryonic subject, a neonatal infant, a child or an adult. Postmitotic cells can be derived from neonatal or post-natal tissue collected from a subject within the period from birth, including cesarean birth, to death. For example, the postmitotic cell induced to proliferate and/or reenter the cell cycle can be from a subject who is greater than about 10 minutes old, greater than about 1 hour old, greater than about 1 day old, greater than about 1 month old, greater than about 2 months old, greater than about 6 months old, greater than about 1 year old, greater than about 2 years old, greater than about 5 years old, greater than about 10 years old, greater than about 15 years old, greater than about 18 years old, greater than about 25 years old, greater than about 35 years old, >45 years old, >55 years old, >65 years old, >80 years old, <80 years old, <70 years old, <60 years old, <50 years old, <40 years old, <30 years old, <20 years old or <10 years old.

Methods of isolating postmitotic cells from tissues are known in the art, and any known method can be used. As a non-limiting example, adult cardiac cells can be obtained from human heart atrial biopsy specimens obtained from patients undergoing cardiac surgery. Cardiac tissue can be minced and digested with collagenase and cardiac stem/progenitor cells expanded in c-kit+ progenitor cell expansion media using the methods of Choi et al. (2013) *Transplantation Proceedings* 45:420-426. In addition, cardiac fibroblasts can be obtained using the methods of Ieda et al. (2009) *Dev. Cell* 16(2):233-244. Foreskin fibroblasts can be obtained from foreskin tissue of a male individual. The fibroblasts can be obtained by mincing the foreskin tissue, then dissociating the tissue to single cells. Foreskin cell clumps can be dissociated by any means known in the art including physical de-clumping or enzymatic digestion using, for example trypsin.

Postmitotic cells (e.g., cardiomyocytes, neural cells, pancreatic cells, hair cells, skeletal muscle cells) can be genetically or non-genetically modified with one or more nucleic acids comprising nucleotide sequences encoding cell cycle regulating genes, for example, a cyclin-dependent kinase, a cyclin and/or an aurora kinase, or can be modified by introducing polypeptides. As discussed below, a postmitotic cell can be induced to proliferate or reenter the cell cycle by overexpressing nucleic acids comprising nucleotide sequences encoding a cyclin-dependent kinase, a cyclin and/or an aurora kinase (e.g., CDK1, CCNB1 and AURKB), or by introducing polypeptides comprising a cyclin-dependent kinase, a cyclin and/or an aurora kinase amino acid sequences (e.g., CDK1, CCNB1 and AURKB), or still further modified by introducing chemicals (e.g., small molecules) to induce expression of endogenous a cyclin-dependent kinase, a cyclin, and/or an aurora kinase (e.g., CDK1, CCNB1 and AURKB). Amino acid sequences for cyclin-dependent kinases, cyclins and aurora kinases are known in the art. Nucleotide sequences encoding cyclin-dependent kinases, cyclins and aurora kinases are known in the art.

Additionally, a postmitotic cell can be induced to proliferate or reenter the cell cycle by overexpressing nucleic acids comprising nucleotide sequences encoding at least one cyclin-dependent kinase (CDK) and at least one cyclin, or equivalents of each thereof (e.g., CDK1 and CCNB1) or by introducing polypeptides comprising at least one cyclin-dependent kinase and at least one cyclin amino acid sequences (e.g., CDK1 and CCNB1), or still further modified by introducing chemicals (e.g., small molecules) to induce expression of endogenous a cyclin-dependent kinase and/or a cyclin.

In some embodiments, the postmitotic cell is contacted with an effective amount of a CDK activator, a transforming growth factor β inhibitor, or combinations thereof. In some embodiments, the CDK activator is a CDK1 activator. An example of a CDK1 activator is the Weel inhibitor MK1775. MK1775 is known to indirectly induce CDK1 expression. A transforming growth factor beta (TGF-β) inhibitor is a compound that inhibits TGF-β signal transduction by inhibiting any of the factors constituting the TGF-β signal transduction system pathway, such as TGF-β ligand, TGF-β Type I receptors, TGF-β Type II receptors, TGF-β Type III receptors (β-glycan and endoglin), soluble forms of the TGF-β receptors, Smad proteins, antibodies against receptors and ligands implicated in the signaling pathway, nucleic acid based molecules (e.g., antisense, siRNA, aptamers and ribozymes) targeting the pathway members, or a combination thereof.

In some embodiments, the TGF-β inhibitor is selected from the group consisting of SB431542, D4476, LDN-193189, dexamethasone and LY364947. TGF-β inhibitors also may be referred to in the art as anti-TGF-β compounds. Non-limiting examples of anti-TGF-β compounds include, antibodies (e.g., Fresolumimab/GC1008 (Genzyme, Cambridge, Mass., USA), PF-03446962 (Pfizer, New York, N.Y., USA)), antisense oligonucleotides (ASO) (e.g., Trabedersen (AP12009) (Isarna Therapeutics, New York, N.Y., USA)), receptor kinase inhibitors (e.g., LY2157299 (Eli Lilly, Indianapolis, Ind., USA), and combined TGF-β ASO with a vaccine (e.g., Lucanix™ (Belagenpumatucel-L) (Nova Rx Corp, San Diego, Calif., USA), and TGF-$\beta_2$ ASO+GMCSF expression vector (Mary Crowley Medical Research Centre, Dallas, Tex., USA)). It is contemplated that addition of a TGF-β inhibitor to the composition acts to improve cell survival.

Culture Conditions

The cells of the present disclosure can be cultured under any conditions known to one of skill in the art. In some embodiments, the cells are cultured in conditions of 1-20% oxygen ($O_2$) and 5% carbon dioxide ($CO_2$). In some embodiments, the cells of the present disclosure are cultured under hypoxic conditions (e.g., in the presence of less than 10% $O_2$). In some embodiments, the cells of the present disclosure are cultured at about 37° C. In some embodiments, the cells of the present disclosure can be cultured at about 37° C., 5% $CO_2$ and 10-20% $O_2$. In some embodiments, the cells are cultured in hypoxic conditions for a period of time. For example, the cells may be cultured under normoxic conditions (~20% $O_2$) for a period of time and then switched to hypoxic conditions, for example ~5% $O_2$.

In Vitro Modification

In one aspect, the methods and compositions of the present disclosure induce proliferation and/or cell cycle reentry of a postmitotic cell, by contacting the postmitotic cell with an effective amount of a composition comprising at least one cyclin-dependent kinase (CDK) and at least one cyclin, or equivalents of each thereof, thereby inducing proliferation and/or cell cycle reentry of the postmitotic cell.

In one aspect, the methods and compositions of the present disclosure induce postmitotic cell proliferation and/or cell cycle reentry by administering to a postmitotic cell a composition capable of stimulating proliferation and/or cell cycle reentry (e.g., a composition capable of increasing expression of a cyclin-dependent kinase, a cyclin, and/or an aurora kinase).

In some embodiments, the compositions induce the postmitotic cells to divide in vitro over a period of at least one day, of at least two days, of at least three days, of at least four days, of at least five days, of at least six days, of at least seven days, of at least eight days, or of at least nine days in vitro. In one embodiment, at least about 0.1% of the postmitotic cells are induced to proliferate and/or reenter the cell cycle. In another embodiment at least about 0.2%, 0.3%, 0.4%, 0.5%, 0.6%, 0.7%, 0.8%, 0.9%, 1%, 2%, 5%, 10%, 15% of the postmitotic cells are induced to proliferate and/or reenter the cell cycle.

In some embodiments, a composition to induce postmitotic cell proliferation and/or cell cycle reentry is administered to the postmitotic cell in vitro or ex vivo. The postmitotic cells are modified (genetically or non-genetically) to stimulate proliferation and/or cell cycle reentry in vitro or ex vivo. Once at least a portion of the postmitotic cells have at least begun to proliferate and or reenter the cell cycle in vitro or ex vivo, the postmitotic cells can be introduced into a subject. In some embodiments, the postmitotic cells of the present disclosure can be used as a utility in research and drug development. Postmitotic cells may be cultured by a variety of methods commonly known to those of skill in the art.

The advantage of in vitro or ex vivo modification of postmitotic cells is the ability to easily identify cells suitable for implantation or for discrimination of cells that are damaged or are not proliferating and/or have not reentered the cell cycle. In vitro or ex vivo modification allows postmitotic cells that have been modified to be purified or isolated from those postmitotic cells that have not been modified.

Postmitotic cells may be modified by a variety of mechanisms commonly known to those of skill in the art. Viral constructs can be delivered through the production of a virus in a suitable host. Virus is then harvested from the host cell and contacted with the postmitotic cell. Viral and non-viral vectors capable of expressing genes of interest can be delivered to a postmitotic cell via DNA/liposome complexes, micelles and targeted viral protein-DNA complexes. Liposomes that also comprise a targeting antibody or fragment thereof can be used in the methods of this invention. In addition to the delivery of polynucleotides to a postmitotic cell or cell population, direct introduction of proteins described herein to the postmitotic cell or cell population can be done by the non-limiting technique of protein transfection, alternatively culturing conditions that can enhance expression and/or promote activity of the proteins of this invention are other non-limiting techniques.

Other methods of delivering vectors encoding genes of the current invention include, but are not limited to, calcium phosphate transfection, DEAE-dextran transfection, electroporation, microinjection, protoplast fusion, or liposome-mediated transfection. The host cells that are transfected with the vectors of this disclosure may include, but are not limited to, *E. coli* or other bacteria, yeast, fungi, or cells derived from mice, humans, or other animals (e.g., mammals). In vitro expression of a protein, fusion, polypeptide fragment or mutant encoded by cloned DNA may also be used. Those skilled in the art of molecular biology will understand that a wide variety of expression systems and purification systems may be used to produce recombinant proteins and fragments thereof.

In Vivo Modification

In some embodiments, the present disclosure provides methods of inducing postmitotic cell proliferation and/or cell cycle reentry in vivo. In some embodiments, the compositions induce the postmitotic cells to divide in vivo over a period of at least one day, of at least two days, of at least three days, of at least four days, of at least five days, of at least six days, of at least seven days, of at least eight days, or of at least nine days in vivo. In one embodiment, at least about 0.1% of the postmitotic cells are induced to proliferate and/or reenter the cell cycle. In another embodiment at least about 0.2%, 0.3%, 0.4%, 0.5%, 0.6%, 0.7%, 0.8%, 0.9%, 1%, 2%, 5%, 10%, 15% of the postmitotic cells are induced to proliferate and/or reenter the cell cycle.

In some embodiments, a postmitotic cell is modified (e.g., genetically or non-genetically) in vivo with an effective amount of a composition to stimulate proliferation and/or cell cycle reentry of the postmitotic cell (e.g., cardiomyocytes), wherein the composition is capable of increasing expression of a cyclin-dependent kinase, a cyclin, and an aurora kinase, or equivalents thereof and wherein the composition is administered to a subject in vivo. In other embodiments, a postmitotic cell is modified (e.g., genetically or non-genetically) in vivo with an effective amount of a composition comprising at least one cyclin-dependent kinase (CDK) and at least one cyclin, or equivalents of each thereof, thereby inducing proliferation and/or cell cycle reentry of the postmitotic cell in vivo. The compositions described herein can contain nucleic acids, polypeptides, and/or combinations thereof.

For in vivo delivery of a composition to stimulate proliferation and/or cell cycle reentry of a postmitotic cell (e.g., postmitotic cardiomyocytes) the composition can be administered to a subject in need thereof by any mechanisms commonly known to those of skill in the art. Non-limiting examples include oral, systemic (e.g., transdermal, intranasal or by suppository), or parenteral (e.g., intramuscular, intravenous or subcutaneous) administration.

The present disclosure provides methods of stimulating proliferation and/or cell cycle reentry of a postmitotic cell in vivo, the method generally comprising, or alternatively consisting essentially of, or yet further consisting of administering to a subject in need thereof an amount effective to stimulate proliferation and/or cell cycle reentry, wherein said composition is capable of increasing expression of a cyclin-dependent kinase, a cyclin, and an aurora kinase, or equivalents thereof. In some embodiments, the methods generally involve contacting a postmitotic cell (e.g., a postmitotic cardiomyocyte) with a composition in an amount effective to stimulate proliferation and/or cell cycle reentry. The composition can comprise at least one proliferation and/or cell cycle reentry factor comprising, or alternatively consisting essentially or, or yet further consisting of, at least one polypeptide, at least one nucleic acid, at least one chemical, or a mixture thereof to increase expression of a cyclin-dependent kinase, a cyclin, and/or an aurora kinase, or equivalents thereof. The composition can comprises, or alternatively consists essentially or, or yet further consists of, at least one proliferation and/or cell cycle reentry factor comprising, at least one polypeptide, at least one nucleic acid, at least one chemical, or a mixture thereof to increase expression of at least one cyclin-dependent kinase and at least one cyclin, or equivalents thereof. In some embodiments the composition comprises, or alternatively consists essentially or, or yet further consists of, a CDK1, CCNB1 and an AURKB polypeptide. In some embodiments the composition comprises, or alternatively consists essentially or, or yet further consists of, a CDK1 and a CCNB1 polypeptide. In some embodiments the composition comprises, or alternatively consists essentially or, or yet further consists of, a CDK1, CCNB1, CDK4, and CCND1 polypeptide. In another embodiment, the composition comprises, or alternatively consists essentially or, or yet further consists of, a CDK1, CCNB1 and an AURKB nucleic acid. In another embodiment, the composition comprises, or alternatively consists essentially or, or yet further consists of, a CDK1 and CCNB1 nucleic acid. In another embodiment, the composition comprises, or alternatively consists essentially or, or yet further consists of, a CDK1, CCNB1, CDK4, and CCND1 nucleic acid. In other embodiments, the composition comprises, or alternatively consists essentially or, or yet further consists of, a chemical that increases expression of endogenous CDK1, CCNB1 and AURKB. In other embodiments, the composition comprises, or alternatively consists essentially or, or yet further consists of, a chemical that increases expression of endogenous CDK1 and CCNB1. In yet other embodiments, the composition comprises, or alternatively consists essentially or, or yet further consists of, a chemical that increases expression of endogenous CDK1, CCNB1, CDK4, and CCND1. In some embodiments, an aurora kinase is expressly excluded from the composition.

The composition can be a solid composition, a semi-solid composition, or a liquid composition. In some cases the composition is a controlled release composition, which may be a solid composition, a semi-solid composition, or a liquid composition. For example, the composition can be a sustained release matrix.

In some embodiments, the composition is administered to a subject in need thereof at or near a treatment site, for example, in or around the heart or brain. Administration of the composition can be achieved by various means, including via intravascular injection, intramyocardial delivery, and intracranial delivery. For example, intramyocardial delivery can be carried out using a catheter (e.g., via a transendocardial catheter system). Intramyocardial or intracranial delivery via a catheter can be global, focal or diffuse.

In some embodiments, the postmitotic cells which have been induced to proliferate or reenter the cell cycle are administered into a subject in need thereof in association with an implantable device. Suitable implantable devices contemplated by this invention include intravascular stents (e.g., self-expandable stents, balloon-expandable stents, and stent-grafts), scaffolds, grafts, and the like.

Factors to Stimulate Proliferation and/or Cell Cycle Reentry

As discussed, a postmitotic cell (e.g., a cardiomyocyte) may be modified to increase expression of a cell cycle regulating gene. The cell cycle regulating gene, for example, a cyclin-dependent kinase (CDK), cyclin, and/or aurora kinase can be encoded by a nucleic acid or can be a polypeptide. In some embodiments, the cell cycle regulating gene includes a cyclin-dependent kinase, a cyclin, an aurora kinase, or equivalents thereof. In other embodiments, the cell cycle regulating gene includes a cyclin-dependent kinase and a cyclin or an equivalent of each thereof. A postmitotic cell can be modified by introduction of a composition comprising proliferation and/or cell cycle reentry factors, such as at least one of a cyclin-dependent kinase, a cyclin, an aurora kinase, actin binding protein anillin (ANLN), a cell division cycle (CDC) protein, a cadherin, a COPS signalosome complex subunit, a cullin, a GTPase-activating protein, a protein regulator of cytokinesis and/or WNT1-inducible signaling pathway protein or equivalents thereof. A postmitotic cell can be modified by introduction of a composition comprising proliferation and/or cell cycle reentry factors such as: (1) cyclinB1 (CCNB1), aurora kinase B (AURKB) and cycle dependent kinase 1 (CDK1); (2) CCNB1 and CDK1; (3) cyclinD1 (CCND1), cycle dependent kinase 4 (CDK4); (4) CCNB1, CDK1, CCND1 and CDK4; (5) CCNB1, CCND1 and CDK4; or any combination thereof.

In some embodiments, the at least one nucleic acid is constitutively expressed.

Cyclin-Dependent Kinases

Cyclin-dependent kinases (CDKs) function in regulating progression through the cell cycle by complexing with their regulatory cyclins. For example, CDK1 binds cyclinB1 (CCNB1) and functions during M phase, while the CDK2/cyclinA complex ensures progression in S phase and S/G2 transition and CDK2/cyclinE promotes progression during G1/S phase. Gerard et al. (2012) *Frontiers in Physiol.* 3(413):1-18.

In some embodiments, the CDK is selected from the group consisting of CDK1, CDK2, CDK3, CDK4, and CDK6. In some embodiments, the CDK is CDK1. In other embodiments, the CDK is CDK4. In yet other embodiments, both CDK1 and CDK4 are used. In some embodiments, the CDK is constitutively expressed.

Amino acid sequences for CDKs (e.g., CDK1) and nucleotide sequences encoding CDK polypeptides, from a variety of species, are known in the art. See, e.g.: (1) GenBank Accession No. NP_001777.1 (*Homo sapiens* 297 amino acid cyclin-dependent kinase 1 isoform 1); (2) GenBank Accession No. AAH14563.1 (*Homo sapiens* 297 amino acid cell division cycle 2, G1 to S and G2 to M); (3) GenBank Accession No. NM_001786.4 (nucleotide sequence encoding the *Homo sapiens* cyclin-dependent kinase 1 (CDK1), transcript variant 1); (4) GenBank Accession No. NM_033379.4 (nucleotide sequence encoding the *Homo sapiens* cyclin-dependent kinase 1 (CDK1), transcript variant 1); (5) GenBank Accession No. NP_031685.2 (*Mus musculus* 297 cyclin-dependent kinase 1); (6) GenBank Accession No. NM_007659.3 (nucleotide sequence encoding the *Mus musculus* cyclin-dependent kinase 1).

In some embodiments, a suitable CDK1 nucleic acid comprises a nucleotide sequence having at least about 80%, at least about 85%, at least about 90%, at least about 95%, at least about 99%, or 100% nucleotide sequence identity of SEQ ID NO. 1 or SEQ ID NO. 7.

In some embodiments, a suitable CDK1 nucleic acid comprises a nucleotide sequence encoding a CDK1 polypeptide, where in some embodiments, a suitable CDK1 polypeptide comprises an amino acid sequence having at least about 80%, at least about 85%, at least about 90%, at least about 95%, at least about 99%, or 100% amino acid sequence identity of SEQ ID NO. 2 or SEQ ID NO. 8.

In some embodiments, a suitable CDK4 nucleic acid comprises a nucleotide sequence having at least about 80%, at least about 85%, at least about 90%, at least about 95%, at least about 99%, or 100% nucleotide sequence identity of SEQ ID NO. 13 or SEQ ID NO. 17.

In some embodiments, a suitable CDK4 nucleic acid comprises a nucleotide sequence encoding a CDK4 polypeptide, where in some embodiments, a suitable CDK4 polypeptide comprises an amino acid sequence having at least about 80%, at least about 85%, at least about 90%, at least about 95%, at least about 99%, or 100% amino acid sequence identity of SEQ ID NO. 14 or SEQ ID NO. 18.

Cyclins

A cyclin functions to control the progression of cells through the cell cycle by activating cyclin-dependent kinases (CDK). Galderisi et al. (2003) *Oncogene* 22(33): 5208-5219. Cyclin-CDK complexes activate other proteins through phosphorylation, which in turn are responsible for specific events in the cell cycle. Cyclins are well-characterized and divided into families. For example, the cyclinA family consists of two members, CCNA1 and CCNA2, while the cyclinB family consists of three members, CCNB1, CCNB2 and CCNB3. Different cyclins are active during different phases of the cell cycle. For example, cyclinA is active in the synthesis phase (S phase) during which DNA is replicated and occurs between G1 phase and G2 phase. On the other hand, CyclinD regulates transition from G1 to S phase. CyclinB regulates progression from G2 to M phase. In particular, CyclinB1 functions as a mitotic cyclin that binds to CDK1 and is necessary for the progression of cells in and out of M phase of the cell cycle.

In some embodiments, the cyclin is selected from the group consisting of cyclinA, cyclinB, cyclinD, and cyclinE. In some embodiments, the cyclinB is cyclinB1 (CCNB1). In other embodiments, the cyclinD is cyclinD1 (CCND1). In yet other embodiments, both CCNB1 and CCND1 are used.

Amino acid sequences for cyclin polypeptides (e.g., cyclinB1, CCNB1) and nucleotide sequences encoding cyclin polypeptides (e.g., cyclinB1, CCNB1), from a variety of species, are known in the art. See, e.g.: (1) GenBank Accession No. NP_114172 (*Homo sapiens* 433 amino acid Cyclin B1); (2) GenBank Accession No. AAH06510.1 (*Homo sapiens* 433 amino acid Cyclin B1); (3) GenBank Accession No. EAW51306.1 (*Homo sapiens* 433 amino acid Cyclin B1); (4) GenBank Accession No. NM_031966.3 (nucleotide sequence encoding the *Homo sapiens* Cyclin B1); (5) GenBank Accession No. NP 758505.2 (*Mus musculus* 430 amino acid cylcin B1); (6) GenBank Accession No. NM_172301.3 (nucleotide sequence encoding *Mus musculus* Cyclin B1).

In some embodiments, a suitable CCNB1 nucleic acid comprises a nucleotide sequence having at least about 80%, at least about 85%, at least about 90%, at least about 95%, at least about 99%, or 100% nucleotide sequence identity of SEQ ID NO. 3 or SEQ ID NO. 9.

In some embodiments, a suitable CCNB1 nucleic acid sequence comprises a nucleotide sequence encoding a CCNB1 polypeptide, where in some embodiments, a suitable CCNB1 polypeptide comprises an amino acid sequence encoding a polypeptide comprises a sequence having at least about 80%, at least about 85%, at least about 90%, at least about 95%, at least about 99%, or 100% amino acid sequence identity of SEQ ID NO. 4 or SEQ ID NO. 10.

In some embodiments, a suitable CCND1 nucleic acid comprises a nucleotide sequence having at least about 80%, at least about 85%, at least about 90%, at least about 95%, at least about 99%, or 100% nucleotide sequence identity of SEQ ID NO. 15 or SEQ ID NO. 19.

In some embodiments, a suitable CCNB1 nucleic acid sequence comprises a nucleotide sequence encoding a CCNB1 polypeptide. In some embodiments, a suitable CCNB1 polypeptide comprises an amino acid sequence encoding a polypeptide comprises a sequence having at least about 80%, at least about 85%, at least about 90%, at least about 95%, at least about 99%, or 100% amino acid sequence identity of SEQ ID NO. 16 or SEQ ID NO. 20.

Aurora Kinases

Aurora kinases are serine/threonine kinases that are crucial for cell cycle control. Fu et al. (2007) *Mol Cancer Res* 5(1):1-10. These kinases function to control chromatid segregation during cell division. To date, three mammalian aurora kinases have been identified—aurora kinase A (AURKA), aurora kinase B (AURKB) and aurora kinase C (AURKC). In particular, AURKB specifically functions, in part, in the attachment of mitotic spindles to the centromere.

Amino acid sequences for aurora kinase polypeptides (e.g., AURKB) and nucleotide sequences encoding aurora kinase polypeptides (e.g., AURKB), from a variety of species, are known in the art. See, e.g.: (1) GenBank Accession No. NP 004208.2 (*Homo sapiens* 344 amino acid aurora kinase B isoform 1); (2) GenBank Accession No. NP_001243763.1 (*Homo sapiens* 303 amino acid aurora kinase B isoform 2); (3) GenBank Accession No. NP_001271455.1 (*Homo sapiens* 345 amino acid aurora kinase B isoform 3); (4) GenBank Accession No. AAH00442.3 (*Homo sapiens* 344 amino acid aurora kinase B); (5) GenBank Accession No. NM_004217.3 (nucleotide sequence encoding the *Homo sapiens* AURKB, transcript variant 1); (6) GenBank Accession No. NM_001256834.1 (nucleotide sequence encoding the *Homo sapiens* AURKB, transcript variant 2); (7) GenBank Accession No. NM_001284526.1 (nucleotide sequence encoding the *Homo sapiens* AURKB, transcript variant 3); (8) GenBank Accession No. NP_035626.1 (*Mus musculus* 345 amino acid aurora kinase B); (9) GenBank Accession No. AAH03261.1 (*Mus musculus* 345 amino acid aurora kinase B); (10) GenBank Accession No. NM_011496.1 (nucleotide sequence encoding the *Mus musculus* aurora kinase B).

In some embodiments, a suitable AURKB nucleic acid comprises a nucleotide sequence having at least about 80%, at least about 85%, at least about 90%, at least about 95%, at least about 99%, or 100% nucleotide sequence identity of SEQ ID NO. 5 or SEQ ID NO. 11.

In some embodiments, a suitable AURKB nucleic acid sequence comprises a nucleotide sequence encoding an AURKB polypeptide, where in some embodiments, a suitable AURKB polypeptide comprises an amino acid sequence having at least about 80%, at least about 85%, at least about 90%, at least about 95%, at least about 99%, or 100% amino acid sequence identity of SEQ ID NO. 6 or SEQ ID NO. 12.

It has further been discovered that introduction of nucleic acid sequences encoding CDK1, CCNB1, CDK4 and CCND1 is sufficient to induce postmitotic cell (e.g., cardiomyocyte and neuron) proliferation and/or cell cycle reentry. In some embodiments, the CDK is CDK1 and the cyclin is CCNB1.

It has been discovered that introduction of nucleic acid sequences encoding CDK1, CCNB1 and AURKB is sufficient to induce cardiac cell (e.g., postmitotic cardiomyocytes) proliferation and/or cell cycle reentry.

Numerous markers and methods can be used to identify postmitotic cells that have been induced to proliferate and/or reenter the cell cycle. For example, proliferating cells can be identified by immunocytochemistry analysis for cells expressing both a proliferation marker (e.g., Ki67, PHH3, EdU) and a cell specific marker. Cells with no or low proliferative capacity can be identified as having low or no expression of proliferation markers. Low expression can be less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, or no expression as compared to a proliferating control sample (e.g., a stem or progenitor cell). Non-limiting examples of cardiac markers include cardiac troponin T (cTnT), myosin heavy chain (MYH), alpha actinin and/or connexin 43. Non-limiting examples of neural marker include nestin, neuronal nuclei (NeuN), microtubule-associate protein 2 (MAP2), beta III tubulin, neuron specific enolase (NSE), oligodendrocyte lineage (Olig1/2), and glial fibrillary acidic protein (GFAP). Non-limiting examples of pancreatic markers include Pax4, Nkx2.2, Ngn3, insulin, glucagon, and somatostatin.

The expression of various cell markers may be detected by conventional biochemical or immunochemical methods (e.g., enzyme-linked immunosorbent assay, immunohistochemical assay, and the like). Alternatively, expression of a nucleic acid encoding a cell specific marker can be assessed. Expression of cell-specific marker-encoding nucleic acids in a cell can be confirmed by reverse transcriptase polymerase chain reaction (RT-PCR) or hybridization analysis, molecular biological methods which have been commonly used in the past for amplifying, detecting and analyzing mRNA coding for any marker proteins. Nucleic acid sequences coding for markers specific to cardiomyocytes, neural cells, pancreatic cells, hair cells, and skeletal muscle cells are known and are available through public databases such as GenBank. Thus, marker-specific sequences needed for use as primers or probes are easily determined.

Genetic Modification

In some embodiments postmitotic cells (e.g., postmitotic cardiomyocytes) are induced to proliferate and/or reenter the cell cycle by administering to the postmitotic cells a composition that genetically modifies the postmitotic cells. The composition may comprise at least one nucleic acid comprising nucleotide sequences encoding a cell cycle regulating polypeptide, for example, a cyclin-dependent kinase, a cyclin, and an aurora kinase polypeptide (referred to generically as "at least one nucleic acid"). In some embodiments, an aurora kinase is expressly excluded from the composition and/or methods of inducing proliferation and/or cell cycle reentry of the postmitotic cell.

The at least one nucleic acid comprising nucleotide sequences encoding the proliferation and/or cell cycle reentry factors can be a recombinant expression vector, where suitable vectors include, e.g., recombinant retroviruses, lentiviruses, and adenoviruses, adeno-associated viruses (AAV), retroviral expression vectors, lentiviral expression vectors, nucleic acid expression vectors, and plasmid expression vectors. In some cases, the at least one nucleic acid is integrated into the genome of a postmitotic cell (e.g., postmitotic cardiomyocyte) and its progeny. In other cases, the at least one nucleic acid persists in an episomal state in the postmitotic cell and its progeny. In some cases, an endogenous, natural version of at least one proliferation and/or cell cycle reentry factor may already exist in the postmitotic cell but an additional exogenous factor (e.g., at least one nucleic acid) is added to the postmitotic cell to induce proliferation and/or cell cycle reentry of the postmitotic cell. In other cases, the at least one nucleic acid encodes at least one proliferation and/or cell cycle reentry factor polypeptide having an amino acid sequence that differs by one or more amino acids from a polypeptide encoded by an endogenous proliferation and/or cell cycle reentry factor encoding nucleic acid within the postmitotic cell.

In some embodiments, a postmitotic cell (e.g., postmitotic cardiomyocyte) is genetically modified with separate expression constructs, each expression construct comprising a nucleic sequence encoding one proliferation and/or cell cycle reentry factor. In some embodiments, a postmitotic cell (e.g., postmitotic cardiomyocyte) is genetically modified with multiple expression constructs, each expression construct comprising a nucleic sequence encoding one proliferation and/or cell cycle reentry factor. In some embodiments, a postmitotic cell (e.g., postmitotic cardiomyocyte) is genetically modified with three separate expression constructs, each expression construct comprising a nucleic sequence encoding one proliferation and/or cell cycle reentry factor. In some embodiments, a postmitotic cell (e.g., postmitotic cardiomyocyte) is genetically modified with two separate expression constructs, each expression construct comprising a nucleic sequence encoding at least one proliferation and/or cell cycle reentry factor. In some embodiments, a postmitotic cell (e.g., postmitotic cardiomyocyte) is genetically modified with one expression construct, the expression construct comprising a nucleic sequence encoding at least one proliferation and/or cell cycle reentry factor. In some embodiments, a postmitotic cell (e.g., postmitotic cardiomyocyte) is genetically modified with one expression construct, the expression construct comprising nucleotide sequences encoding sequences of several cell cycle regulating factors. In some embodiments, a postmitotic cell (e.g., postmitotic cardiomyocyte) is genetically modified with one expression construct, the expression construct comprising nucleotide sequences encoding sequences of all of CDK1 and CCNB1, and optionally including CDK4 and/or CCND1. In some embodiments, sequence encoding CDK1 and CCNB1, and optionally including CDK4 and/or CCND1, are in one expression vector, two expression vectors (e.g., CDK1 is expressed from a separate vector as CCNB1), or four expression vectors (e.g., CDK1, CCNB1, CDK4 and CCND1 are all expressed from separate vectors).

In some embodiments, a postmitotic cell (e.g., postmitotic cardiomyocyte) is genetically modified with one expression construct, the expression construct comprising nucleotide sequences encoding sequences of all three of CDK1, CCNB1 and AURKB. In some embodiments, sequence encoding CDK1, CCNB1 and AURKB are in one expression vector, two expression vectors (e.g., CDK1 is expressed from a separate vector as CCNB1 and AURKB), or three expression vectors (e.g., CDK1, CCNB1 and AURKB are all expressed from separate vectors).

In some embodiments, one or more exogenous nucleic acids comprising nucleotide sequences encoding proliferation and/or cell cycle reentry factor polypeptides is introduced into a single postmitotic cell (e.g., postmitotic cardiomyocyte). In other embodiments, one or more exogenous nucleic acids comprising nucleotide sequences encoding proliferation and/or cell cycle reentry factor polypeptides is introduced into a population of postmitotic cells (e.g., a population of postmitotic cardiomyocytes) in vitro. In some embodiments, one or more exogenous nucleic acids comprising nucleotide sequences encoding proliferation and/or cell cycle reentry factor polypeptides is introduced into a postmitotic cell (e.g., a single postmitotic cardiomyocyte or a population of postmitotic cardiomyocytes) in vivo.

Where a population of cardiac cells is genetically modified (in vitro or in vivo) with one or more exogenous nucleic acids comprising nucleotide sequences encoding proliferation and/or cell cycle reentry factor polypeptides, the one or more exogenous nucleic acids can be introduced into greater than 0.1% of the total population of postmitotic cells, e.g., 0.2%, 0.3%, 0.4%, 0.5%, 0.6%, 0.7%, 0.8%, 0.9%, 1% or other percent of cells greater than 0.1%.

In other embodiments, where a population of postmitotic cells is genetically modified (in vitro or in vivo) with one or more exogenous nucleic acids comprising nucleotide sequences encoding proliferation and/or cell cycle reentry factor polypeptides, the one or more exogenous nucleic acids can be introduced into greater than 1% of the total population of cardiac cells, e.g., 2%, 3%, 5%, 10%, 12%, 15%, 20%, or other percent of cells greater than 1%.

In other embodiments, where a population of postmitotic cells is genetically modified (in vitro or in vivo) with one or more exogenous nucleic acids comprising nucleotide sequences encoding proliferation and/or cell cycle reentry factor polypeptides, the one or more exogenous nucleic acids can be introduced into greater than 20% of the total population of postmitotic cells, e.g., 25%, 30%, 35%, 40%, 45%, 50%, 55%, 60%, 65%, 70%, 75%, 80%, 85%, 90%, 95% or other percent of cells greater than 20%.

In some embodiments, the one or more nucleic acids comprising nucleotide sequences encoding proliferation and/or cell cycle reentry factor polypeptides is in an expression construct that provides for production of the one or more proliferation and/or cell cycle reentry factor polypeptides in the genetically modified postmitotic cells. In some embodiments, the expression construct is a viral construct, e.g., a recombinant adeno-associated virus construct (e.g., U.S. Pat. No. 7,078,387), a recombinant adenoviral construct, a recombinant lentiviral construct, etc.

Suitable expression vectors include, but are not limited to, viral vectors (e.g. viral vectors based on vaccinia virus; poliovirus; adenovirus (e.g., Li et al. (1994) *Invest Opthalmol Vis Sci* 35:2543-2549; Borras et al. (1999) *Gene Ther* 6:515-524; Li and Davidson, (1995) *Proc. Natl. Acad. Sci.* 92:7700-7704; Sakamoto et al. (1999) *Hum Gene Ther* 5:1088-1097; WO 94/12649; WO 93/03769; WO 93/19191; WO 94/28938; WO 95/11984 and WO 95/00655); adeno-associated virus (e.g., Ali et al. (1998) *Hum Gene Ther* 9(1):81-86, 1998, Flannery et al. (1997) *Proc. Natl. Acad. Sci.* 94:6916-6921; Bennett et al. (1997) *Invest Opthalmol Vis Sci* 38:2857-2863; Jomary et al. (1997) *Gene Ther* 4:683-690; Rolling et al. (1999), *Hum Gene Ther* 10:641-648; Ali et al. (1996) *Hum Mol Genet.* 5:591-594; WO 93/09239, Samulski et al. (1989) *J. Vir.* 63:3822-3828; Mendelson et al. (1988) *Virol.* 166:154-165; and Flotte et al. (1993) *Proc. Natl. Acad. Sci.* 90:10613-10617; SV40; herpes simplex virus; human immunodeficiency virus (e.g., Miyoshi et al. (1997) *Proc. Natl. Acad. Sci.* 94:10319-10323; Takahashi et al. (1999) *J Virol* 73:7812-7816); a retroviral vector (e.g., Murine-Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

Numerous suitable expression vectors are known to those of skill in the art, and many are commercially available. The following vectors are provided by way of example; for eukaryotic cells: pXT1, pSG5 (Stratagene), pSVK3, pBPV, pMSG, pSVLSV40 (Pharmacia), and pAd (Life Technologies). However, any other vector may be used so long as it is compatible with the cells of the present disclosure.

Depending on the host/vector system utilized, any of a number of suitable transcription and translation control elements, including constitutive and inducible promoters, transcription enhancer elements, transcription terminators, etc. may be used in the expression vector (e.g., Bitter et al. (1987) *Methods in Enzymology,* 153:516-544).

In some embodiments, a proliferation and/or cell cycle reentry factor encoding nucleotide sequence (e.g., a CCNB1-encoding nucleotide sequence, an AURKB-encoding nucleotide sequence, a CDK1-encoding nucleotide sequence, a CCND1-encoding nucleotide sequence, or a CDK4-encoding nucleotide sequence) is operably linked to a control element, e.g., a transcriptional control element, such as a promoter. The transcriptional control element is functional in a eukaryotic cell, for example, a mammalian cardiac cell. Suitable transcriptional control elements include promoters and enhancers. In some embodiments, the promoter is constitutively active. In other embodiments, the promoter is inducible.

Non-limiting examples of suitable eukaryotic promoters (promoters functional in a eukaryotic cell) include CMV, CMV immediate early, HSV thymidine kinase, early and late SV40, long terminal repeats (LTRs) from retrovirus, and mouse metallothionein-I. In some embodiments, promoters that are capable of conferring cardiac specific expression will be used. Non-limiting examples of suitable cardiac specific promoters include desmin (Des), alpha-myosin heavy chain (α-MHC), myosin light chain 2 (MLC-2), cardiac troponin T (cTnT) and cardiac troponin C (cTnC). Non-limiting examples of suitable neuron specific promoters include synapsin I (SYN), calcium/calmodulin-dependent protein kinase II, tubulin alpha I, neuron-specific enolase and platelet-derived growth factor beta chain promoters and hybrid promoters by fusing cytomegalovirus enhancer (E) to those neuron-specific promoters.

In some embodiments, a proliferation and/or cell cycle reentry factor encoding nucleotide sequence is operably linked to a cell type-specific transcriptional regulator element (TRE), where TREs include promoters and enhancers. Suitable TREs include, but are not limited to, TREs derived from the following genes: myosin light chain-2, α-myosin heavy chain, AE3, cardiac troponin C, and cardiac actin. Franz et al. (1997) *Cardiovasc. Res.* 35:560-566; Robbins et al. (1995) *Ann. N.Y. Acad. Sci.* 752:492-505; Linn et al. (1995) *Circ. Res.* 76:584-591; Parmacek et al. (1994) *Mol. Cell. Biol.* 14:1870-1885; Hunter et al. (1993) *Hypertension* 22:608-617; and Sartorelli et al. (1992) *Proc. Natl. Acad. Sci. USA* 89:4047-4051.

Selection of the appropriate vector and promoter is well within the level of ordinary skill in the art. The expression vector may also contain a ribosome binding site for translation initiation and a transcription terminator. The expression vector may also include appropriate sequences for amplifying expression.

Examples of suitable mammalian expression vectors (expression vectors suitable for use in mammalian postmitotic cells) include, but are not limited to: recombinant viruses, nucleic acid vectors, such as plasmids, bacterial artificial chromosomes, yeast artificial chromosomes, human artificial chromosomes, cDNA, cRNA, and polymerase chain reaction (PCR) product expression cassettes. Examples of suitable promoters for driving expression of proliferation and/or cell cycle reentry factor polypeptide-encoding nucleotide sequences include, but are not limited to, retroviral long terminal repeat (LTR) elements; constitutive promoters such as CMV, HSV1-TK, SV40, EF-1α, β-actin, phosphoglycerol kinase (PGK); inducible promoters, such as those containing Tet-operator elements; cardiac specific promoters, such as desmin (Des), alpha-myosin heavy chain (α-MHC), myosin light chain 2 (MLC-2), cardiac troponin T (cTnT) and cardiac troponin C (cTnC); neural specific promoters, such as nestin, neuronal nuclei (NeuN), microtubule-associate protein 2 (MAP2), beta III tubulin, neuron specific enolase (NSE), oligodendrocyte lineage (Olig1/2), and glial fibrillary acidic protein (GFAP); and pancreatic specific promoters, such as Pax4, Nkx2.2, Ngn3, insulin, glucagon, and somatostatin.

In some cases, the mammalian expression vector(s) encodes, in addition to exogenous proliferation and/or cell cycle reentry factor polypeptides, a marker gene that facilitates identification or selection of cells that have been transfected, transduced or infected. Examples of marker genes include, but are not limited to, genes encoding fluorescent proteins, e.g., enhanced green fluorescent protein, Ds-Red (DsRed: *Discosoma* sp. red fluorescent protein (RFP); Bevis et al. (2002) *Nat. Biotechnol.* 20(11):83-87), yellow fluorescent protein, mCherry, and cyanofluorescent protein; and genes encoding proteins conferring resistance to a selection agent, e.g., a neomycin resistance gene, a puromycin resistance gene, a blasticidin resistance gene, and the like.

In one embodiment, the expression vector further comprises, or alternatively consists essentially of, or yet further consists of a suicide gene. Expression of the suicide gene may be regulated by the same or different promoter as that which expresses the at least one proliferation and/or cell cycle reentry factor polypeptide-encoding nucleotide. A suicide gene is one that allows for the negative selection of the cells. In the methods described herein, a suicide gene is used as a safety system, allowing the cells expressing the gene to be killed by introduction of a selective agent. This is desirable in case the recombinant gene causes a mutation leading to uncontrolled cell growth. A number of suicide gene systems have been identified, including the herpes simplex virus thymidine kinase (tk or TK) gene, the cytosine deaminase gene, the varicella-zoster virus thymidine kinase gene, the nitroreductase gene, the *Escherichia coli* gpt gene, and the *E. coli* Deo gene (also see, for example, Yazawa K, Fisher W E, Brunicardi F C: Current progress in suicide gene therapy for cancer. *World J. Surg.* (2002) 26(7):783-9). In one embodiment, the suicide gene is the thymidine kinase (TK) gene. In one aspect, the TK gene is a wild-type TK gene. In other aspects, the TK gene is a mutated form of the gene, e.g., sr23tk. Cells expressing the TK protein can be killed using ganciclovir. In another embodiment, the nucleic acid encoding the tetracycline activator protein and the suicide gene are regulated by one promoter.

Examples of suitable viral vectors include, but are not limited, viral vectors based on retroviruses (including lentiviruses); adenoviruses; adeno-associated viruses, and episomal vectors. An example of a suitable retrovirus-based vector is a vector based on murine moloney leukemia virus (MMLV); however, other recombinant retroviruses may also be used, e.g., Avian Leukosis Virus, Bovine Leukemia Virus, Murine Leukemia Virus (MLV), Mink-Cell focus-Inducing Virus, Murine Sarcoma Virus, Reticuloendotheliosis virus, Gibbon Abe Leukemia Virus, Mason Pfizer Monkey Virus, or Rous Sarcoma Virus (e.g., U.S. Pat. No. 6,333,195).

In other cases, the retrovirus-based vector is a lentivirus-based vector, (e.g., Human Immunodeficiency Virus-1 (HIV-1), Simian Immunodeficiency Virus (SIV) or Feline Immunodeficiency Virus (FIV)). Johnston et al. (1999), *Journal of Virology,* 73(6):4991-5000 (FIV); Negre D et al. (2002) *Current Topics in Microbiology and Immunology,* 261:53-74 (SIV); Naldini et al. (1996) *Science,* 272:263-267 (HIV).

The recombinant retrovirus may comprise a viral polypeptide (e.g., retroviral env) to aid entry into the target cell. Such viral polypeptides are well-established in the art, for example, U.S. Pat. No. 5,449,614. The viral polypeptide may be an amphotropic viral polypeptide, for example, amphotropic env, which aids entry into cells derived from multiple species, including cells outside of the original host species. The viral polypeptide may be a xenotropic viral polypeptide that aids entry into cells outside of the original host species. In some embodiments, the viral polypeptide is an ecotropic viral polypeptide, for example, ecotropic env, which aids entry into cells of the original host species.

Examples of viral polypeptides capable of aiding entry of retroviruses into cells include but are not limited to: MMLV amphotropic env, MMLV ecotropic env, MMLV xenotropic env, vesicular stomatitis virus-g protein (VSV-g), HIV-1 env, Gibbon Ape Leukemia Virus (GALV) env, RD114, FeLV-C, FeLV-B, MLV 10A1 env gene, and variants thereof, including chimeras. Yee et al. (1994) *Methods Cell Biol., Pt A:*99-112 (VSV-G); U.S. Pat. No. 5,449,614. In some cases, the viral polypeptide is genetically modified to promote expression or enhanced binding to a receptor.

In general, a recombinant virus is produced by introducing a viral DNA or RNA construct into a producer cell. In some cases, the producer cell does not express exogenous genes. In other cases, the producer cell is a "packaging cell" comprising one or more exogenous genes, e.g., genes encoding one or more gag, pol, or env polypeptides and/or one or more retroviral gag, pol, or env polypeptides. The retroviral packaging cell may comprise a gene encoding a viral polypeptide, e.g., VSV-g that aids entry into target cells. In some cases, the packaging cell comprises genes encoding one or more lentiviral proteins, e.g., gag, pol, env, vpr, vpu, vpx, vif, tat, rev, or nef. In some cases, the packaging cell comprises genes encoding adenovirus proteins such as E1A or E1B or other adenoviral proteins. For example, proteins supplied by packaging cells may be retrovirus-derived proteins such as gag, pol, and env; lentivirus-derived proteins such as gag, pol, env, vpr, vpu, vpx, vif, tat, rev, and nef; and adenovirus-derived proteins such as E1A and E1B. In many examples, the packaging cells supply proteins derived from a virus that differs from the virus from which the viral vector derives.

Packaging cell lines include but are not limited to any easily-transfectable cell line. Packaging cell lines can be based on 293T cells, NIH3T3, COS or HeLa cell lines. Packaging cells are often used to package virus vector plasmids deficient in at least one gene encoding a protein required for virus packaging. Any cells that can supply a protein or polypeptide lacking from the proteins encoded by such virus vector plasmid may be used as packaging cells. Examples of packaging cell lines include but are not limited to: Platinum-E (Plat-E), Platinum-A (Plat-A), BOSC 23 (ATCC CRL 11554) and Bing (ATCC CRL 11270). Morita et al. (2000) *Gene Therapy* 7(12):1063-1066; Onishi et al. (1996) *Experimental Hematology,* 24:324-329; U.S. Pat. No. 6,995,009. Commercial packaging lines are also useful, e.g., Ampho-Pak 293 cell line, Eco-Pak 2-293 cell line, RetroPack PT67 cell line, and Retro-X Universal Packaging System (all available from Clontech).

The retroviral construct may be derived from a range of retroviruses, e.g., MMLV, HIV-1, SIV, FIV, or other retrovirus described herein. The retroviral construct may encode all viral polypeptides necessary for more than one cycle of replication of a specific virus. In some cases, the efficiency of viral entry is improved by the addition of other factors or other viral polypeptides. In other cases, the viral polypeptides encoded by the retroviral construct do not support more than one cycle of replication, e.g., U.S. Pat. No. 6,872,528. In such circumstances, the addition of other factors or other viral polypeptides can help facilitate viral entry. In an exemplary embodiment, the recombinant retrovirus is HIV-1 virus comprising a VSV-g polypeptide but not comprising a HIV-1 env polypeptide.

The retroviral construct may comprise: a promoter, a multi-cloning site, and/or a resistance gene. Examples of promoters include but are not limited to CMV, SV40, EF1$\alpha$, $\beta$-actin; retroviral LTR promoters, and inducible promoters. The retroviral construct may also comprise a packaging signal (e.g., a packaging signal derived from the MFG vector; a psi packaging signal). Examples of some retroviral constructs known in the art include but are not limited to: pMX, pBabeX or derivatives thereof. Onishi et al. (1996) *Experimental Hematology,* 24:324-329. In some cases, the retroviral construct is a self-inactivating lentiviral vector (SIN) vector. Miyoshi et al. (1998) *J. Virol.* 72(10):8150-8157. In some cases, the retroviral construct is LL-CG, LS-CG, CL-CG, CS-CG, CLG or MFG. Miyoshi et al. (1998) *J Virol.* 72(10):8150-8157; Onishi et al. (1996) *Experimental Hematology,* 24:324-329; Riviere et al. (1995) *Proc. Natl. Acad. Sci.,* 92:6733-6737. Virus vector plasmids (or constructs), include: pMXs, pMxs-IB, pMXs-puro, pMXs-neo (pMXs-IB is a vector carrying the blasticidin-resistant gene instead of the puromycin-resistant gene of pMXs-puro) Kimatura et al. (2003) *Experimental Hematology* 31: 1007-1014; MFG Riviere et al. (1995) *Proc. Natl. Acad. Sci.,* 92:6733-6737; pBabePuro; Morgenstern et al. (1990) *Nucleic Acids Research* 18:3587-3596; LL-CG, CL-CG, CS-CG, CLG Miyoshi et al. (1998) *J Vir.* 72:8150-8157 and the like as the retrovirus system, and pAdexl Kanegae et al. (1995) *Nucleic Acids Research* 23:3816-3821 and the like as the adenovirus system. In exemplary embodiments, the retroviral construct comprises blasticidin (e.g., pMXs-IB), puromycin (e.g., pMXs-puro, pBabePuro); or neomycin (e.g., pMXs-neo). Morgenstern et al. (1990) *Nucleic Acids Research* 18:3587-3596.

Methods of producing recombinant viruses from packaging cells and their uses are well established; see, e.g., U.S. Pat. Nos. 5,834,256; 6,910,434; 5,591,624; 5,817,491; 7,070,994; and 6,995,009. Many methods begin with the introduction of a viral construct into a packaging cell line. The viral construct may be introduced into a host fibroblast by any method known in the art, including but not limited to: a calcium phosphate method, a lipofection method (e.g., Felgner et al. (1987) *Proc. Natl. Acad. Sci.* 84:7413-7417), an electroporation method, microinjection, Fugene transfection, nucleofection and the like, and any method described herein.

One or more nucleic acids encoding proliferation and/or cell cycle reentry factors can be introduced into a postmitotic cell using a variety of well-known techniques, such as non-viral based transfection of the cell. In an exemplary aspect a construct is incorporated into a vector and introduced into a cardiac cell. Introduction into the cardiac cell may be performed by any non-viral based transfection method known in the art, such as, but not limited to, electroporation, calcium phosphate mediated transfer, nucleofection, sonoporation, heat shock, magnetofection, liposome mediated transfer, microinjection, microprojectile mediated transfer (nanoparticles), cationic polymer mediated transfer (DEAE-dextran, polyethylenimine, polyethylene glycol (PEG) and the like, or cell fusion. Other methods of transfection include transfection reagents such as Lipofectamine™ Dojindo Hilymax™, Fugene™, jetPEI™, Effectene™, and DreamFect™.

In some embodiments, the at least one nucleic acid is a synthetic messenger RNA (mRNA). Synthetic mRNAs provide the genetic information for making proteins of interest and can be chemically modified to avoid triggering an immune response. Zangi et al. (2013) *Nature Biotech* 31:898-907. Since mRNAs do not integrate into the host cell genome, the synthetic RNA acts for a period of time and then disappears as the cell divides. In some embodiments the synthetic mRNAs are modified, for example, with pseudouridine and/or 5-methyl-cytidine, to reduce innate antiviral response to single-stranded RNA. In some embodiments, the synthetic RNAs encode CCNB1, CCND1, CDK1, CDK4, AURKB or combinations and/or equivalents of each thereof.

In some embodiments, a suitable synthetic RNA encoding CDK1 comprises a nucleotide sequence having at least about 80%, at least about 85%, at least about 90%, at least about 95%, at least about 99%, or 100% nucleotide sequence identity of SEQ ID NO. 1 or SEQ ID NO. 7. In some embodiments, a suitable synthetic RNA encoding CCNB1 comprises a nucleotide sequence having at least about 80%, at least about 85%, at least about 90%, at least about 95%, at least about 99%, or 100% nucleotide sequence identity of SEQ ID NO. 3 or SEQ ID NO. 9. In some embodiments, a suitable synthetic RNA encoding AURKB comprises a nucleotide sequence having at least about 80%, at least about 85%, at least about 90%, at least about 95%, at least about 99%, or 100% nucleotide sequence identity of SEQ ID NO. 5 or SEQ ID NO. 11. In some embodiments, a suitable synthetic RNA encoding CDK4 comprises a nucleotide sequence having at least about 80%, at least about 85%, at least about 90%, at least about 95%, at least about 99%, or 100% nucleotide sequence identity of SEQ ID NO. 13 or SEQ ID NO. 17. In some embodiments, a suitable synthetic RNA encoding CCND1 comprises a nucleotide sequence having at least about 80%, at least about 85%, at least about 90%, at least about 95%, at least about 99%, or 100% nucleotide sequence identity of SEQ ID NO. 15 or SEQ ID NO. 19.

Protein Modification

In another aspect polypeptides can be introduced into postmitotic cells using any method known in the art. Protein delivery (i.e., protein transduction) is the process by which a peptide or protein motif crosses the cell plasma membrane. Methods to introduce peptides into cells include, for example, transfection, micro-injection, electroporation, nanoparticle, virus-like particles (VLP). In some embodiments, the proteins are CCNB1, CCND1, CDK1, CDK4, AURKB or combinations and/or equivalents of each thereof.

Chemical Modification

In another aspect, the disclosure provides a method of inducing proliferation and/or cell cycle reentry of a postmitotic cells, the method comprising administering to the cell a composition comprising at least one chemical in an amount effective to stimulate proliferation and/or cell cycle reentry wherein said chemical composition is capable of increasing expression of a cyclin-dependent kinase, a cyclin, and an aurora kinase, or equivalents thereof. In other embodiments, the method comprises, or alternatively consists essentially of, or yet further consists of, contacting the cell a with an effective amount of at least one chemical that increases expression of at least one cyclin-dependent kinase, at least one a cyclin, or equivalents thereof. In some embodiments, the chemical increases expression of CCNB1, CCND1, CDK1, CDK4, combinations and/or equivalents of each thereof.

Any compound now known or later discovered which is capable of increasing expression of a cyclin-dependent kinase, a cyclin, or an aurora kinase (e.g., CDK1, CDK4, CCNB1, CCND1, or AURKB) or equivalents of each thereof is within the purview of this disclosure. Compounds should be understood to also encompass all pharmaceutically acceptable derivatives that can be used in association with one or more pharmaceutically acceptable excipients, diluents or carriers.

In other aspects, the disclosure provides a method of inducing proliferation and/or cell cycle reentry of a postmitotic cell, the method comprising, or alternatively consisting essentially of, or yet further consisting of, contacting the cell with an effective amount of a chemical composition to stimulate proliferation and/or cell cycle reentry wherein said chemical composition is capable of inhibiting expression of negative regulators of cellular proliferation and/or cell cycle reentry. For example, a Weel inhibitor can be used to induce expression of CDK1. In some embodiments, activation of CDK1 with small molecule MK1775 (a Weel inhibitor) can replace CDK1 and/or CCNB from the cocktail.

Additional Agents and Cell Cycle Regulating Factors

A postmitotic cell (e.g., a postmitotic cardiomyocyte) can be modified (genetically or non-genetically) as described above, and can also be contacted with one or more additional agents and/or factors which can be added to the composition, e.g., the one or more additional agents and/or factors can be included as additives to the culture media or to the composition.

In some embodiments, other cell cycle regulating genes can be included in the composition including, for example, actin binding protein anillin (ANLN), cell division cycle-5 (CDC5), cadherin-6 (CDH6), cyclin dependent-kinase 2 (CDK2), cyclin dependent-kinase 3 (CDK3), centromere protein A (CENPA), COPS signalosome subunit 5 (COPS5), cullin 3 (CUL3), GTPase-activating protein (CYK4), protein regulator of cytokinesis 1 (PRC1) and/or WNT1-inducible signaling pathway protein 1 (WISP1).

In some embodiments, use of a compound that releases cell cycle blocks in postmitotic cells, for example a p38 inhibitor, a p21 inhibitor, a p57 inhibitor, or a pharmaceutically acceptable derivative thereof can be used to facilitate an increase in proliferation and/or cell cycle reentry. In some embodiments, a small molecule inhibitor can be used. In other embodiments, an siRNA can be used to decrease expression. Both small molecule inhibitors and siRNAs for p38, p21, p57 and the like are commercially available.

In some embodiments, a first composition of one or more proliferation and/or cell cycle reentry factors is added to a postmitotic cell for a period of time followed by a second composition of one or more proliferation and/or cell cycle reentry factors. For example, a combination of CDK4 and CCND1 can act to enhance the number of cells in G1 and S, referred to herein as a "G1 cocktail." Other combinations of factors, for example, CDK1 and CCNB can act as a "G2 cocktail" and enhance the number of cells in G2, but not G1 or S. Combinations of CDK1, CCNB1, CDK4 and CCND1 can induce a balanced distribution of G1/G2 cells. In some embodiments, a G1 cocktail is added for a period of time, followed by a G2 cocktail. The G2 cocktail can be added to the G1 cocktail or can replace the G2 cocktail. In some embodiments, after the G2 cocktail has been added to the postmitotic cells for a period of time, the G1 cocktail can be added to the cells. The G1 cocktail can be added in addition to the G2 cocktail, or the G1 cocktail can replace the G2 cocktail. In one preferred embodiment, a G1 cocktail of CDK4 and CCND1 modified mRNAs can be added to a population of postmitotic cells for a period of time, the G1 cocktail can then be removed, and a G2 cocktail of CDK1 and CCNB1 modified mRNAs can be added to the population of postmitotic cells for a period of time. The G1 and G2 cocktails can be alternated in a similar pattern to induce proliferation of the postmitotic cells. It is contemplated that alternating exposure of the postmitotic cells to the G1 and G2 cocktails can help to more efficiently drive the cells through the cell cycle.

III. Compositions

The present disclosure also provides an isolated, proliferative postmitotic cell modified to overexpress proliferation and/or cell cycle reentry factors (e.g., CDK1, CCNB1, and AURKB or equivalents thereof).

In one aspect the disclosure also provides a composition comprising, or alternatively consisting essentially or, or yet further consisting of, an isolated, proliferative postmitotic cell modified to overexpress proliferation and/or cell cycle reentry factors (e.g., CDK1, CCNB1, CDK4, CCND1, and/or AURKB or combinations and/or equivalents of each thereof).

In some aspects are provided, isolated, proliferative postmitotic cell modified to overexpress at least one CDK and at least one cyclin, or an equivalent of each thereof. In other aspects are provided isolated, proliferative postmitotic cell modified to overexpress CDK1 and CCNB1, or an equivalent of each thereof. In some embodiments, the cells are further modified to overexpress CDK4, CCND1, or both.

In another aspect provided is a substantially homogenous population proliferative postmitotic cells. In some embodiments, a composition comprises a population of proliferative postmitotic cells described herein and a carrier, optionally a pharmaceutically acceptable excipient. In some embodiments, the compositions further comprise a stabilizer and/or a preservative.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The composition may comprise a pharmaceutically acceptable excipient, a pharmaceutically acceptable salt, diluents, carriers, vehicles and such other inactive agents well known to the skilled artisan. Vehicles and excipients commonly employed in pharmaceutical preparations include, for example, talc, gum Arabic, lactose, starch, magnesium stearate, cocoa butter, aqueous or non-aqueous solvents, oils, paraffin derivatives, glycols, etc. Solutions can be prepared using water or physiologically compatible organic solvents such as ethanol, 1,2-propylene glycol, polyglycols, dimethylsulfoxide, fatty alcohols, triglycerides, partial esters of glycerine and the like. Parenteral compositions may be prepared using conventional techniques that may include sterile isotonic saline, water, 1,3-butanediol, ethanol, 1,2-propylene glycol, polyglycols mixed with water, Ringer's solution, etc. In one aspect, a coloring agent is added to facilitate in locating and properly placing the composition to the intended treatment site.

Compositions may include a preservative and/or a stabilizer. Non-limiting examples of preservatives include methyl-, ethyl-, propyl-parabens, sodium benzoate, benzoic acid, sorbic acid, potassium sorbate, propionic acid, benzalkonium chloride, benzyl alcohol, thimerosal, phenylmercurate salts, chlorhexidine, phenol, 3-cresol, quaternary ammonium compounds (QACs), chlorbutanol, 2-ethoxyethanol, and imidurea.

To control tonicity, the composition can comprise a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride and calcium chloride.

Compositions may include one or more buffers. Typical buffers include: a phosphate buffer; a Tris buffer; a borate buffer; a succinate buffer; a histidine buffer; or a citrate buffer. Buffers will typically be included at a concentration in the 5-20 mM range. The pH of a composition will generally be between 5 and 8, and more typically between 6 and 8 e.g. between 6.5 and 7.5, or between 7.0 and 7.8.

The composition can be administered by any appropriate route, which will be apparent to the skilled person depending on the disease or condition to be treated. Typical routes of administration include intravenous, intra-arterial, intramuscular, subcutaneous, intracranial, intranasal or intraperitoneal.

In some embodiments, the composition may include a cryoprotectant agent. Non-limiting examples of cryoprotectant agents include a glycol (e.g., ethylene glycol, propylene glycol, and glycerol), dimethyl sulfoxide (DMSO), formamide, sucrose, trehalose, dextrose, and any combinations thereof.

The composition can be included in an implantable device. Suitable implantable devices contemplated by this invention include intravascular stents (e.g., self-expandable stents, balloon-expandable stents, and stent-grafts), scaffolds, grafts, and the like. Such implantable devices can be coated on at least one surface, or impregnated, with a composition capable of inducing cell cycle reentry of a postmitotic cell. The composition may also be contained within a reservoir in the implantable device. Where the composition is contained within a reservoir in the implantable device, the reservoir is structured so as to allow the composition to elute from the device. The composition may comprise CDK1, CDK4, CCNB1, CCND1, and AURKB polypeptides, or any combination or equivalents of each thereof. The present disclosure further provides an implantable device that comprises a composition comprising nucleotide sequences encoding CDK1, CDK4, CCNB1, CCND1, and AURKB polypeptides, or any combination or equivalents of each thereof.

The composition can comprise a pharmaceutically acceptable excipient, a pharmaceutically acceptable salt, diluents, carriers, vehicles and such other inactive agents well known to the skilled artisan. Vehicles and excipients commonly employed in pharmaceutical preparations include, for example, talc, gum Arabic, lactose, starch, magnesium stearate, cocoa butter, aqueous or non-aqueous solvents, oils, paraffin derivatives, glycols, etc. Solutions can be prepared using water or physiologically compatible organic solvents such as ethanol, 1,2-propylene glycol, polyglycols, dimethylsulfoxide, fatty alcohols, triglycerides, partial esters of glycerine and the like. Parenteral compositions may be prepared using conventional techniques that may include sterile isotonic saline, water, 1,3-butanediol, ethanol, 1,2-propylene glycol, polyglycols mixed with water, Ringer's solution, etc. In one aspect, a coloring agent is added to facilitate in locating and properly placing the composition to the intended treatment site.

In some embodiments, the formulation is a controlled release formulation. The term "controlled release formulation" includes sustained release and time-release formulations. Controlled release formulations are well-known in the art. These include excipients that allow for sustained, periodic, pulse, or delayed release of the composition. Controlled release formulations include, without limitation, embedding of the composition (cells and/or at least one proliferation and/or cell cycle reentry factor) into a matrix; enteric coatings; micro-encapsulation; gels and hydrogels; implants; and any other formulation that allows for controlled release of a composition.

In one aspect is provided a kit of parts comprising the above-mentioned composition (cells and/or at least one proliferation and/or cell cycle reentry factor), reagents and culture medium. The kit may further comprise a document or an instruction that describes a protocol for growing the cells in culture or for administering to a subject in need thereof.

IV. Methods of Treatment

Cardiovascular Disease

In one aspect is provided methods for treating a cardiovascular disease comprising administering to a subject in need thereof, an effective amount of a composition that increases the expression of CDK1 and CCNB1, or an equivalent of each thereof. In some embodiments, the methods further comprise administering an effective amount of a composition that increases the expression of CDK4, CCND1, or both.

In another aspect is provided methods for treating a cardiovascular disease comprising administering to a subject in need thereof, an effective amount of a population of the proliferative postmitotic cardiac cells (e.g., cardiomyocytes) disclosed herein. In some embodiments, the proliferative cardiomyocytes are modified to overexpress CDK1 and CCNB1, or equivalents thereof. In other embodiments, the proliferative cardiomyocytes are modified to overexpress CDK4, CCND1, or both.

In another aspect is provided methods of treating a cardiovascular disease by administering to a subject in need thereof, an effective amount of a composition comprising proliferation and/or cell cycle reentry factors (e.g., CDK1, CCNB1 and AURKB or equivalents thereof).

In some aspects, a proliferative cardiac cell (e.g., a cardiomyocyte) of the present disclosure can be used to treat a subject in need thereof. In some embodiments, the proliferative cardiac cell can be administered to the subject in need thereof, where administration into the subject of the proliferative cardiac cell, treats a cardiovascular disease in the subject. Thus, in some embodiments, a method of treating cardiovascular disease involves administering to a subject in need thereof a population of cardiac cells induced to proliferate and/or reenter the cell cycle. In other embodiments, a method of treating cardiovascular disease involves administering to the subject in need thereof an effective amount of a composition comprising CDK1, CCNB1 and AURKB or equivalents thereof. In other embodiments, a method of treating cardiovascular disease involves administering to the subject in need thereof an effective amount of a composition comprising CDK1, CDK4, CCNB1, CCND1, or combinations and/or equivalents thereof.

Subjects in need of treatment using the compositions, cells and methods of the present disclosure include, but are not limited to, individuals having a congenital heart defect, individuals suffering from a degenerative muscle disease, individuals suffering from a condition that results in ischemic heart tissue (e.g., individuals with coronary artery disease), and the like. In some examples, a method is useful to treat a degenerative muscle disease or condition (e.g., familial cardiomyopathy, dilated cardiomyopathy, hypertrophic cardiomyopathy, restrictive cardiomyopathy, or coronary artery disease with resultant ischemic cardiomyopathy). In some examples, a subject method is useful to treat individuals having a cardiac or cardiovascular disease or disorder, for example, cardiovascular disease, aneurysm, angina, arrhythmia, atherosclerosis, cerebrovascular accident (stroke), cerebrovascular disease, congenital heart disease, congestive heart failure, myocarditis, valve disease coronary, artery disease dilated, diastolic dysfunction, endocarditis, high blood pressure (hypertension), cardiomyopathy, hypertrophic cardiomyopathy, restrictive cardiomyopathy, coronary artery disease with resultant ischemic cardiomyopathy, mitral valve prolapse, myocardial infarction (heart attack), or venous thromboembolism.

Subjects who are suitable for treatment using the compositions, cells and methods of the present disclosure include individuals (e.g., mammalian subjects, such as humans, non-human primates, experimental non-human mammalian subjects such as mice, rats, etc.) having a cardiac condition including but limited to a condition that results in ischemic heart tissue (e.g., individuals with coronary artery disease) and the like. In some examples, an individual suitable for treatment suffers from a cardiac or cardiovascular disease or condition, e.g., cardiovascular disease, aneurysm, angina, arrhythmia, atherosclerosis, cerebrovascular accident (stroke), cerebrovascular disease, congenital heart disease, congestive heart failure, myocarditis, valve disease coronary, artery disease dilated, diastolic dysfunction, endocarditis, high blood pressure (hypertension), cardiomyopathy, hypertrophic cardiomyopathy, restrictive cardiomyopathy, coronary artery disease with resultant ischemic cardiomyopathy, mitral valve prolapse, myocardial infarction (heart attack), or venous thromboembolism. In some examples, individuals suitable for treatment with a subject method include individuals who have a degenerative muscle disease, e.g., familial cardiomyopathy, dilated cardiomyopathy, hypertrophic cardiomyopathy, restrictive cardiomyopathy, or coronary artery disease with resultant ischemic cardiomyopathy.

Neurological Disease

In one aspect is provided methods for treating a neurological disease comprising administering to a subject in need thereof an effective amount of a composition that increases the expression of CDK1 and CCNB1, or equivalents of each thereof. In some embodiments, the methods further comprise administering an effective amount of a composition that increases the expression of CDK4, CCND1, or both.

In another aspect is provided methods for treating a neurological disease comprising administering to a subject in need thereof, an effective amount of a population of the proliferative postmitotic neural cells (e.g., neurons) disclosed herein. In some embodiments, the proliferative neural cells are modified to overexpress CDK1 and CCNB1, or equivalents thereof. In other embodiments, the proliferative neural are modified to overexpress CDK4, CCND1, or both.

In another aspect is provided methods of treating a neurological disease by administering to a subject in need thereof, an effective amount of a composition comprising proliferation and/or cell cycle reentry factors (e.g., CDK1, CCNB1 and AURKB or equivalents thereof).

In some aspects, a proliferative neural cell (e.g., a neuron) of the present disclosure can be used to treat a subject in need thereof. In some embodiments, the proliferative neural cell can be administered to the subject in need thereof, where administration into the subject of the proliferative neural cell, treats a neurological disease in the subject. Thus, in some embodiments, a method of treating a neural disease involves administering to a subject in need thereof a population of neural cells induced to proliferate and/or reenter the cell cycle. In other embodiments, a method of treating a neural disease involves administering to the subject in need thereof an effective amount of a composition comprising CDK1, CCNB1 and AURKB or equivalents thereof. In other embodiments, a method of treating a neural disease involves administering to the subject in need thereof an effective amount of a composition comprising CDK1, CDK4, CCNB1, CCND1, or combinations and/or equivalents thereof.

Subjects in need of or suitable for treatment using the compositions, cells and methods of the present disclosure include, but are not limited to, individuals having a spinal cord injury (SCI), amyotrophic lateral sclerosis (ALS), dural arteriovenous fistulae, epilepsy, memory disorders, multiple sclerosis (MS), Parkinson's disease, peripheral neuropathy, Alzheimer's disease, post-herpetic neuralgia, spinal cord tumor, and stroke.

Pancreatic Disease

In one aspect is provided methods for treating a pancreatic disease comprising administering to a subject in need thereof an effective amount of a composition that increases the expression of CDK1 and CCNB1, or equivalents of each thereof. In some embodiments, the methods further comprise administering an effective amount of a composition that increases the expression of CDK4, CCND1, or both.

In another aspect is provided methods for treating a pancreatic disease comprising administering to a subject in need thereof, an effective amount of a population of the proliferative postmitotic pancreatic cells (e.g., beta cell) disclosed herein. In some embodiments, the proliferative pancreatic cells are modified to overexpress CDK1 and CCNB1, or equivalents thereof. In other embodiments, the proliferative pancreatic cells are modified to overexpress CDK4, CCND1, or both.

In another aspect is provided methods of treating a pancreatic disease by administering to a subject in need thereof, an effective amount of a composition comprising proliferation and/or cell cycle reentry factors (e.g., CDK1, CCNB1 and AURKB or equivalents thereof).

In some aspects, a proliferative pancreatic cell (e.g., a beta cell) of the present disclosure can be used to treat a subject in need thereof. In some embodiments, the proliferative pancreatic cell can be administered to the subject in need thereof, where administration into the subject of the proliferative pancreatic cell, treats a pancreatic disease in the subject. Thus, in some embodiments, a method of treating a pancreatic disease involves administering to a subject in need thereof a population of pancreatic cells induced to proliferate and/or reenter the cell cycle. In other embodiments, a method of treating a pancreatic disease involves administering to the subject in need thereof an effective amount of a composition comprising CDK1, CCNB1 and AURKB or equivalents thereof. In other embodiments, a method of treating a pancreatic disease involves administering to the subject in need thereof an effective amount of a composition comprising CDK1, CDK4, CCNB1, CCND1, or combinations and/or equivalents thereof.

Subjects in need of or suitable for treatment using the compositions, cells and methods of the present disclosure include, but are not limited to, individuals having diabetes mellitus (e.g., type 1 diabetes or type 2 diabetes), acute pancreatitis, chronic pancreatitis, hereditary pancreatitis, pancreatic cancer, cystic fibrosis, and congenital malformations.

Hearing Loss

In one aspect is provided methods for treating hearing loss comprising administering to a subject in need thereof an effective amount of a composition that increases the expression of CDK1 and CCNB1, or equivalents of each thereof. In some embodiments, the methods further comprise administering an effective amount of a composition that increases the expression of CDK4, CCND1, or both.

In another aspect is provided methods for treating hearing loss comprising administering to a subject in need thereof, an effective amount of a population of the proliferative postmitotic hair cells of the ear disclosed herein. In some embodiments, the proliferative hair cells are modified to overexpress CDK1 and CCNB1, or equivalents thereof. In other embodiments, the proliferative hair cells are modified to overexpress CDK4, CCND1, or both.

In another aspect is provided methods of treating hearing loss by administering to a subject in need thereof, an effective amount of a composition comprising proliferation and/or cell cycle reentry factors (e.g., CDK1, CCNB1 and AURKB or equivalents thereof).

In some aspects, a proliferative hair cell (e.g., hair cell of the inner ear) of the present disclosure can be used to treat a subject in need thereof. In some embodiments, the proliferative hair cell can be administered to the subject in need thereof, where administration into the subject of the proliferative hair cell, treats hearing loss in the subject. Thus, in some embodiments, a method of treating hearing loss involves administering to a subject in need thereof a population of hair cells induced to proliferate and/or reenter the cell cycle. In other embodiments, a method of treating hearing loss involves administering to the subject in need thereof an effective amount of a composition comprising CDK1, CCNB1 and AURKB or equivalents thereof. In other embodiments, a method of treating hearing loss involves administering to the subject in need thereof an effective amount of a composition comprising CDK1, CDK4, CCNB1, CCND1, or combinations and/or equivalents thereof.

Subjects in need of or suitable for treatment using the compositions, cells and methods of the present disclosure include, but are not limited to, individuals having hearing loss caused by head trauma, viruses or disease, exposure to loud noises, autoimmune inner ear diseases, hereditary disorders, aging (presbycusis), malformation of the inner ear, and Meniere's disease.

Skeletal Muscle

In one aspect is provided methods for increasing muscle mass comprising administering to a subject in need thereof an effective amount of a composition that increases the expression of CDK1 and CCNB1, or equivalents of each thereof. In some embodiments, the methods further comprise administering an effective amount of a composition that increases the expression of CDK4, CCND1, or both.

In another aspect is provided methods for increasing muscle mass comprising administering to a subject in need thereof, an effective amount of a population of the proliferative postmitotic skeletal muscle cells disclosed herein. In some embodiments, the proliferative skeletal muscle cells are modified to overexpress CDK1 and CCNB1, or equivalents thereof. In other embodiments, the skeletal muscle cells are modified to overexpress CDK4, CCND1, or both.

In another aspect is provided methods of increasing muscle mass by administering to a subject in need thereof, an effective amount of a composition comprising proliferation and/or cell cycle reentry factors (e.g., CDK1, CCNB1 and AURKB or equivalents thereof).

In some aspects, a proliferative skeletal muscle cell of the present disclosure can be used to treat a subject in need thereof. In some embodiments, the proliferative skeletal muscle cell can be administered to the subject in need thereof, where administration into the subject of the skeletal muscle cell, builds muscle mass in the subject by increasing the number of skeletal muscle cells. Thus, in some embodiments, a method of building muscle mass involves administering to a subject in need thereof a population of skeletal muscle cells induced to proliferate and/or reenter the cell cycle. In other embodiments, a method of building muscle mass involves administering to the subject in need thereof an effective amount of a composition comprising CDK1, CCNB1 and AURKB or equivalents thereof. In other embodiments, a method of building muscle mass involves administering to the subject in need thereof an effective amount of a composition comprising CDK1, CDK4, CCNB1, CCND1, or combinations and/or equivalents thereof.

Subjects in need of or suitable for use of the compositions, cells and methods of the present disclosure include, but are not limited to, individuals having a skeletal muscle disease such as muscular dystrophy, cerebral palsy, amyotrophic lateral sclerosis, and myasthenia gravis or individuals that desire an increase in muscle mass, such as weight lifters and bodybuilders.

Unless stated otherwise, the abbreviations used throughout the specification have the following meanings:

Aa=amino acid(s)
Bp=base pair(s)
H=hour(s)
G=gram(s)
Kb=kilobase
kDa=kiloDalton
Kg=kilogram
L=liter
LC=liquid chromatography
Mg=milligram
Min=minute
mL=milliliter
mM=millimolar
nM=nanomolar
nT=nucleotide(s)
pM=picomolar
s.d.=standard deviation
μCi=microcurie
Mg=microgram
μL=microliter
μM=micromolar
Mm=micrometer
° C.=degree Celsius These one-letter symbols have the following meaning when representing amino acids:

A=Alanine
R=Arginine
N=Asparagine
D=Aspartic acid
C=Cysteine
E=Glutamic acid
Q=Glutamine
G=Glycine
H=Histidine
I=Isoleucine
L=Leucine
K=Lysine
M=Methionine
F=Phenylalanine
P=Proline
S=Serine
T=Threonine
W=Tryptophan
Y=Tyrosine
V=Valine

EXAMPLES

The following examples are intended to further illustrate certain embodiments of the disclosure. The examples are put forth so as to provide one of ordinary skill in the art and are not intended to limit its scope.

Example 1. Induction of Proliferation in Non-Proliferative Cardiomyocytes

Cardiomyocyte Cell Culture:

Mouse cardiomyocytes were isolated from neonatal (newborn P0) and adult (6 week-old) as described in Ieda et al. (2009) *Dev. Cell* 16(2): 233-244. Cardiomyocytes were cultured in DMEM/M199 medium containing 10% FBS.

Microarray Protocol:

Mouse genome-wide gene expression analyses were performed using Affymetrix Mouse Gene 1.0 ST Array. RNA was extracted from neonatal (newborn P0) and adult (6 week-old) cardiomyocytes using Trizol (Invitrogen). Microarray analyses were performed in triplicate from independent biologic samples, according to the standard Affymetrix Genechip protocol. Data were analyzed using the Affymetrix Power Tool (APT, version 1.8.5). Differential gene expression was defined using the statistics/threshold combination.

Overexpression:

Adenoviruses were constructed according to Mohamed et al., Cardiovasc Res. 2014 Jul. 1; 103(1):47-59. Briefly, the coding regions of EGFP, CDK1, CCNB1 and AURKB were amplified by PCR and subcloned into pENTR™/SD/D-TOPO shuttle vector. Adenoviruses were generated by homologues recombination between the pENTR™/SD/D-TOPO shuttle vector and pAd/CMVN5-DEST vector (Life Technologies) using the Gateway® cloning system following the manufacturer's recommended methods. The adenovirus particles were produced by transfecting the adenovirus encoding plasmid into HEK293 cells and purified using Cesium Chloride column and titrated. To infect the cardiomyocytes 25 multiplicity of infection (MOI) of the adenovirus were incubated for 24 hours and then the medium was replaced with fresh medium.

Immunocytochemistry:

Cells were fixed in 4% paraformaldehyde for 15 min at room temperature, permeabilized with Saponin, blocked, and incubated with primary antibodies against Troponin T (cTnT) (Thermo Scientific), phospho histone H3 (PHH3) (Life Technologies), then with secondary antibodies conjugated with Alexa 488 (green) or 594 (red) (Molecular Probes), and 4',6-diamidino-2-phenylindole (DAPI) (Invitrogen).

Histology:

For Masson's trichrome staining, hearts were harvested 6 weeks following myocardial infarction and embedded in paraffin and transversely sectioned. Deparaffinized sections were dipped sequentially into Weigert's iron hematoxylin working solution for 10 min, Biebrich scarlet-acid fuchsin solution for 15 min, phosphomolybdic-phosphotungstic acid solution for 15 min, aniline blue solution 5-10 min, and 1% acetic acid solution for 2-5 min. For immunohistochemical studies in cell-injected hearts, hearts were fixed in 0.4% paraformaldehyde overnight, embedded in OCT compound, and frozen in liquid nitrogen (Ieda et al., 2010; Ieda et al., 2009). Hearts were cut vertically in 7-μm sections to show both ventricles. Sections were stained with primary antibodies against PHH3 (S10) and Troponin T (cTnT), with secondary antibodies conjugated with Alexa 488 or 594, and DAPI.

Proliferation and Cell Count Assays:

Two month old hiPSC-derived cardiomyocytes overexpressing CDK1, CCNB1 and AURKB or a control adenoviral vector were grown in culture. EdU (5-ethynyl-2'-deoxyuridine; 10 μM) was administered to culture medium for 30 minutes. The incorporation of EdU was detected using the Click-iT EdU Cell Proliferation Assay Kit (Invitrogen Inc.) and analysed by microscopy.

The number of cardiomyocyte proliferating nuclei for two month old hiPSC-derived cardiomyocytes transduced with a control or CDK1, CCNB1 and AURKB adenovirus were quantified by assessing total nuclei counts per image using immunofluorescence for DAPI-positive cells.

Total cell numbers in populations of hiPSC-derived cardiomyocytes transduced with either a control or CDK1, CCNB1 and AURKB for 72 hours were determined by FACS analysis. Cells were harvested from cultured dishes and analyzed on a FACS Calibur (BD Biosciences) with FlowJo software.

Cell number and viability were also analyzed using Cell Titre Glo (Promega, Madison, Wis., USA). Cell Titre Glo is a highly sensitive indicator for cell number and viability through the measurement of ATP metabolism, without the need to detach the cells from the culture plate as is required in FACS. Following incubation of control cells or cells transduced with CDK1, CCNB1 and AURKB with the Cell Titre Glo reagent, luminescent intensities of the wells containing Cell Titre Glo were recorded, with the intensity being proportional to the number of viable metabolizing cells in the well.

Time Lapse Imaging:

Cardiomyocytes transduced with adenovirus to overexpress CDK1, CCNB1 and AURKB were plated into 24-well plates (10,000 cells per well) in quadruplicate and analyzed for cell proliferation using the IncuCyte imager (Essen BioSciences, Ann Arbor, Mich., USA). The plates were scanned in the IncuCyte at 1-hour intervals for 4 days. The data were analyzed with the IncuCyte software.

Animal Studies:

CDK1AF, CCNB1, and AURKB or GFP control adenovirus were injected into C57bl6/N hearts at the site of injury following myocardial infarction (MI) as described in Qian et al., (2014) *Nature* 485(7400):593-8, Saxena et al. (2008) *Circulation* 117: 2224-2231. Hearts were harvested five days post infarct to evaluate cell proliferation or six weeks post infarct to evaluate cardiac function and for histology.

Echocardiography:

Systolic function was assessed with the use of 2-dimensional measurements to measure ejection fraction (EF) in mice infected with CDK1AF, CCNB1 and AURKB or GFP control adenovirus. Mice were anesthetized with 1.75% isoflurane. Core temperature was maintained at 37-38° C., and scans were performed in a random-blind fashion. Percent ejection fraction (% EF) and decline in EF over time were measured. Each mouse underwent three separate scans on day 3-, 10-, 24- and 40-days post infarction.

Results

Cell Cycle Genes are Differentially Regulated Between Neonatal and Adult Cardiomyocytes To select potential factors that induce cardiac cell proliferation and/or cell cycle reentry, microarray analysis was performed to identify cell cycle genes differentially expressed between neonatal (newborn P0) and adult (6 week-old) mouse cardiomyocytes. Representative cell cycle genes differentially expressed between proliferative (neonatal) and non-proliferative (adult) cardiomyocytes are shown in FIG. 1.

Figure 2:
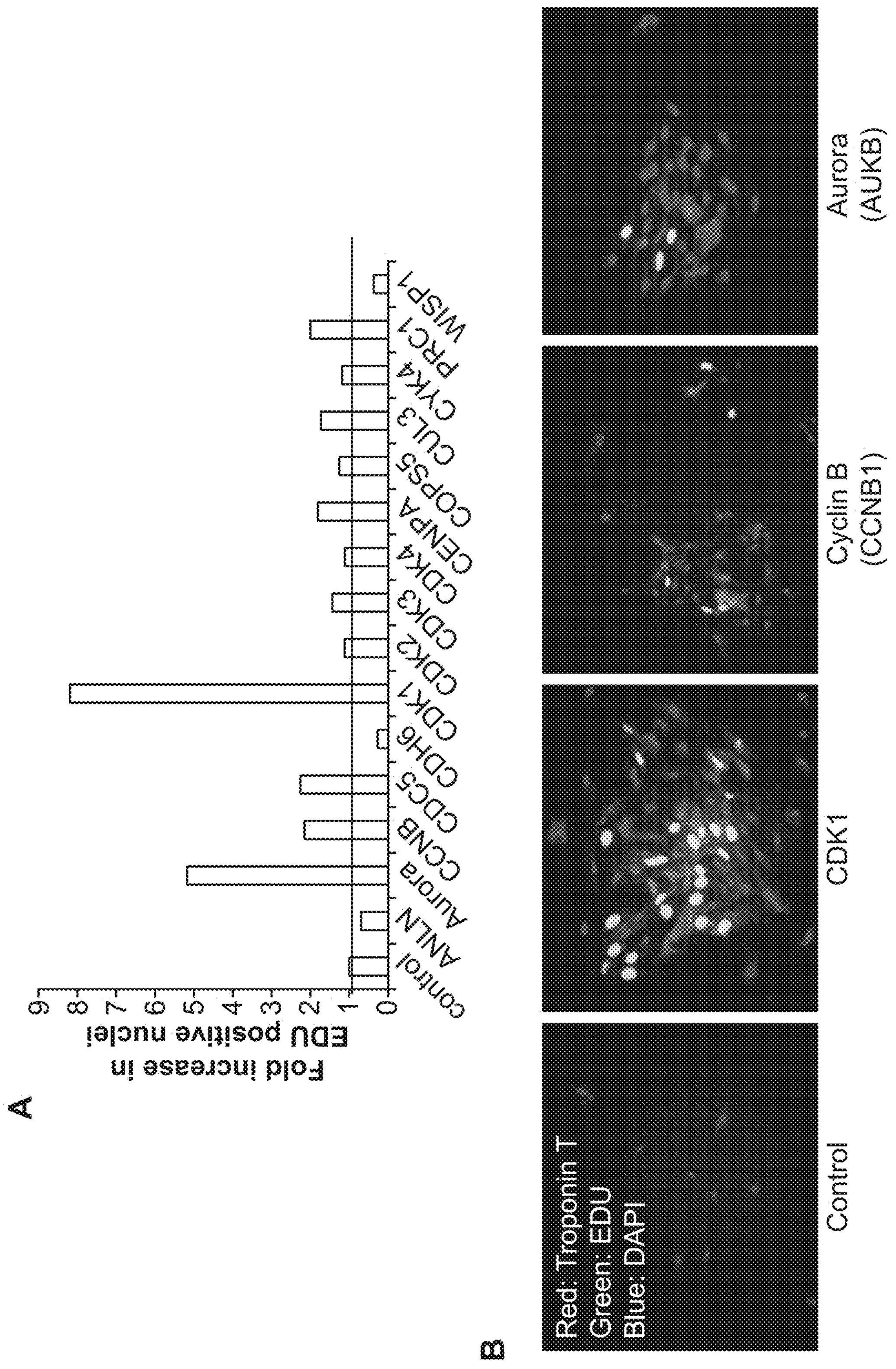
FIG. 2 demonstrates that overexpression of several of the top differentially regulated genes between proliferative (neonatal) and non-proliferative (adult) cardiac cells promote cardiac cell proliferation in mouse cardiomyocytes (panel A). Cardiomyocytes transduced with a control, CDK1, CCNB1, or AURKB expressing adenovirus were stained with EDU proliferation marker, Troponin T cardiac marker and DAPI nuclear stain. All three genes enhanced cardiac proliferation (panel B).

CDK1, CCNB1 and AURKB Promote Cardiac Cell Proliferation in Mouse and Human Cardiomyocytes The top fifteen down-regulated cell cycle genes in adult cardiomyocytes were tested to determine whether overexpression of any one gene could increase proliferation and/or cell cycle reentry detected by EdU incorporation. Cardiomyocytes overexpressing AURKB (Aurora), CCNB1, CDC5, CDK1, CDK2, CDK3, CENPA, COPS5, CUL3, CYK4, and PRC1 showed increased EdU incorporation (FIG. 2, panel A). On the other hand, overexpression of ANLN, CDH6 and WISP1 showed a decrease in EdU incorporation as compared to the control (FIG. 2, panel A). The proliferative cells ($EdU^+$) also stained positive for the cardiac cell marker cardiac troponin T (cTnT) (FIG. 2, panel B).

Figure 3:
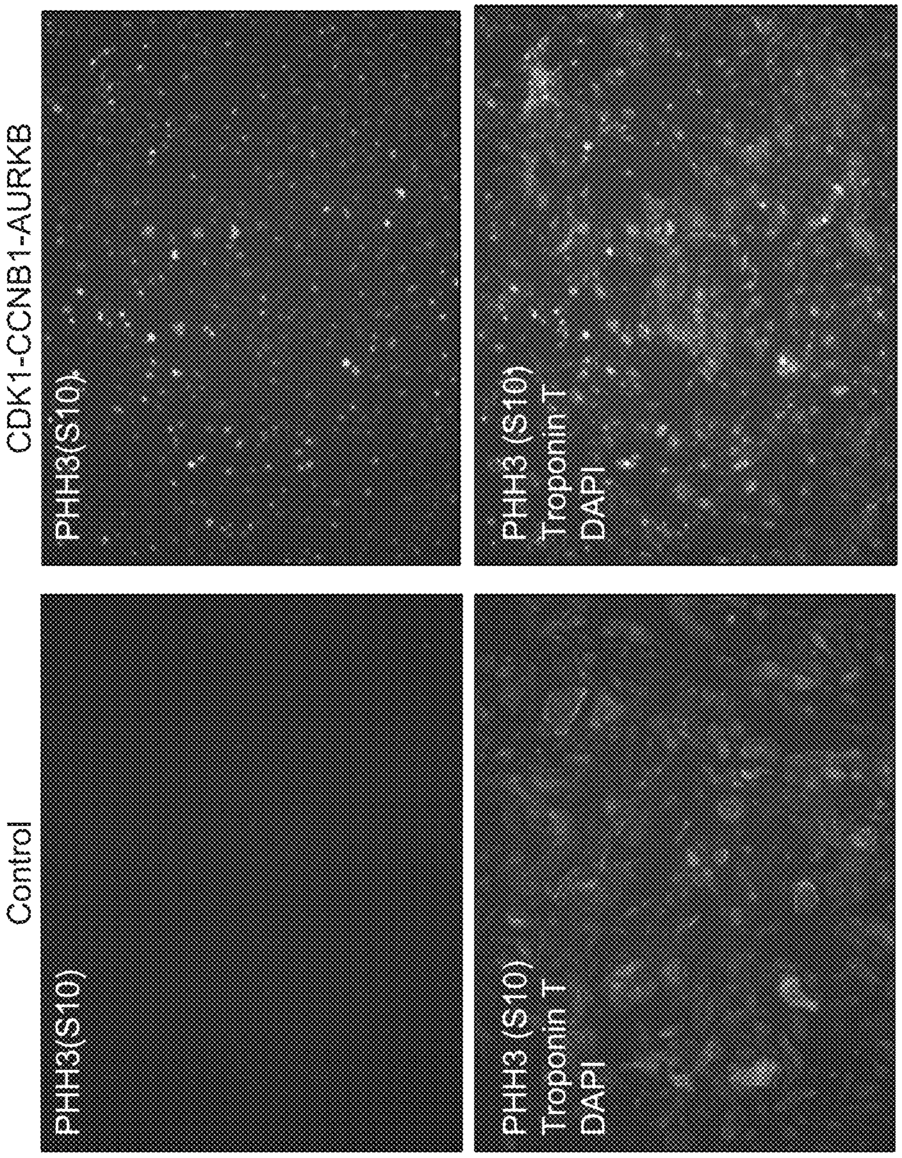
FIG. 3 demonstrates that overexpression of CDK1, CCNB1 and AURKB promote cardiac cell proliferation in human induced pluripotent stem cell (hiPSC)-derived cardiomyocytes. Human iPSC-derived cardiomyocytes overexpressing CDK1, CCNB1 and AURKB show increased expression of the proliferation marker phospho histone H3 (PHH3).
Figure 7:
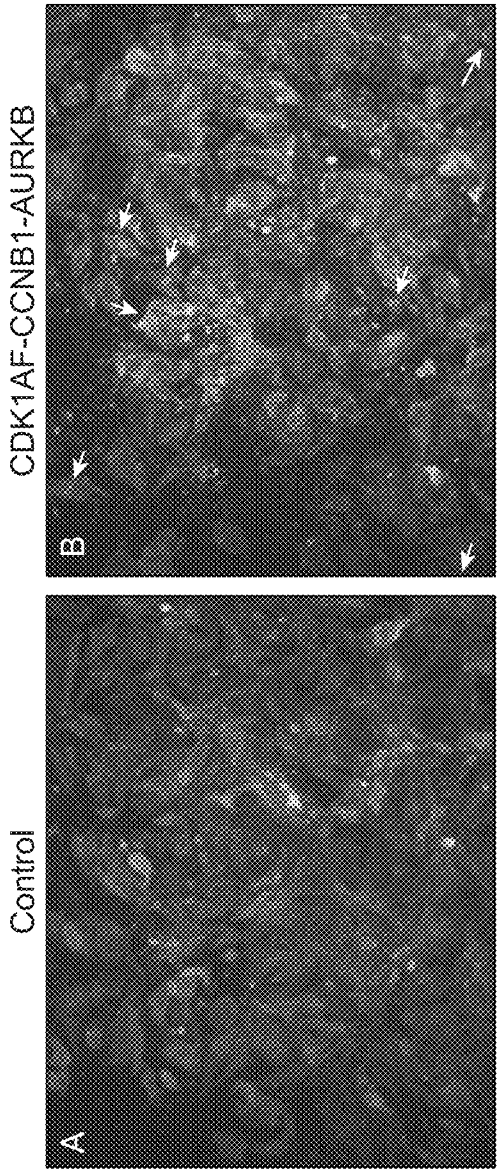
FIG. 7 demonstrates that overexpression of constitutively active CDK1 (CDK1AF), CCNB1 and AURKB promote cardiac cell proliferation in mouse primary cardiomyocytes. Images are representative images of adult mouse cardiomyocytes transduced with a control vector (panel A) or CDK1AF, CCNB1 and AURKB (panel B) and stained with phospho histone H3 (PHH3). Arrows denote dividing cells.

It was next tested whether three factors (CDK1, CCNB1 and AURKB) used in combination are sufficient to induce proliferation of non-proliferative hiPSC-derived cardiomyocytes. CDK1, CCNB1 and AURKB were introduced into hiPSC-derived cardiomyocytes by adenovirus. Phospho histone H3 (S10)-positive cells were not observed in control cells. In contrast, cells overexpressing CDK1, CCNB1 and AURKB for 72 hours showed an increase in phospho histone H3 expression (FIG. 3). Similarly, when a constitutively active CDK1 (CDK1AF) as well as CCNB1 and AURKB were introduced into cardiomyocytes with no proliferative capacity, isolated from 7 day-old mice there was an increase in phospho histone H3 expression as compared to cells transduced with a control adenovirus (FIG. 7).

Overexpression of CDK1, CCNB1 and AURKB Increase Cardiomyocyte Cell Number

Figure 4:
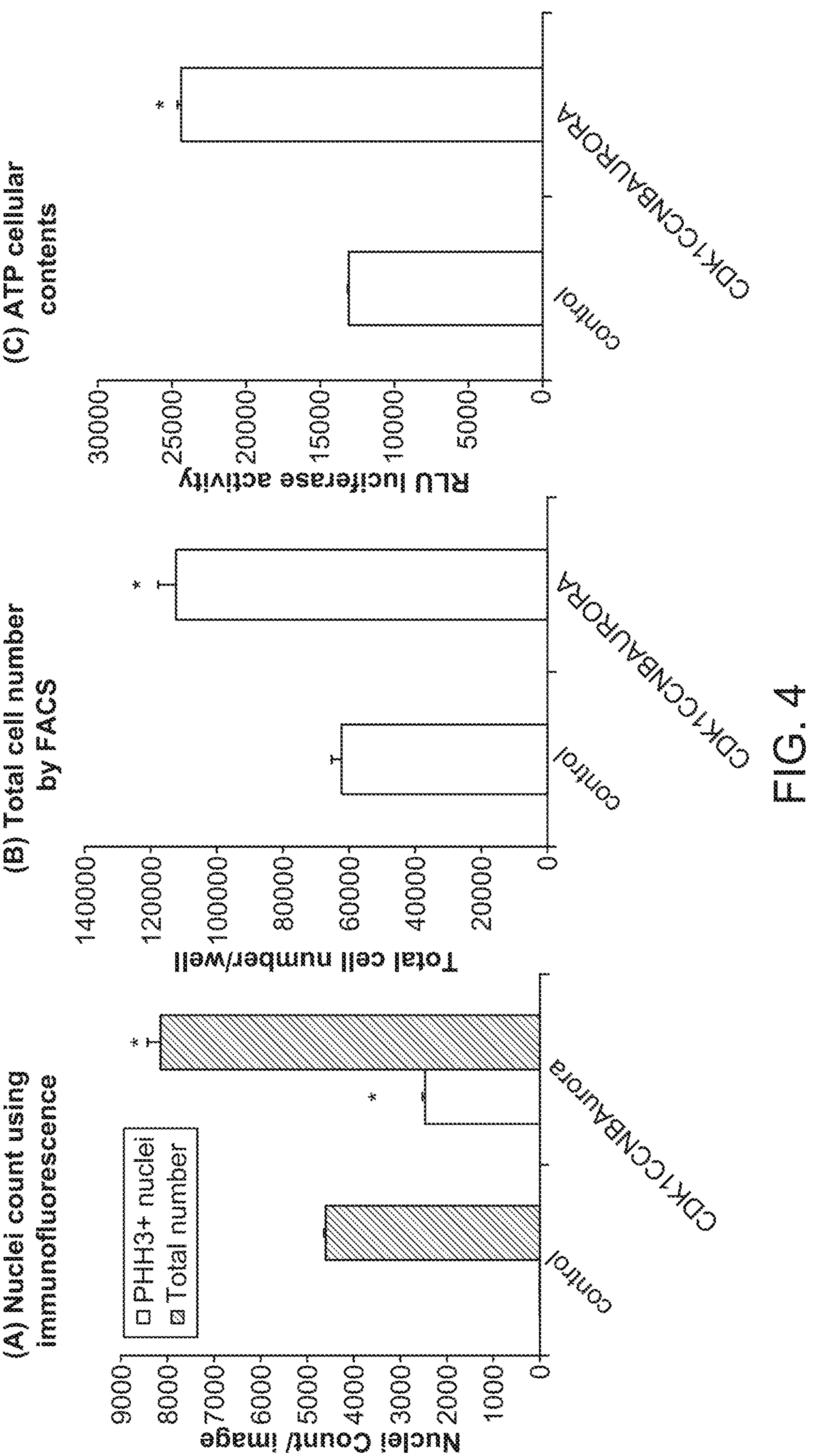
FIG. 4 shows increase in cardiomyocytes number following overexpression of CDK1, CCNB1 and AURKB for 72 hours in hiPSC-derived cardiomyocytes using three different techniques to quantify cardiomyocyte cell number. Panel A shows cell doubling in the total number of nuclei in response to overexpression of CDK1, CCNB1 and AURKB and approximately 30% of total nuclei stained positive for PHH3. Fluorescence activated cell sorting (FACS) also revealed an increase in total cell number following overexpression of CDK1, CCNB1, and AURKB in hiPSC-derived cardiomyocytes (panel B). An ATP cellular content analysis showed a two-fold increase in cell number following overexpression of CDK1, CCNB1 and AURKB in hiPSC-derived cardiomyocytes (n=3, *$p<0.05$) (panel C).

Next, quantification of cell number in populations of cardiomyocytes overexpressing CDK1, CCNB1 and AURKB was performed. Three independent methods were used. Quantification of proliferating cardiomyocyte nuclei showed that there is doubling in the number of nuclei in response to overexpression of CDK1, CCNB1 and AURKB for 72 hours (FIG. 4, panel A). In addition, 30% of the total nuclei stained positive for PHH3. FACS analysis showed that the cell number in populations of cardiomyocytes overexpressing CDK1, CCNB1 and AURKB increased by 2-fold compared to the control (FIG. 4, panel B). To test for cell number and cell viability without the need to detach cells from the culture dish, as required by FACS, ATP Glo assays were performed. Using this method, a 2-fold increase in the cell number following overexpression of CDK1, CCNB1 and AURKB for 72 hours was observed—similar to that reported in FACS analysis (FIG. 4, panel C).

Figure 5:
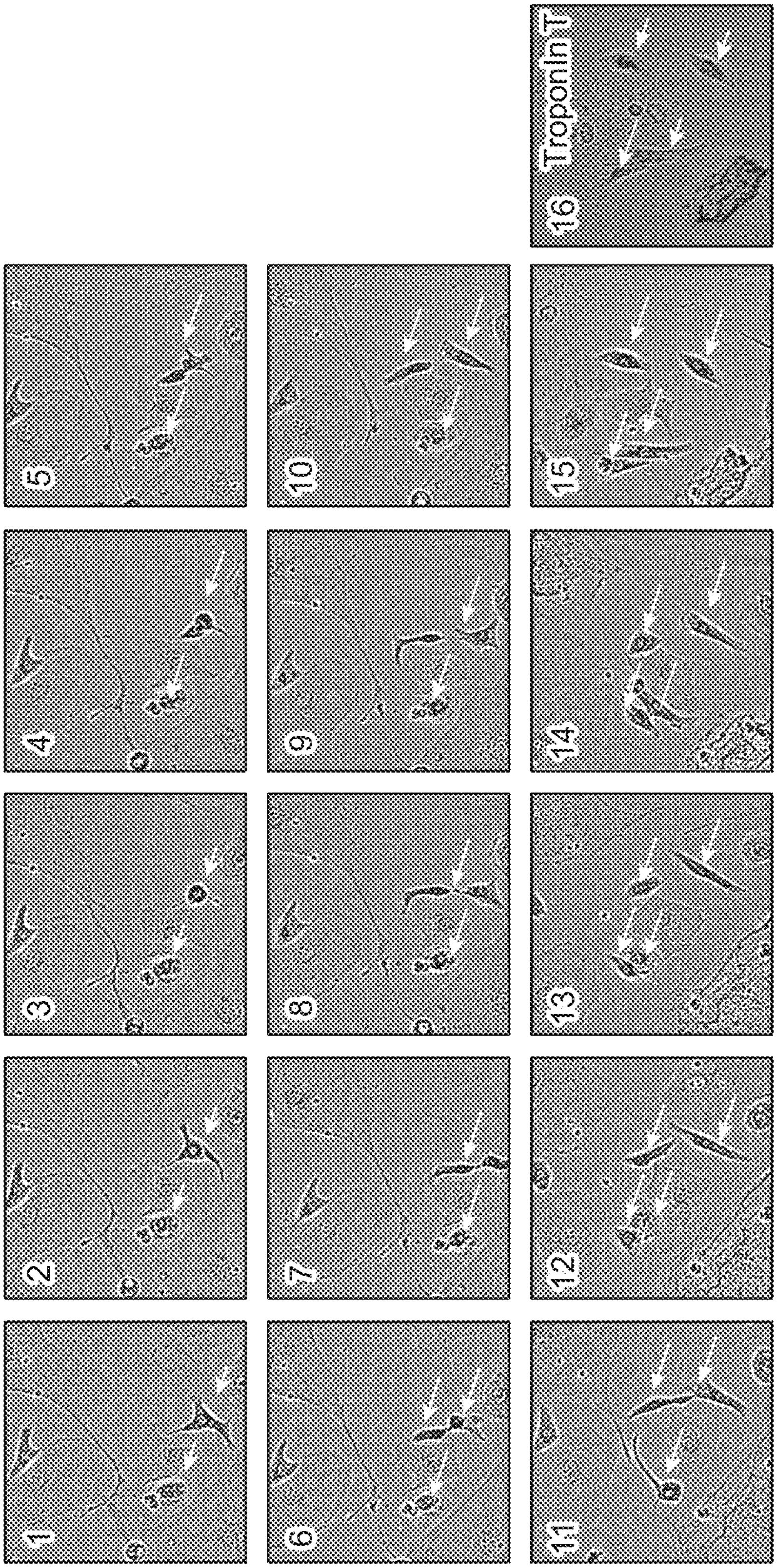
FIG. 5 depicts time lapse imaging of cell division in hiPSC-derived cardiomyocytes overexpressing CDK1, CCNB1 and AURKB. Panels 1-15 are representative images collected every hour for four days. Panel 16 shows that cells at the end of the imaging period stain positive for cardiac marker Troponin T. Arrows denote two dividing cells and their progeny.
Figure 6:
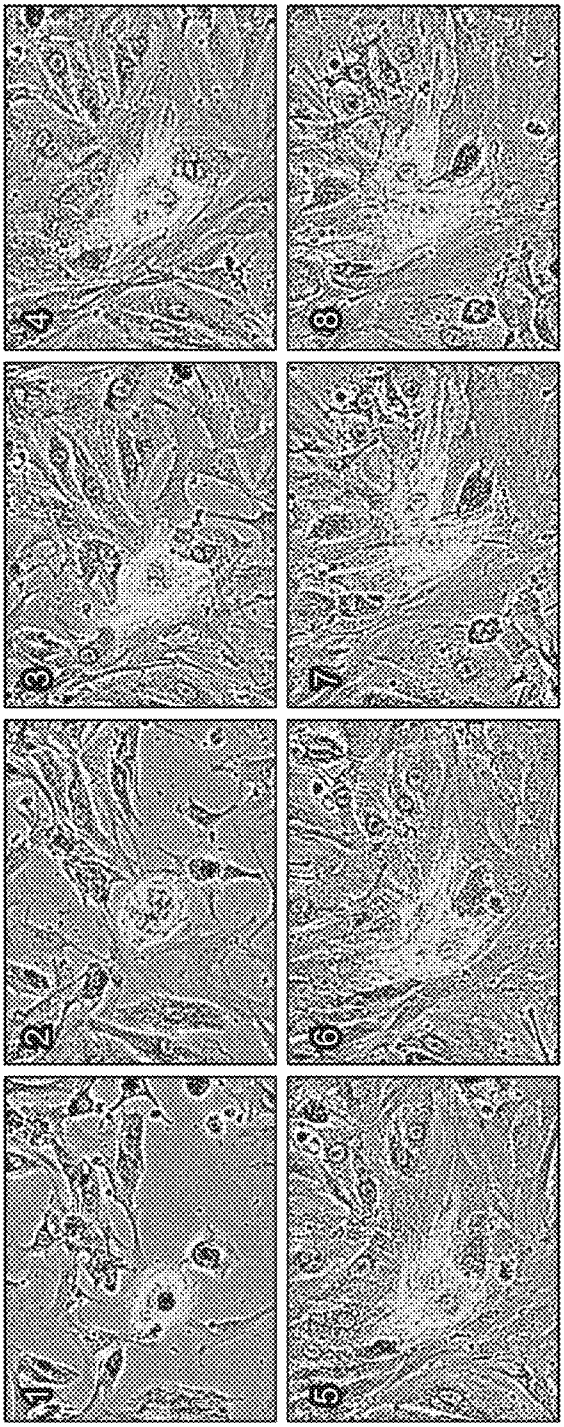
FIG. 6 depicts time lapse imaging of cell division in adult mouse cardiomyocytes isolated from α-MHC-GFP mice overexpressing constitutively active CDK1 (CDK1AF), CCNB1 and AURKB. Panels 1-8 are representative images collected every hour for four days showing cell division of a cardiomyocyte.

Time lapse imaging was performed to further assess the induction of cardiomyocyte proliferation by overexpression of CDK1, CCNB1 and AURKB. Images were collected hourly over the course of 4 days. Cell divisions were observed in both mouse and human cardiomyocytes overexpressing CDK1, CCNB1 and AURKB (FIGS. 5 and 6).

Together these data demonstrated that non-proliferative adult cardiomyocytes can be induced to proliferate and/or reenter the cell cycle by overexpressing cell cycle genes such as CDK1, CCNB1 and AURKB.

Figure 8:
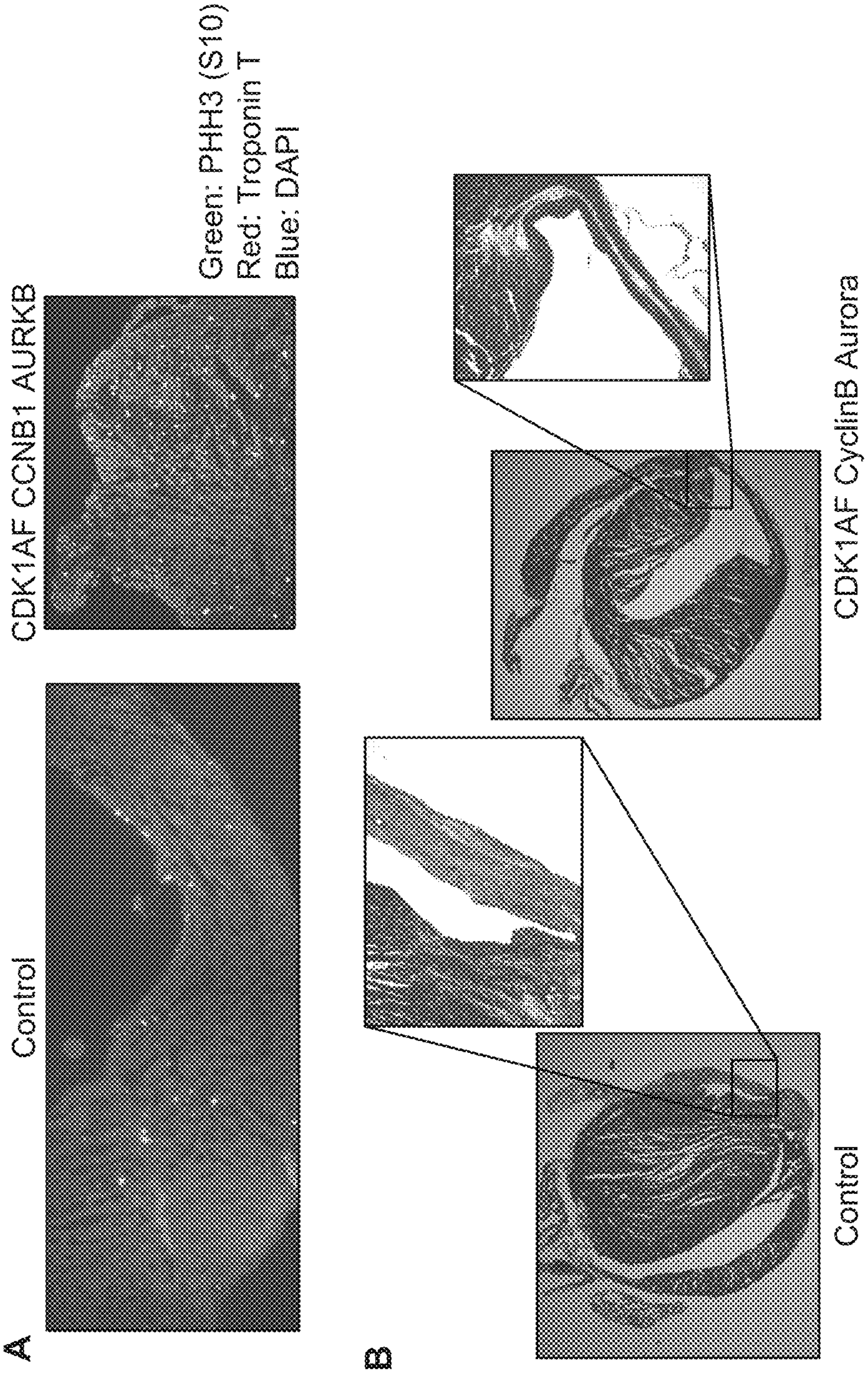
FIG. 8 shows results from a proof of principle study in mice. CDK1AF, CCNB1 and AURKB or GFP adenovirus were injected in c57bl6/N hearts at the site of injury following myocardial infarction (MI). Hearts were either harvested five days post infarct (panel A) to evaluate cell proliferation (PHH3 staining) or six weeks post infarct (panel B) to evaluate cardiac function and histology. Hearts harvested at six weeks following MI were fixed and stained for fibrosis using Masson Trichrome stain.

CDK1, CCNB1 and AURKB Improve Cardiac Function and Structure after Myocardial Infarction To determine whether inducing cardiomyocyte proliferation with overexpression of CDK1, CCNB1 and AURKB is beneficial after myocardial injury CDK1AF, CCNB1 and AURKB adenovirus or control GFP adenovirus was injected into mice at the site of injury following myocardial infarction. At 5 days post-infarct, hearts showed increased proliferation at the site of injury in CDK1AF, CCNB1 and AURKB injected hearts as compared to the control GFP injected heart (FIG. 8, panel A). In addition, at 6 weeks post-infarct, three out of five hearts injected with CDK1AF, CCNB1 and AURKB demonstrated a significant amount of cardiomyocytes within the infarct area compared to the GFP control (FIG. 8, panel B).

Figure 9:
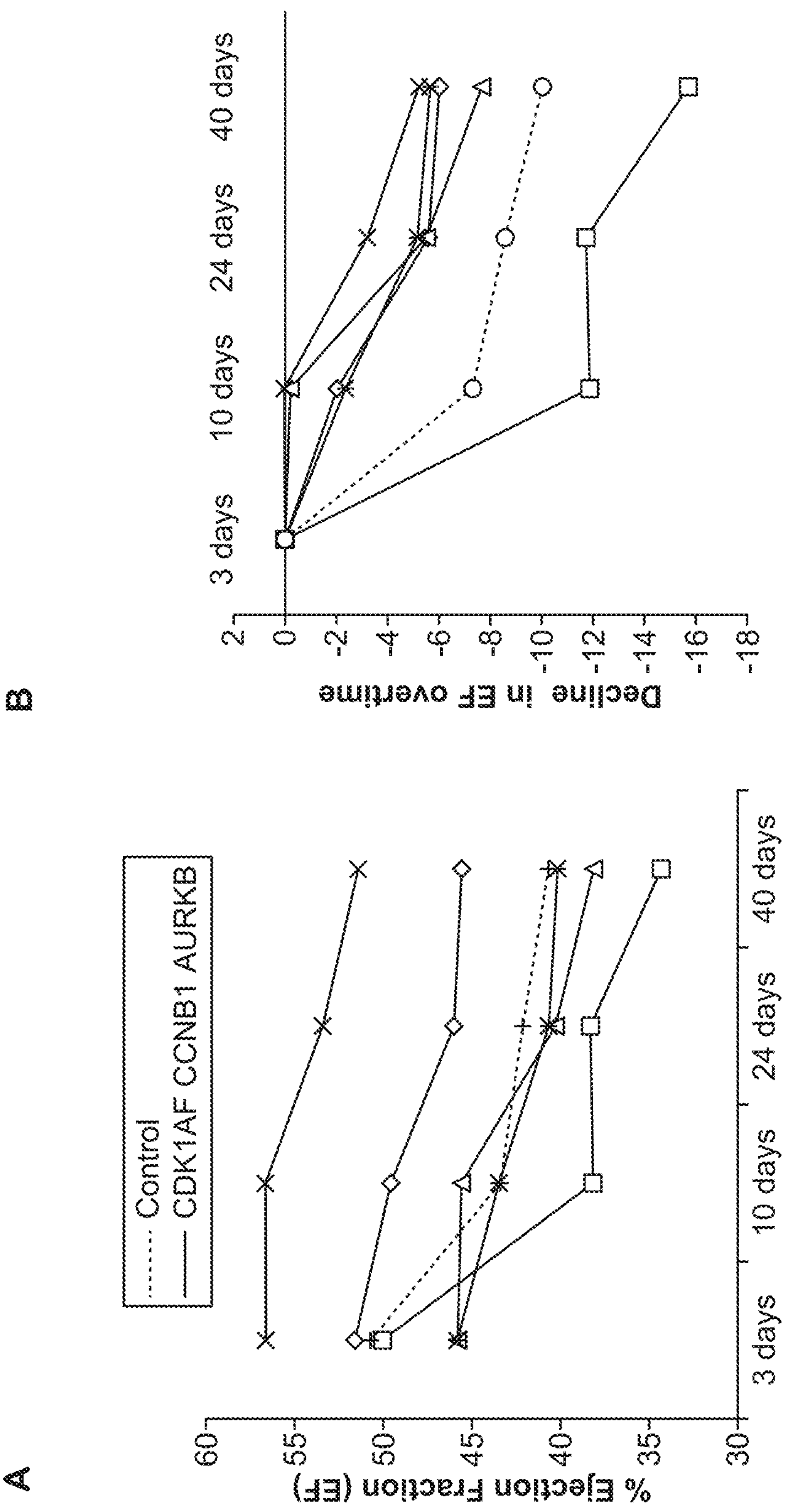
FIG. 9 shows results from the cardiac function assessment for the proof of principle study in mice. CDK1AF, CCNB1 and AURKB or GFP control adenovirus were injected in c57bl6/N hearts at the site of injury following myocardial infarction (MI). The animals were followed by echocardiography to assess the heart function 3-, 10-, 24- and 40-days post MI by measuring % ejection fraction (panel A) and decline in ejection fraction over time (panel B).

To assess cardiac function, animals were injected with either CDK1AF, CCNB1 and AURKB or GFP control adenovirus. The animals were followed by echocardiography to assess the heart function at 3-, 10-, 24- and 40-days post-infarct. Only one out of five controls survived. On the other hand, five out of seven mice injected with CDK1AF, CCNB1 and AURKB survived (FIG. 9, panel A). In addition, four out of five mice injected with CDK1AF, CCNB1 and AURKB showed less deterioration in cardiac function overtime compared to the only survivor control (FIG. 9, panel B).

These in vivo data demonstrated that adult cardiomyocytes induced to proliferate and/or reenter the cell cycle can improve cardiac function and structure after myocardial infarction.

Example 2. Induction of Proliferation in Postmitotic Human Cardiomyocytes

Figure 10:
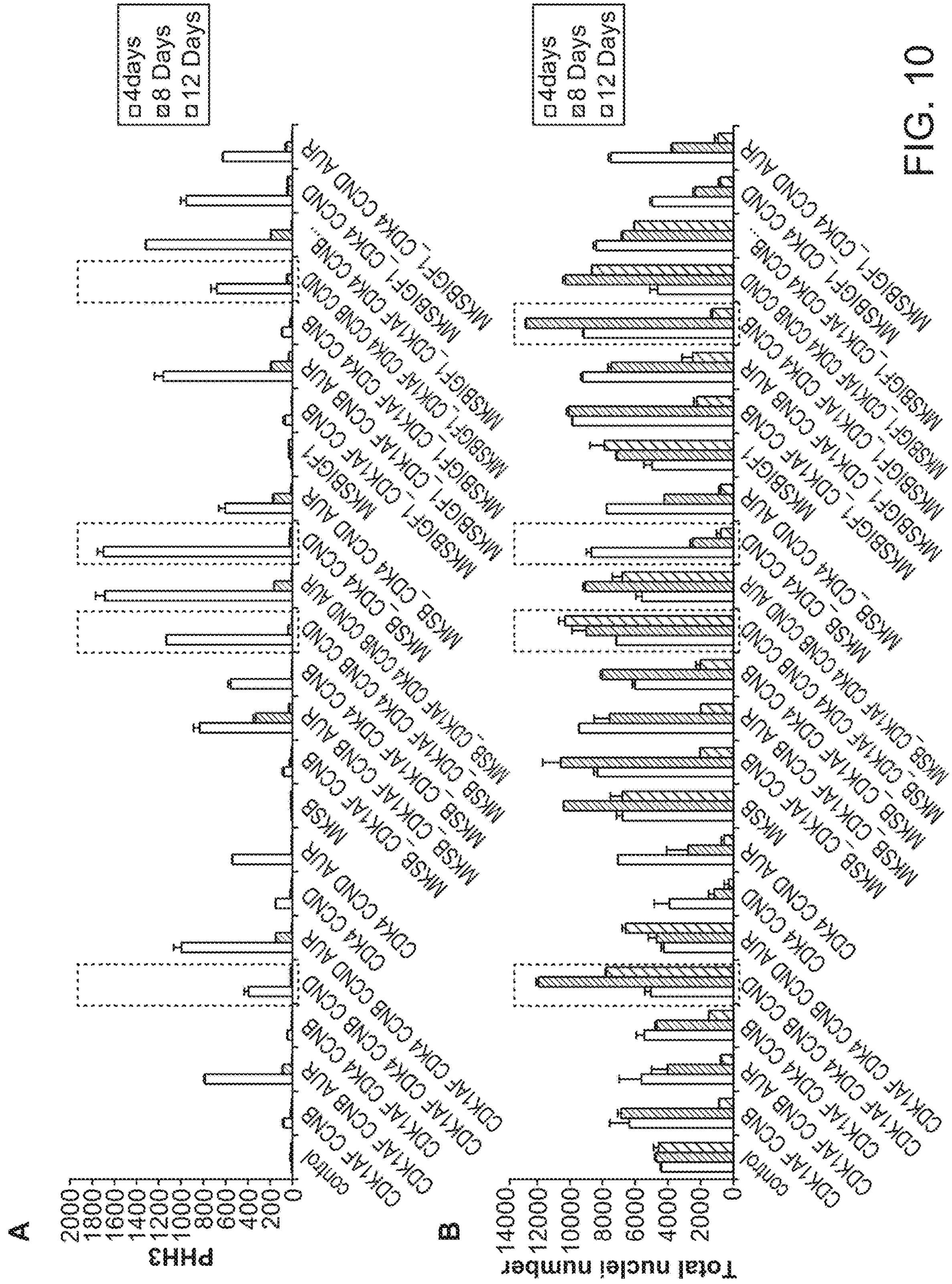
FIG. 10 shows the ability of various combinations of factors to induce cell cycle reentry of human cardiomyocytes as assessed by cell proliferation (PHH3 staining) (panel A) and survival by total nuclei counts (panel B). Cells were assessed at 4-, 8-, and 12-days following treatment.
Figure 11:
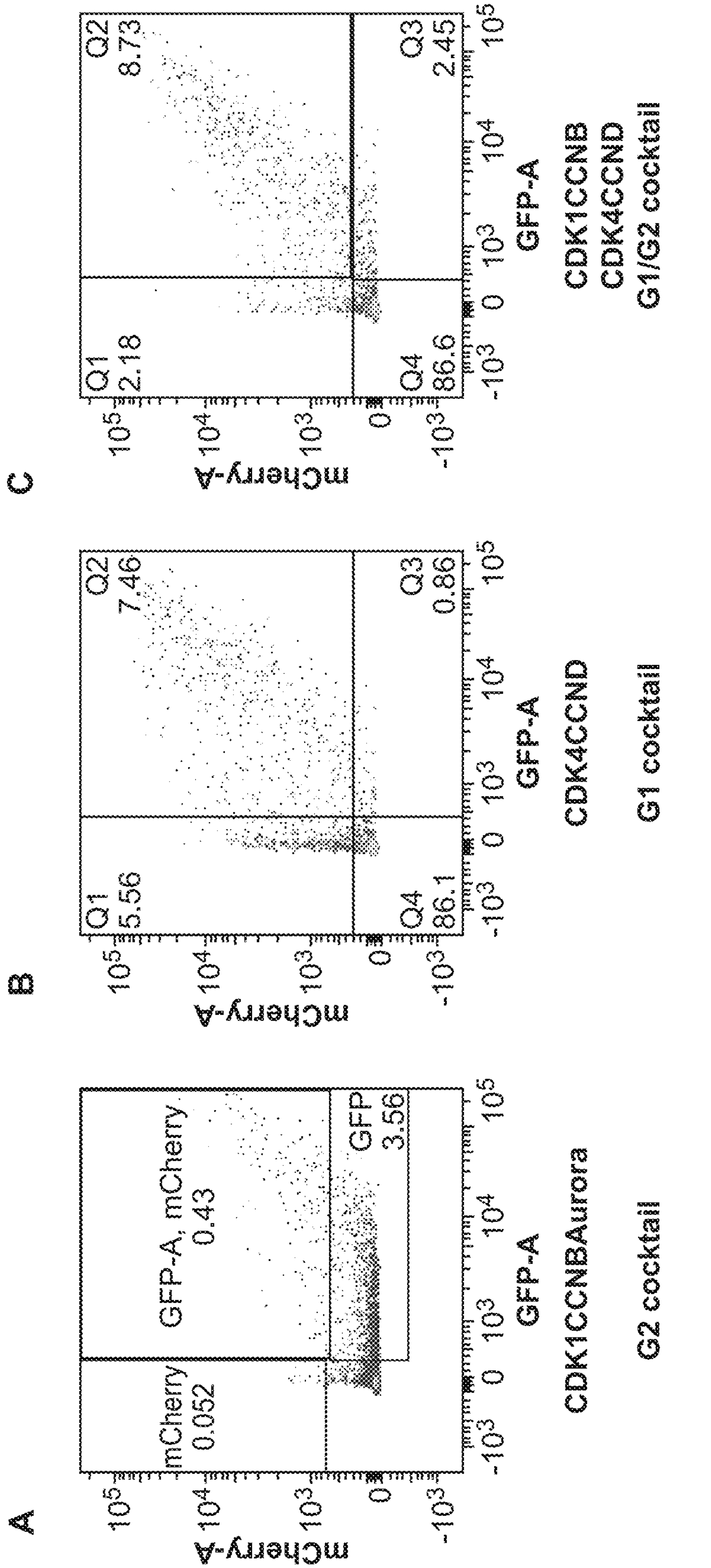
FIG. 11 demonstrates the differences in cell cycle distribution between a first cocktail of CDK1, CCNB, and Aurora (panel A), a cocktail of CDK4 and CCND (panel B), and a cocktail of CDK1, CDK4, CCNB and CCND (panel C).

To determine an optimal cocktail of factors for inducing cell proliferation and/or cell cycle reentry of human postmitotic cardiomyocytes, combinations of factors were screened. Human embryonic stem cell-derived cardiomyocytes were generated as previously described Lian, X. et al. (2013) *Nat Protoc* 8(1): 162-175. Cells were treated with combinations of CDK1AF, CDK4, CCNB1, CCND1, AURKB or GFP control adenovirus, with or without combinations of TGF-βi (SB431542, "SB"), a CDK activator (MK1775, "MK"), and IGF1. Analysis was performed to identify cocktails of factors that increased the number of cells undergoing mitosis as assessed by increased phosphohistone H3 staining at 4-, 8-, and 12-days after treatment with factor cocktails. FIG. 10, panel A. Analysis was also performed to identify which cocktails of factors had the highest cell survival as assessed by the increase in total number of nuclei. FIG. 10, panel B.

These data demonstrated that the combination of CDK1AF, CDK4, CCNB1, and CCND1 was the cocktail of factors screened that resulted in best survival and increase in proliferative postmitotic cardiomyocytes. It was also observed that inhibition of TGFβ signaling using SB431542 enhanced survival. In addition, activation of CDK1 with small molecule MK1775 could replace CDK1 and CCNB1 from the cocktail.

Example 3. Cocktails Target Different Stages of the Cell Cycle

To better understand the mechanisms of action by which the different cocktails of factors promote cell proliferation and/or cell cycle reentry of postmitotic cells, cell cycle behavior of cells was visualized using Fluorescence Ubiquitin Cell Cycle Indicator (FUCCI) technology. Zielke et al. (2015) *WIREs Dev Biol* 4:469-487. Using this system, cells in M/G1 phase fluoresce red (mCherry), cells in S/G2 fluoresce green (GFP), and cell in S fluoresce red and green. Comparison of the cocktail combination of CDK1, CCNB1, and AURKB (panel A) with the cocktails of CDK4 and CCND (panel B) and CDK1, CCNB, CDK4, and CCND (panel C) showed that the combination of CDK1, CCNB1, and AURKB acted as a G2 cocktail and enhanced the number of cells in G2, but not G1 or S. The combination of CDK4 and CCND1 acted as a G1 cocktail and enhanced the number of cells in G1 and S but not G2. On the other hand, the combination of CDK1, CCNB1, CDK4 and CCND1 induced a balanced distribution of G1/G2 cells. It is believed that the balanced distribution aids in cell survival.

Example 4. CDK1/CCNB1/CDK4/CCND1 Cocktail Improves Cardiac Function after Myocardial Infarction To determine whether the G1/G2 cocktail of CDK1/CCNB1/CDK4/CCND1 could improve cardiac function following a myocardial infarction, in vivo studies were performed. The animal protocol for surgery was approved by the University of California, San Francisco Institutional Animal Care and Use Committee. All surgeries were performed as previously described. Qian, L., et al. (2012) *Nature* 485:593-598. Briefly, mice were anaesthetized with 2.4% isoflurane/97.6% oxygen and placed in a supine position on a heating pad (37° C.). Animals were intubated with a 19 G stump needle and ventilated with room air using a MiniVent Type 845 mouse ventilator (Hugo Sachs Elektronik-Harvard Apparatus; stroke volume, 250 μl; respiratory rate, 120 breaths per minute). Myocardial infarction (MI) was induced by permanent ligation of the left anterior descending (LAD) artery with a 7-0 prolene suture as described in Qian, L., et al. (2012) *Nature* 485:593-598. Sham-operated animals served as surgical controls and were subjected to the same procedures as the experimental animals with the exception that the LAD was not ligated. AT the time of MI, the animals received an injection of the G1/G2 cocktail into the myocardium.

Serial echocardiography was conducted before MI and 1, 2, 4, 8 and 12 weeks after MI to assess the cardiac function.

Echocardiography was performed with the Vevo 770 High-Resolution Micro-Imaging System (VisualSonics) with a 15-MHz linear-array ultrasound transducer. The left ventricle was assessed in both parasternal long-axis and short-axis views at a frame rate of 120 Hz. End-systole or end-diastole were defined as the phases in which the left ventricle appeared the smallest and largest, respectively, and used for ejection-fraction measurements. To calculate the shortening fraction, left-ventricular end-systolic and end-diastolic diameters were measured from the left ventricular M-mode tracing with a sweep speed of 50 mm/s at the papillary muscle. B-mode was used for two-dimensional measurements of end-systolic and end-diastolic dimensions.

Standard Masson's Trichrome staining was performed on hearts 12 weeks post-viral delivery and coronary artery ligation. To determine scar size, ImagePro software was used to measure the scar area (blue) and healthy area (red) on transverse sections spanning four levels within the left ventricle of an MI heart.

Figure 12:
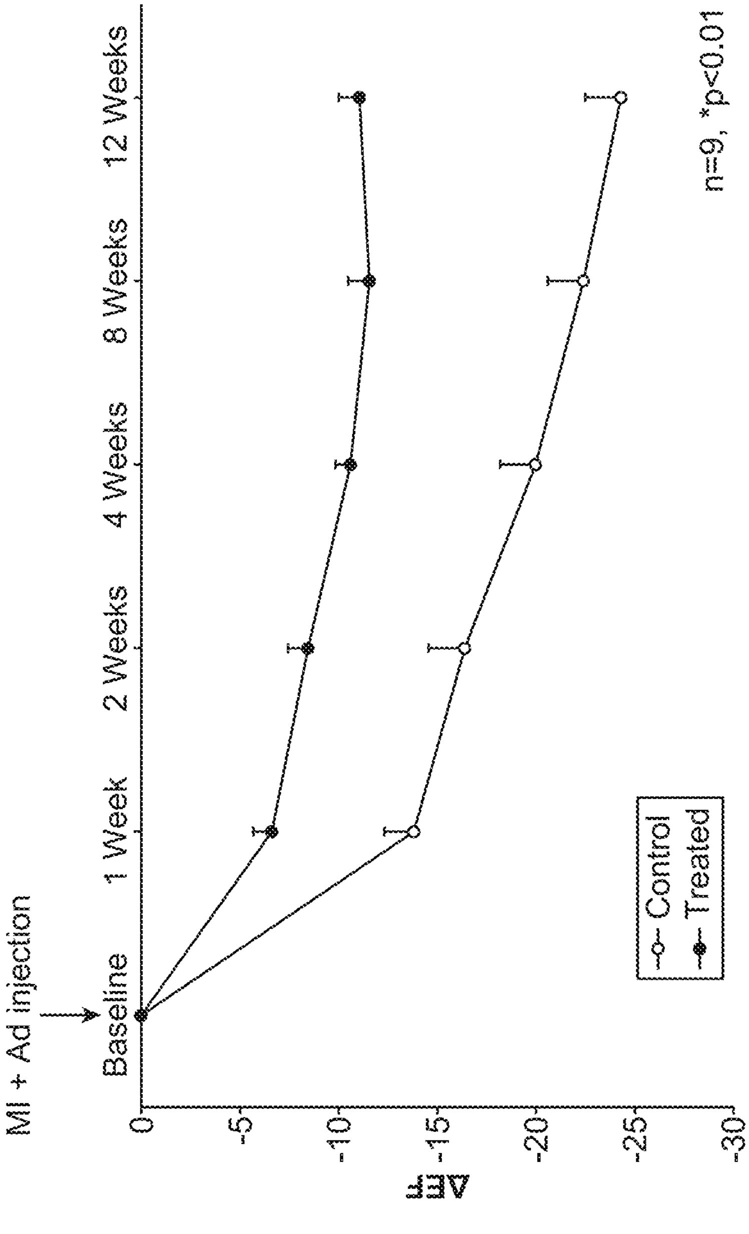
FIG. 12 shows improved cardiac function following injection of CDK1AF, CCNB, CDK4, CCND (G1/G2 cocktail) adenoviruses into the myocardium at the time of myocardial infarction as indicated by the ejection fraction (EF) measured by echocardiography.
Figure 13:
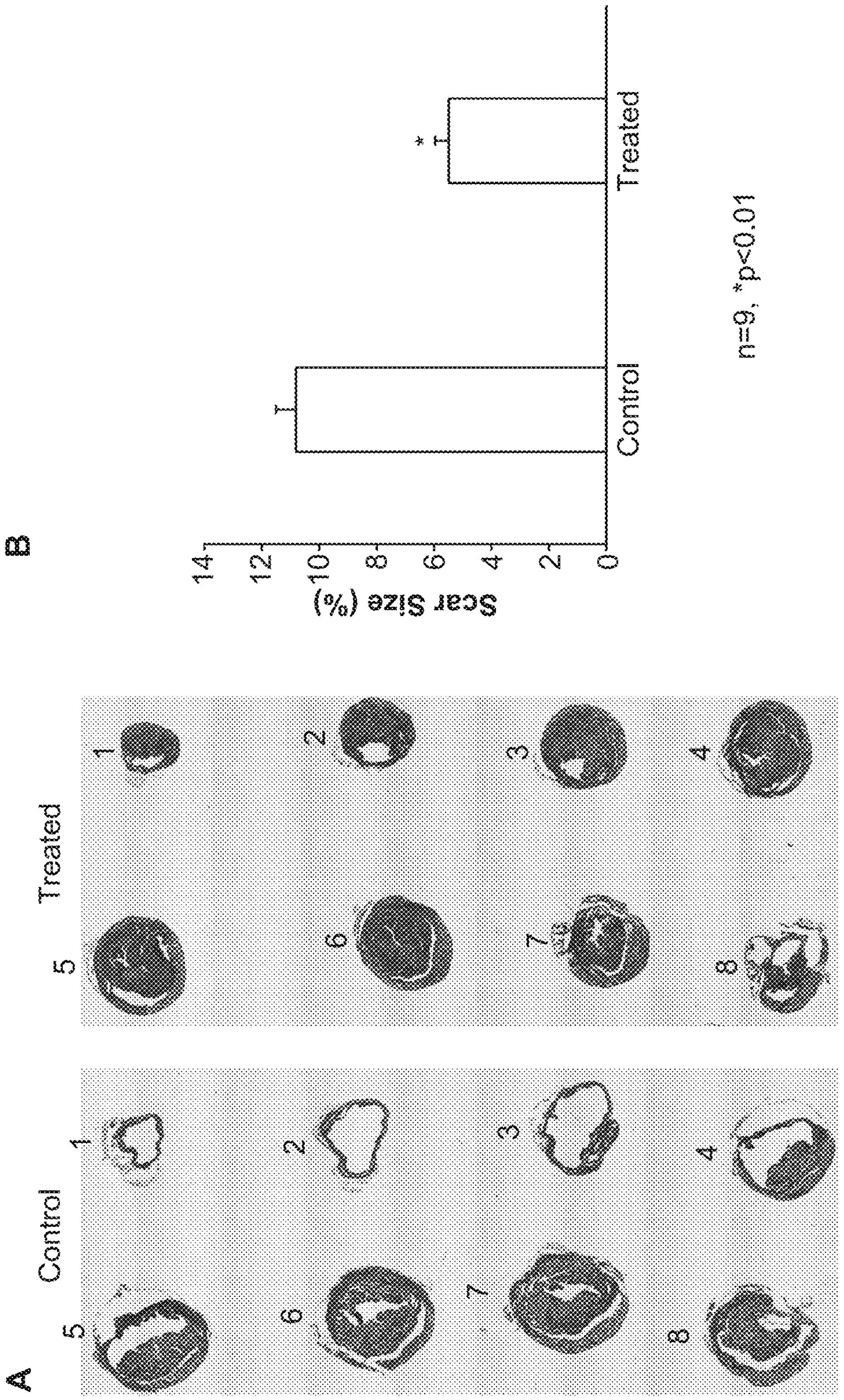
FIG. 13 depicts histological sections taken from control and treated animals showing thicker muscles (panel A) and reduced scar size (panel B) in treated animals.

Results show that treatment with the G1/G2 cocktail significantly enhanced cardiac function compared to sham treated animal, as reflected by changes in the ejection fraction (EF) assessed by echocardiography (FIG. 12). The improved function occurred as early as 1 week after MI. Histological analyses were performed to quantify the scar size and detect the presence of muscle within the infarct area of treated hearts. Consistent with the in vivo imaging observations, it was found in hearts isolated from animals treated with G1/G2 cocktail, thicker bands of myocytes were observed within the infarct zone (FIG. 13, panel A). In addition, scar size was significantly reduced in treated animals (FIG. 13, panel B).

Figure 14:
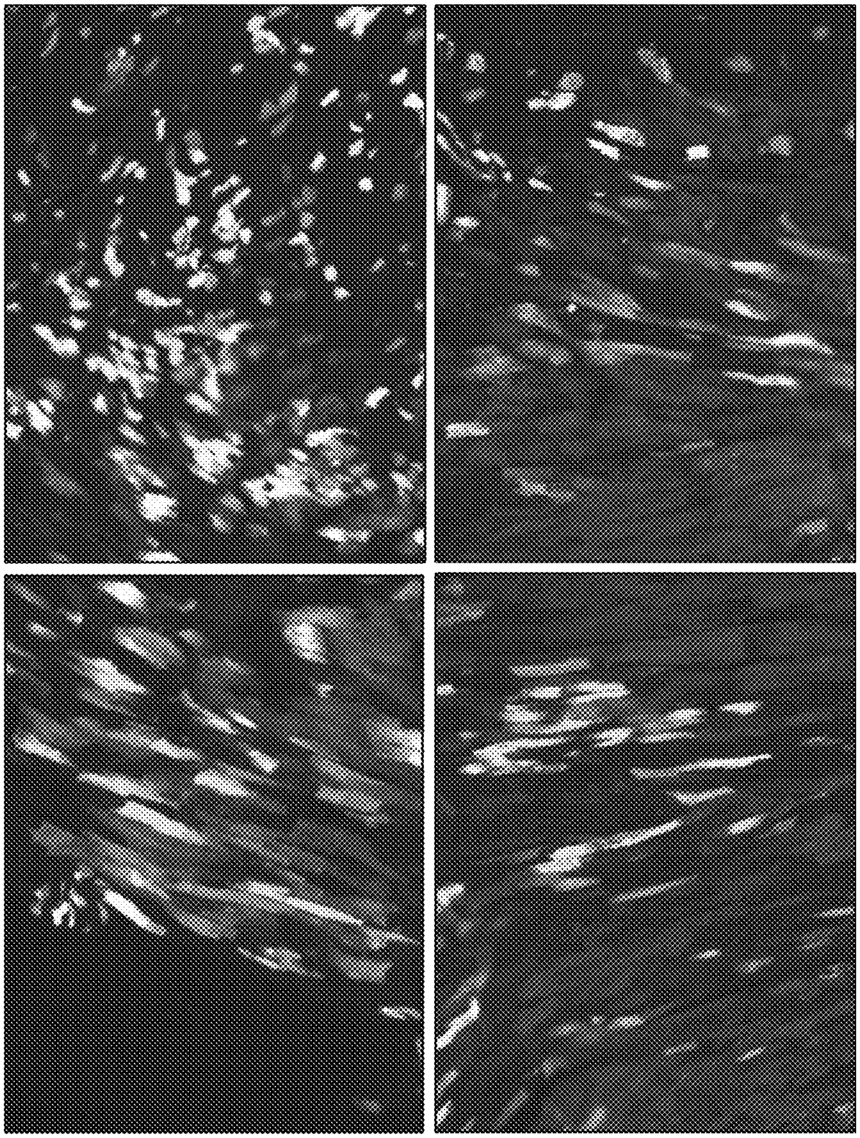
FIG. 14 demonstrates dividing cardiomyocytes treated with the CDK1AF, CCNB, CDK4, CCND cocktail using mosaic analysis of dual marker (MADM) anaylsis.

To confirm that this remuscularization was due to cardiomyocyte proliferation in vivo, Mosaic Analysis of Dual Marker (MADM) mice were used to perform lineage tracing. In cells isolated from these mice, when a cell divides it will rise to a green and a red cell and if there is no division it will stay yellow and, therefore, distinguish between dividing and non-dividing cells. It was found that the remuscularization around the infarct area was due, at least in part, to generation of new cardiomyocytes through proliferation of endogenous cells (FIG. 14).

Example 5. Induction of Proliferation in Postmitotic Neurons

Figure 15:
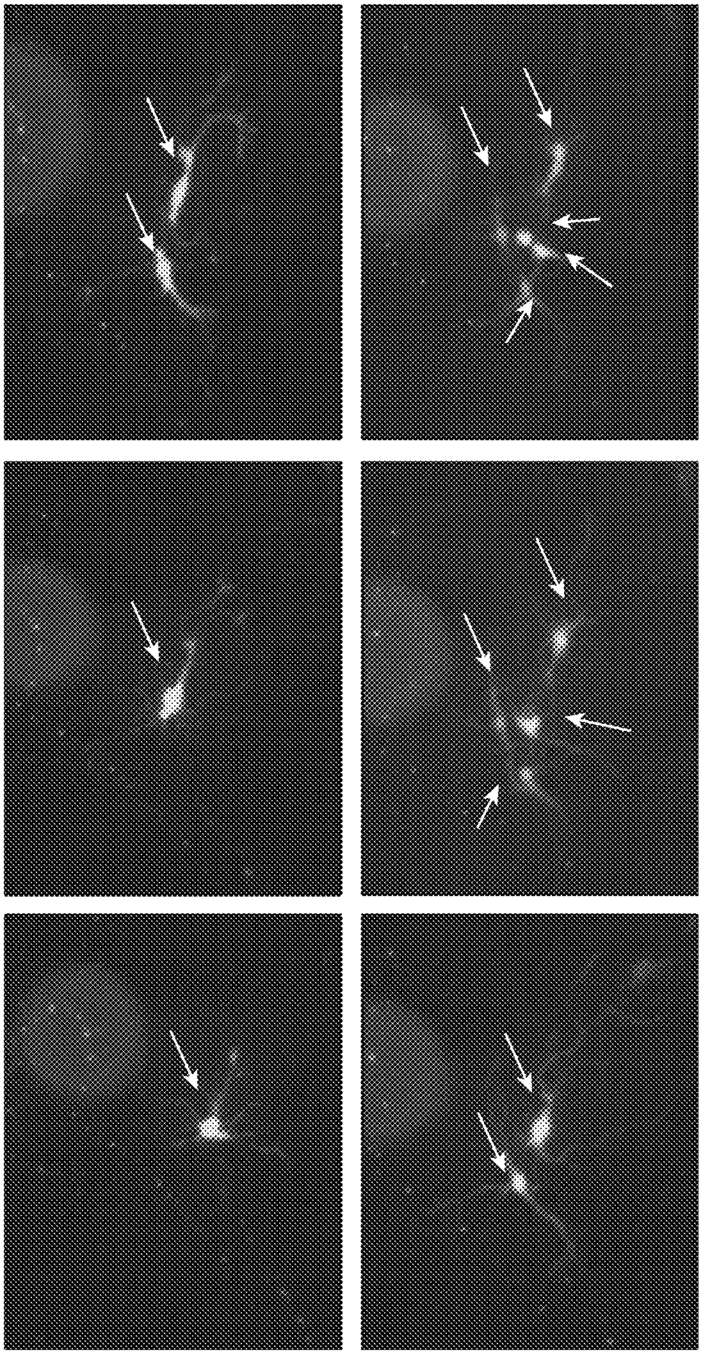
FIG. 15 show time lapse images of a neuron making three successive cell divisions within five days when treated with the CDK1AF, CCNB, CDK4, CCND cocktail.
Figure 16:
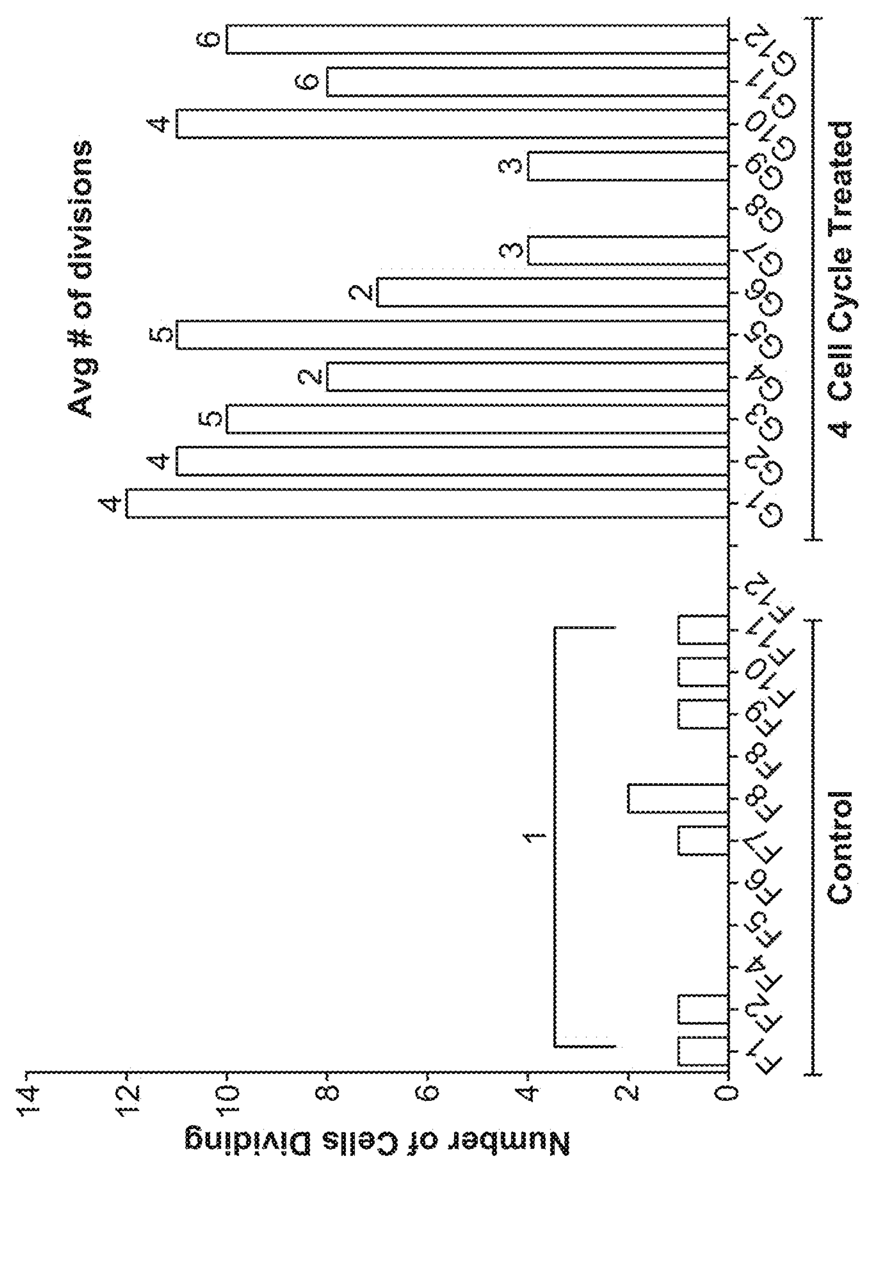
FIG. 16 demonstrates that cells treated with the CDK1AF, CCNB, CDK4, CCND cocktail undergo most divisions 60-90 hours post-infection, with some cell division occurring as late as 120 hours post-infection. The column height represents the number of cells that have undergone division and the number on the top of the column indicates the average number of divisions performed by each cell.

To determine whether the G1/G2 cocktail could also induce cell proliferation and/or cell cycle reentry of postmitotic neurons, primary cultures of cortical neurons were prepared from rat neonates (P16-18) as reported in Arrasate, M. et al. (2005) *Proc Natl Acad Sci USA* 102(10):3840-3845. Brain cortices were dissected, treated with papain and then trypsin inhibitor, and gently triturated to dissociate single neurons in Optimem_glucose medium. Cells (approximately 150,000) were plated in each well of a 96-well tissue culture plate. Two hours later, the plating medium was replaced by growth medium with serum. Cells were labeled with pGW1-GFP as a morphology marker and neuronal specific promoter MAP2-DsRed to indicate that these cells are mature neurons. Time lapse microscopy was performed to identify dividing cells. As shown in FIG. 15, the G1/G2 cocktail induced cell division of postmitotic neurons. In addition, it was determined that most divisions occurred between 60-90 hours post-infection with the G1/G2 cocktail, while some divisions occurred as late as 120 hours post-infection. FIG. 16.

Example 6. Induction of Proliferation in Postmitotic Pancreatic Beta Cells

To determine whether the G1/G2 cocktail can induce cell proliferation and/or cell cycle reentry of postmitotic pancreatic β-cells, β-cells are purified from other non-β-cell subpopulations, for example, by the methods described in Clardy et al. (2015) *Scientific Reports* 5:13681. Purified β-cells are plated into a tissue culture plate and treated with the G1/G2 adenoviral cocktail or sham adenoviral control. β-cells treated with the G1/G2 cocktail show an increase in cell divisions at 48-, 72- and 96-hours post-infection. β-cells treated with the sham cocktail show no increase in cell division.

Example 7. Induction of Proliferation in Postmitotic Hair Cells

To determine whether the G1/G2 cocktail could also induce cell proliferation and/or cell cycle reentry of postmitotic hair cells of the inner ear, inner ear cells are derived in vitro from induced pluripotent stem cells using methods similar to those described in Ronaghi M et al. (2014) *Stem Cells Dev* 23(11)1275-1284. Differentiated inner ear cells are plated into a tissue culture plate and treated with the G1/G2 adenoviral cocktail or sham adenoviral control. Cells treated with the G1/G2 cocktail show an increase in cell divisions at 48-, 72- and 96-hours post-infection. Cells treated with the sham cocktail show no increase in cell division.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

In addition, where the features or aspects of the invention are described in terms of Markush groups, those skilled in the art will recognize that the invention is also thereby described in terms of any individual member or subgroup members of the Markush group.

All publications, patent applications, patents and other references mentioned herein are expressly incorporated by reference in their entirety, to the same extent as if each were incorporated by reference individually. In case of conflict, the present specification, including definitions, will control.

```
Human CDK1
Gene ID: 983
mRNA: NM_001786 (transcript variant 1), CDS (143..1036)
                                                    SEQ. ID. NO. 1
  1    agcgcggtga gtttgaaact gctcgcactt ggcttcaaag ctggctcttg gaaattgagc

 61    ggagagcgac gcggttgttg tagctgccgc tgcggccgcc gcggaataat aagccgggat

121    ctaccatacc cattgactaa ctatggaaga ttataccaaa atagagaaaa ttggagaagg
```

-continued 181 tacctatgga gttgtgtata agggtagaca caaaactaca ggtcaagtgg tagccatgaa 241 aaaaatcaga ctagaaagtg aagaggaagg ggttcctagt actgcaattc gggaaatttc 301 tctattaaag gaacttcgtc atccaaatat agtcagtctt caggatgtgc ttatgcagga 361 ttccaggtta tatctcatct ttgagtttct ttccatggat ctgaagaaat acttggattc 421 tatccctcct ggtcagtaca tggattcttc acttgttaag agttatttat accaaatcct 481 acaggggatt gtgttttgtc actctagaag agttcttcac agagacttaa aacctcaaaa 541 tctcttgatt gatgacaaag gaacaattaa actggctgat tttggccttg ccagagcttt 601 tggaatacct atcagagtat atacacatga ggtagtaaca ctctggtaca gatctccaga 661 agtattgctg gggtcagctc gttactcaac tccagttgac atttggagta taggcaccat 721 atttgctgaa ctagcaacta agaaaccact tttccatggg gattcagaaa ttgatcaact 781 cttcaggatt ttcagagctt tgggcactcc caataatgaa gtgtggccag aagtggaatc 841 tttacaggac tataagaata catttcccaa atggaaacca ggaagcctag catcccatgt 901 caaaaacttg gatgaaaatg gcttggattt gctctcgaaa atgttaatct atgatccagc 961 caaacgaatt tctggcaaaa tggcactgaa tcatccatat tttaatgatt tggacaatca 1021 gattaagaag atgtagcttt ctgacaaaaa gtttccatat gttatatcaa cagatagttg 1081 tgtttttatt gttaactctt gtctattttt gtcttatata tatttctttg ttatcaaact 1141 tcagctgtac ttcgtcttct aatttcaaaa atataactta aaaatgtaaa tattctatat 1201 gaatttaaat ataattctgt aaatgtgtgt aggtctcact gtaacaacta tttgttacta 1261 taataaaact ataatattga tgtcaggaat caggaaaaaa tttgagttgg cttaaatcat 1321 ctcagtcctt atggcagttt tattttcctg tagttggaac tactaaaatt taggaaaatg 1381 ctaagttcaa gtttcgtaat gctttgaagt atttttatgc tctgaatgtt taaatgttct 1441 catcagtttc ttgccatgtt gttaactata caacctggct aaagatgaat atttttctac 1501 tggtatttta attttagacc taaatgttta agcattcgga atgagaaaac tatacagatt 1561 tgagaaatga tgctaaattt ataggagttt tcagtaactt aaaaagctaa catgagagca 1621 tgccaaaatt tgctaagtct tacaaagatc aagggctgtc cgcaacaggg aagaacagtt 1681 ttgaaaattt atgaactatc ttatttttag gtaggttttg aaagcttttt gtctaagtga 1741 attcttatgc cttggtcaga gtaataactg aaggagttgc ttatcttggc tttcgagtct 1801 gagtttaaaa ctacacattt tgacatagtg tttattagca gccatctaaa aaggctctaa 1861 tgtatattta actaaaatta ctagctttgg gaattaaact gtttaacaaa taaaaaaaaa 1921 aaa Human CDK1

SEQ. ID. NO. 2

MEDYTKIEKIGEGTYGVVYKGRHKTTGQVVAMKKIRLESEEEGVPSTAIREISLLK

ELRHPNIVSLQDVLMQDSRLYLIFEFLSMDLKKYLDSIPPGQYMDSSLVKSYLYQI

LQGIVFCHSRRVLHRDLKPQNLLIDDKGTIKLADFGLARAFGIPIRVYTHEVVTLW

YRSPEVLLGSARYSTPVDIWSIGTIFAELATKKPLFHGDSEIDQLFRIFRALGTPNNE

VWPEVESLQDYKNTFPKWKPGSLASHVKNLDENGLDLLSKMLIYDPAKRISGKM

ALNHPYFNDLDNQIKKM

Human Cyclin B1 (CCNB1)
GeneID: 891
mRNA: NM_031966.3, CDS (254..1555)

SEQ. ID. NO. 3

1 cgaacgcctt cgcgcgatcg ccctggaaac gcattctctg cgaccggcag ccgccaatgg 61 gaagggagtg agtgccacga acaggccaat aaggagggag cagtgcgggg tttaaatctg -continued 121 aggctaggct ggctcttctc ggcgtgctgc ggcggaacgg ctgttggttt ctgctgggtg 181 taggtccttg gctggtcggg cctccggtgt tctgcttctc cccgctgagc tgctgcctgg 241 tgaagaggaa gccatggcgc tccgagtcac caggaactcg aaaattaatg ctgaaaataa 301 ggcgaagatc aacatggcag gcgcaaagcg cgttcctacg gcccctgctg caacctccaa 361 gcccggactg aggccaagaa cagctcttgg ggacattggt aacaaagtca gtgaacaact 421 gcaggccaaa atgcctatga agaaggaagc aaaaccttca gctactggaa aagtcattga 481 taaaaaacta ccaaaacctc ttgaaaaggt acctatgctg gtgccagtgc cagtgtctga 541 gccagtgcca gagccagaac ctgagccaga acctgagcct gttaaagaag aaaaactttc 601 gcctgagcct attttggttg atactgcctc tccaagccca atggaaacat ctggatgtgc 661 ccctgcagaa gaagacctgt gtcaggcttt ctctgatgta attcttgcag taaatgatgt 721 ggatgcagaa gatggagctg atccaaacct ttgtagtgaa tatgtgaaag atatttatgc 781 ttatctgaga caacttgagg aagagcaagc agtcagacca aaatacctac tgggtcggga 841 agtcactgga aacatgagag ccatcctaat tgactggcta gtacaggttc aaatgaaatt 901 caggttgttg caggagacca tgtacatgac tgtctccatt attgatcggt tcatgcagaa 961 taattgtgtg cccaagaaga tgctgcagct ggttggtgtc actgccatgt ttattgcaag 1021 caaatatgaa gaaatgtacc ctccagaaat tggtgacttt gcttttgtga ctgacaacac 1081 ttatactaag caccaaatca gacagatgga aatgaagatt ctaagagctt taaactttgg 1141 tctgggtcgg cctctacctt tgcacttcct tcggagagca tctaagattg gagaggttga 1201 tgtcgagcaa catactttgg ccaaatacct gatggaacta actatgttgg actatgacat 1261 ggtgcacttt cctccttctc aaattgcagc aggagctttt tgcttagcac tgaaaattct 1321 ggataatggt gaatggacac caactctaca acattacctg tcatatactg aagaatctct 1381 tcttccagtt atgcagcacc tggctaagaa tgtagtcatg gtaaatcaag gacttacaaa 1441 gcacatgact gtcaagaaca agtatgccac atcgaagcat gctaagatca gcactctacc 1501 acagctgaat tctgcactag ttcaagattt agccaaggct gtggcaaagg tgtaacttgt 1561 aaacttgagt tggagtacta tatttacaaa taaaattggc accatgtgcc atctgtacat 1621 attactgttg catttacttt taataaagct tgtggcccct tttacttttt tatagcttaa 1681 ctaatttgaa tgtggttact tcctactgta gggtagcgga aaagttgtct taaaaggtat 1741 ggtggggata tttttaaaaa ctccttttgg tttacctggg gatccaattg atgtatatgt 1801 ttatatactg ggttcttgtt ttatatacct ggcttttact ttattaatat gagttactga 1861 aggtgatgga ggtatttgaa aattttactt ccataggaca tactgcatgt aagccaagtc 1921 atggagaatc tgctgcatag ctctatttta aagtaaaagt ctaccaccga atccctagtc 1981 cccctgtttt ctgtttcttc ttgtgattgc tgccataatt ctaagttatt tacttttacc 2041 actatttaag ttatcaactt tagctagtat cttcaaactt tcactttgaa aaatgagaat 2101 tttatattct aagccagttt tcattttggt tttgtgtttt ggttaataaa acaatactca 2161 aatacaaaaa aaaaaaa Human Cyclin B1 (CCNB1)

SEQ. ID. NO. 4

MALRVTRNSKINAENKAKINMAGAKRVPTAPAATSKPGLRPRTALGDIGNKVSE

QLQAKMPMKKEAKPSATGKVIDKKLPKPLEKVPMLVPVPVSEPVPEPEPEPEPEP

VKEEKLSPEPILVDTASPSPMETSGCAPAEEDLCQAFSDVILAVNDVDAEDGADPN

LCSEYVKDIYAYLRQLEEEQAVRPKYLLGREVTGNMRAILIDWLVQVQMKFRLL

QETMYMTVSIIDRFMQNNCVPKKMLQLVGVTAMFIASKYEEMYPPEIGDFAFVT

-continued

DNTYTKHQIRQMEMKILRALNFGLGRPLPLHFLRRASKIGEVDVEQHTLAKYLME

LTMLDYDMVHFPPSQIAAGAFCLALKILDNGEWTPTLQHYLSYTEESLLPVMQHL

AKNVVMVNQGLTKHMTVKNKYATSKHAKISTLPQLNSALVQDLAKAVAKV

Human Aurora kinase B (AURKB)
GeneID:9212
mRNA: NM_004217.3 (transcript variant 1), CDS (123..1157)

SEQ. ID. NO. 5

```
   1  cggggcggga gatttgaaaa gtccttggcc agggcgcggc gtggcagatt cagttgtttg
  61  cgggcggccg ggagagtagc agtgccttgg accccagctc tcctccccct ttctctctaa
 121  ggatggccca gaaggagaac tcctacccct ggccctacgg ccgacagacg gctccatctg
 181  gcctgagcac cctgccccag cgagtcctcc ggaaagagcc tgtcacccca tctgcacttg
 241  tcctcatgag ccgctccaat gtccagccca cagctgcccc tggccagaag gtgatggaga
 301  atagcagtgg gacacccgac atcttaacgc ggcacttcac aattgatgac tttgagattg
 361  ggcgtcctct gggcaaaggc aagtttggaa acgtgtactt ggctcgggag aagaaaagcc
 421  atttcatcgt ggcgctcaag gtcctcttca agtcccagat agagaaggag ggcgtggagc
 481  atcagctgcg cagagagatc gaaatccagg cccacctgca ccatcccaac atcctgcgtc
 541  tctacaacta tttttatgac cggaggagga tctacttgat tctagagtat gcccccccgcg
 601  gggagctcta caaggagctg cagaagagct gcacatttga cgagcagcga acagccacga
 661  tcatggagga gttggcagat gctctaatgt actgccatgg gaagaaggtg attcacagag
 721  acataaagcc agaaaatctg ctcttagggc tcaagggaga gctgaagatt gctgacttcg
 781  gctggtctgt gcatgcgccc tccctgagga ggaagacaat gtgtggcacc ctggactacc
 841  tgcccccaga gatgattgag gggcgcatgc acaatgagaa ggtggatctg tggtgcattg
 901  gagtgctttg ctatgagctg ctggtgggga acccaccctt tgagagtgca tcacacaacg
 961  agacctatcg ccgcatcgtc aaggtggacc taaagttccc cgcttccgtg cccatgggag
1021  cccaggacct catctccaaa ctgctcaggc ataacccctc ggaacggctg cccctggccc
1081  aggtctcagc ccacccttgg gtccgggcca actctcggag ggtgctgcct ccctctgccc
1141  ttcaatctgt cgcctgatgg tccctgtcat tcactcgggt gcgtgtgttt gtatgtctgt
1201  gtatgtatag gggaaagaag ggatccctaa ctgttccctt atctgttttc tacctcctcc
1261  tttgtttaat aaaggctgaa gctttttgta ctcatgaaaa aaaaaaaaaa aaaa
```

Human Aurora kinase B (AURKB)

SEQ. ID. NO. 6

MAQKENSYPWPYGRQTAPSGLSTLPQRVLRKEPVTPSALVLMSRSNVQPTAAPG

QKVMENSSGTPDILTRHFTIDDFEIGRPLGKGKFGNVYLAREKKSHFIVALKVLFK

SQIEKEGVEHQLRREIEIQAHLHHPNILRLYNYFYDRRRIYLILEYAPRGELYKELQ

KSCTFDEQRTATIMEELADALMYCHGKKVIHRDIKPENLLLGLKGELKIADFGWS

VHAPSLRRKTMCGTLDYLPPEMIEGRMHNEKVDLWCIGVLCYELLVGNPPPFESAS

HNETYRRIVKVDLKFPASVPMGAQDLISKLLRHNPSERLPLAQVSAHPWVRANSR

RVLPPSALQSVA

Mouse CDK1
GeneID: 12534
mRNA: NM_007659.3, CDS (104..997)

SEQ. ID. NO. 7

```
   1  actcggcctc taagctcctg gagttgctgc gtccgcgcag tccggaactg cggtgtggcc
  61  ccagccggga cagagagggt ccgtcgtaac ctgttgagta actatggaag actatatcaa
 121  aatagagaaa attggagaag gtacttacgg tgtggtgtat aagggtagac acagagtcac
 181  tggccagata gtggccatga agaagatcag acttgaaagc gaggaagaag gagtgcccag
```

-continued

```
241   tactgcaatt cgggaaatct ctctattaaa agaacttcga catccaaata tagtcagcct
301   gcaggatgtg ctcatgcagg actccaggct gtatctcatc tttgagttcc tgtccatgga
361   cctcaagaag tacctggact ccatccctcc tgggcagttc atggattctt cactcgttaa
421   gagttactta caccaaatcc tccagggaat tgtgttttgc cactcccggc gagttcttca
481   cagagacttg aaacctcaaa atctattgat tgatgacaaa ggaacaatca aactggctga
541   tttcggcctt gccagagcgt ttggaatacc gatacgagtg tacacacacg aggtagtgac
601   gctgtggtac cgatctccag aagtgttgct gggctcggct cgttactcca ctccggttga
661   catctggagt atagggacca tatttgcaga actggccacc aagaagccgc ttttccacgg
721   cgactcagag attgaccagc tcttcaggat cttcagagct ctgggcactc ctaacaacga
781   agtgtggcca gaagtcgagt ccctgcagga ctacaagaac acctttccca agtggaagcc
841   ggggagcctc gcatcccacg tcaagaacct ggacgagaac ggcttggatt tgctctcaaa
901   aatgctagtc tatgatcctg ccaaacgaat ctctggcaaa atggccctga agcacccgta
961   ctttgatgac ttggacaatc agattaagaa gatgtagccc tctggatgga tgtccctgtc
1021  tgctggtcgt aggggaagat cgtgttgttt accgttggct ctcttcctgt cttgtatagt
1081  tttctttgtt tgtaaactgt catctggact tttcttaatt tcctacgtat aacttaatta
1141  acatgtaaat attattccat atgaatttaa atataattct gtatatgtgc agatgtcact
1201  gtggtggctg ttaattacta taacacaagt gttaattact acaacataag acttgagtct
1261  ccctagactt cccagcagcc attcctgcag ctcggagcac agttgaagga gctgagctca
1321  ggcctcgtga tgctttcaag tgcctccgtg ttctggatat atatgattcc tggtcagttt
1381  cttgccattt ggaaactaca acccacctac ggacagtgtt tttctacttg tgcttaagca
1441  gttgggatga gaaggccaaa gacccgagga tgtctagagt aatgaccccc agatggaagt
1501  gcaccaaagc tggctgggtt tcacagctag agatcagggg ctgtccagag caggacagct
1561  tagaacattt atgaagactc cctatttttt ggtttgttgt aaagctgttg tctagttgga
1621  ttcctgtgct ctgcatggtc agaggtaggt tagaggattt gccttggctt ctaaatccaa
1681  tttgaaaact gcttaaaatc tcctgtcctc tcttagcagt gtctaaaaat gtccttgtcc
1741  aaatatttag ctgagattcc tcactttgga aaaggagccg tatcgctgtg ctgcttagtg
1801  taattcttag aagcagcctg acttatctgc tagcagtcaa agggatgcct gagacgactg
1861  ctcctcttag aactaaaggc tgggatgctt aagtttgtct actgtttgga ggatctcggt
1921  aagactgagc ccctgttcct gtggccacct cagtttacca gtacctcagc ctcagcctcc
1981  tgcatttgct ggagtcaggg aaggtcccca gccctgagcc ctgacgctcc tgattgtaga
2041  gactgtcagt tggaggtaaa acgttcattg aagtagtcag cagccacatg catttagggc
2101  actccagtgt cagagaccat cctggaggtt tctaaccctg ccgctggcag tctactccca
2161  agacagatca gttagagtgg tcagcaaaca ccaactgctg cagaaacctg tgttggtgtg
2221  gttccctgct gctgctggga actgggccca agactagaga gcttggggct gcggttgatc
2281  atgggttctg ttcctgcatt acaccttgaa atccaagcct tctaatatct ccccttcggat
2341  cataagttgt gaatttggtc ctccgccccc gccaggtttt ctatacttgg gtttgtcttg
2401  ctgacatttt caagagtcct gactaagacg gtgattagtg tgacatgact tgagaactac
2461  cgatttgaag cacacttgaa gttaacaaat tctctcatga ttatactttt aactattatt
2521  aagattgctt gagctcaccc agatctctgt tgggaagtaa ctgggtaaca aaagccgttg
2581  cactggtttg acagctaaca actgttggta ctttgtattc agaaggaatg aggtagcgat
2641  tgaatggctg ggtgttgttt tccacagttt atacactaaa aatttgggta gccaggaggt
```

-continued 2701 agtggcgcgc aatctttaat ctcagcagag gcagtcctat ctcttgagtt ggaggccagc 2761 ctgcctgagt tccagaccag ccagggctac aggaagaagt cttaaaaaaa tattttttcc 2821 ctgtggatgt aaacccatga gaatgactgc tgtatctatc Mouse CDK1
Amino Acid Sequence

SEQ. ID. NO. 8

MEDYIKIEKIGEGTYGVVYKGRHRVTGQIVAMKKIRLESEEEGVPSTAIREISLLKE

LRHPNIVSLQDVLMQDSRLYLIFEFLSMDLKKYLDSIPPGQFMDSSLVKSYLHQIL

QGIVFCHSRRVLHRDLKPQNLLIDDKGTIKLADFGLARAFGIPIRVYTHEVVTLWY

RSPEVLLGSARYSTPVDIWSIGTIFAELATKKPLFHGDSEIDQLFRIFRALGTPNNEV

WPEVESLQDYKNTFPKWKPGSLASHVKNLDENGLDLLSKMLVYDPAKRISGKM

ALKHPYFDDLDNQIKKM

Mouse Cyclin B1 (CCNB1)
GeneID: 268697
mRNA: NM_172301.3, CDS (85..1377)

SEQ. ID. NO. 9

1 ggaacggctg ttagtgttta gctgtggata gccagaggtt agggtgtctt ctcgaatcgg 61 ggaacctctg attttggagg agccatggcg ctcagggtca ctaggaacac gaaaattaac 121 gcagaaaata aggccaaggt cagtatggca ggcgccaagc gtgtgcctgt gacagttact 181 gctgcttcca agcccgggct gagaccgaga actgctcttg gagacattgg taataaagtc 241 agcgaagagc tacaggcaag agtgcctctg aaaagggaag caaaaacgct aggtactgga 301 aaaggtactg ttaaagccct accaaaacct gtagagaagg tgcctgtgtg tgaaccagag 361 gtggaacttg ctgagcctga gcctgaacct gaacttgaac atgttagaga agagaagctt 421 tctcctgaac ctattttggt tgataatccc tctccaagcc cgatggaaac atctggatgt 481 gcgcctgcag aagagtatct gtgtcaggct ttctctgatg taatccttgc agtgagtgac 541 gtagacgcag atgatggggc tgacccaaac ctctgtagtg aatatgtgaa agatatctat 601 gcttatctcc gacaactgga ggaagagcag tcagttagac caaaatacct acagggtcgt 661 gaagtgactg gaaacatgag agctatcctc attgactggc taatacaggt tcagatgaaa 721 tttaggctgc ttcaggagac catgtacatg actgtgtcca ttattgatcg gttcatgcag 781 aacagttgtg tgcccaagaa gatgctacag ctggtcggtg taacggccat gtttattgca 841 agcaaatatg aggagatgta ccctccagaa ataggtgact tcgcctttgt gactaacaac 901 acgtacacta agcaccagat cagacagatg gagatgaaga ttctcagagt tctgaacttc 961 agcctgggtc gccctctgcc tctgcacttc ctccgtagag catctaaagt cggagaggtt 1021 gacgtcgagc agcacacttt ggccaaatac ctcatggagc tctccatgct ggactacgac 1081 atggtgcatt ttgctccttc tcaaattgca gctggggctt tctgcttagc gctgaaaatt 1141 cttgacaacg gtgaatggac accaactctg cagcactacc tatcctacag tgaagactcc 1201 ctgcttcctg ttatgcagca cctggctaag aatgtagtca tggtgaactg tggcctcaca 1261 aagcacatga ctgtcaagaa caagtatgca gcatctaagc atgctaagat cagcacgctg 1321 gcacagctga actgtacact agttcagaat ttgtctaagg ccgtgacaaa ggcataactc 1381 caatagactg ctacatctgc agatgcagtt ggcaccatgt gccgcctgta cataggatac 1441 ctaccgtgtt tacttgctct tcaataaagg ttgtgacttc tcattttaca tagcttaact 1501 catttgaatg ttgttgcttc tgagtttagg ctaacggaag ttgtcgaatt taggagtata 1561 ttaaaaactg catctagttt taacagtgga tccaactaat gtatatatct gtagcctata 1621 tgtctatata catccttcac tgtgtgtcct tatatcatca tgtcttctgc ctcactctag -continued 1681 tttaaactct aaatctacca gctagtcctt tgttccattt tccagtggtt gccaccttta 1741 accactgtct cttggtttgt caactttcag atctgaaacc aagtatcttt tittatgtaa 1801 ttatttattt gttcttaatt ggaaaatagg atgttcaaaa ttaaaggtgt gattaaaaa 1861 gaatttgccc ccaagtctca ctatcaacag ataagggtgt attcttgtat atcctgtata 1921 gatataatca tgcatatact cccaaggaga tatttttata tgggttcatt ttatcaacag 1981 tattcctatc agcattcctt tcaatgccta tattgcattt cctagtgtga acaaactgtg 2041 tgtaacatag tcattccctc ggtgggattc aagtgcattc tctcagtgcc ctccacagtg 2101 ttcttaaatg atgtttaatg tcttgcttgg cttcattcat agtagctctt ccaggggtgt 2161 gctttgaatt ctgacagcca gatgggtgtg gctgccacca taccaaggcg ccactcctgt 2221 cttgtaatgc cacctggaaa agaatcctgt ctcatttgct gttttaattt atacatctga 2281 tatcaagttg aataaaattt attggtggaa agcttt Mouse Cyclin B1 (CCNB1)
Amino Acid Sequence

SEQ. ID. NO. 10

MALRVTRNTKINAENKAKVSMAGAKRVPVTVTAASKPGLRPRTALGDIGNKVSE

ELQARVPLKREAKTLGTGKGTVKALPKPVEKVPVCEPEVELAEPEPEPELEHVRE

EKLSPEPILVDNPSPSPMETSGCAPAEEYLCQAFSDVILAVSDVDADDGADPNLCS

EYVKDIYAYLRQLEEEQSVRPKYLQGREVTGNMRAILIDWLIQVQMKFRLLQET

MYMTVSIIDRFMQNSCVPKKMLQLVGVTAMFIASKYEEMYPPEIGDFAFVTNNTY

TKHQIRQMEMKILRVLNFSLGRPLPLHFLRRASKVGEVDVEQHTLAKYLMELSML

DYDMVHFAPSQIAAGAFCLALKILDNGEWTPTLQHYLSYSEDSLLPVMQHLAKN

VVMVNCGLTKHMTVKNKYAASKHAKISTLAQLNCTLVQNLSKAVTKA

Mouse Aurora kinase B (AURKB)
GeneID:20877
mRNA: NM_011496.1, CDS (319..1356)

SEQ. ID. NO. 11

1 ggagattcga aagcgtccgg gtcgcggggt aaaccggttc tccgtgtgcg agcgcctagt 61 ggcgtaggct gcggctttgc ggggaactgc gggggctgca gtggtccacg gggctgatcg 121 ggttccgttg ggcggatcca cgtgcccgct atccgcctgg aaggagaggt gcaggagtac 181 ccccgacctt ggctgcgtgc tgactcgctt ccttctgccc gcccaggctt gcactccccg 241 gggatctgcc tctgcatctc ttgccttcgc tgttgtttcc ctctctgtcc agctcccctc 301 ccgctctcgc cctggagaat ggctcagaag gagaacgcct acccgtggcc ctacggctca 361 aagacgtctc agtctggcct gaacacgttg tcccagagag tcctacggaa ggagcccgcc 421 acgacatctg cgcttgctct cgtgaaccgg ttcaacagcc agtccacagc tgcccctggc 481 cagaagttgg ctgagaacaa gagtcagggc tccactgcct cgcaaggatc ccagaacaag 541 cagcctttca ctattgacaa ctttgagatt gggcgtcctt tgggcaaagg caaatttgga 601 aacgtgtact tggctcggga gaagaagagc cgtttcatcg tggcactcaa gatcctcttc 661 aagtctcaga ttgagaagga gggggtagag caccagcttc gccgagagat cgaaatccag 721 gcgcacctga aacatcccaa catccttcaa ctctacaact acttctacga ccagcagagg 781 atctacttaa tcctggaata cgcccctcgc ggggaactct acaaggaact gcagaagagt 841 cggaccttcg atgagcagcg gactgccacg atcatggagg aactgtcaga tgccctgacc 901 tactgccaca agaagaaggt aattcacaga gacataaagc cggagaacct gctgttaggt 961 ctgcagggag aactgaagat tgcagacttt ggctggtcgg tgcatgcccc atccctgagg 1021 aggaagacca tgtgcggcac gctggactat ctgcccccag agatgattga ggggcgcatg -continued 1081 cataatgaaa tggtagatct atggtgcatc ggggtgctct gctatgaact gatggtgggg 1141 aacccaccct tcgagagccc tagccacagt gagacgtatc gtcggattgt caaggtggac 1201 ctgaagttcc cctcttctgt gccttcgggc gcccaggacc tcatctccaa gctgctcaaa 1261 cataacccct ggcaacggct gcccctggcg gaggttgcag ctcacccttg ggtccgggcc 1321 aactcaagga gggttctgcc tccctctgcc ctttagcctg ctccttggtt ttttgtccct 1381 gtcatttttc agtgttcttt gtatgtctgt gtatgtgttc tgagaagggg tgggaactgg 1441 aaactattcc tagctccagt tctaggggat ctgatctctc ttctgacctc tacaggcaaa 1501 attaggcacc cctgtggtgc acatatatgc acaccaaaca catgaagtta caaacaaaca 1561 acaaacacac agatagtgct ggagagatgg ctcggtagtt aaaagcactg gctgctcttc 1621 ccaggaacct agaactcaat tctagcacta catggtgctc acgaccactg tctgtaacac 1681 ccagtcctgg ggaatctggg gccttcgagc ctctgcagac actaggcatg gatgtggtat 1741 acatgtatgc aggcaaaaca cccatgcact gacttttaag aaaccctcta gtctgattcc 1801 tttcaatttg tcaaatgttg aatgttattt ttaaaatatt ataagccatt taatacaatt 1861 tttctttgaa acatggtata gcctagtctg tcttaaattc agaaaaatta tgaagaacaa 1921 cattttataa taaagtctta aatgtttcat gtttttg Mouse Aurora kinase B (AURKB)
Amino Acid Sequence

SEQ. ID. NO. 12

MAQKENAYPWPYGSKTSQSGLNTLSQRVLRKEPATTSALALVNRFNSQSTAAPG

QKLAENKSQGSTASQGSQNKQPFTIDNFEIGRPLGKGKFGNVYLAREKKSRFIVAL

KILFKSQIEKEGVEHQLRREIEIQAHLKHPNILQLYNYFYDQQRIYLILEYAPRGEL

YKELQKSRTFDEQRTATIMEELSDALTYCHKKKVIHRDIKPENLLLGLQGELKIAD

FGWSVHAPSLRRKTMCGTLDYLPPEMIEGRMHNEMVDLWCIGVLCYELMVGNP

PFESPSHSETYRRIVKVDLKFPSSVPSGAQDLISKLLKHNPWQRLPLAEVAAHPWV

RANSRRVLPPSAL

Human CDK4
mRNA: KR709911

SEQ. ID. NO. 13

1 gttcgttgca acaaattgat gagcaatgct tttttataat gccaactttg tacaaaaaag 61 ttggcatggc tacctctcga tatgagccag tggctgaaat tggtgtcggt gcctatggga 121 cagtgtacaa ggcctgtgat ccccacagtg gccactttgt ggccctcaag agtgtgagag 181 tccccaatgg aggaggaggt ggaggaggcc ttcccatcag cacagttcgt gaggtggctt 241 tactgaggcg actggaggct tttgagcatc ccaatgttgt ccggctgatg gacgtctgtg 301 ccacatcccg aactgaccgg gagatcaagg taaccctggt gtttgagcat gtagaccagg 361 acctaaggac atatctggac aaggcacccc caccaggctt gccagccgaa acgatcaagg 421 atctgatgcg ccagtttcta agaggcctag atttccttca tgccaattgc atcgttcacc 481 gagatctgaa gccagagaac attctggtga caagtggtgg aacagtcaag ctggctgact 541 ttggcctggc cagaatctac agctaccaga tggcacttac acccgtggtt gttacactct 601 ggtaccgagc tcccgaagtt cttctgcagt ccacatatgc aacacctgtg gacatgtgga 661 gtgttggctg tatctttgca gagatgtttc gtcgaaagcc tctcttctgt ggaaactctg 721 aagccgacca gttgggcaaa atctttgacc tgattgggct gcctccagag gatgactggc 781 ctcgagatgt atccctgccc cgtggagcct ttcccccag agggccccgc ccagtgcagt 841 cggtggtacc tgagatggag gagtcgggag cacagctgct gctggaaatg ctgactttta 901 acccacacaa gcgaatctct gcctttcgag ctctgcagca ctcttatcta cataaggatg -continued 961 aaggtaatcc ggagtgccca actttcttgt acaaagttgg cattataaga aagcattgct 1021 tatcaatttg ttgcaacgaa c Human CDK4
Amino Acid Sequence

SEQ. ID. NO. 14

MATSRYEPVAEIGVGAYGTVYKARDPHSGHFVALKSVRVPNGGGGGGGLPISTV

REVALLRRLEAFEHPNVVRLMDVCATSRTDREIKVTLVFEHVDQDLRTYLDKAPP

PGLPAETIKDLMRQFLRGLDFLHANCIVHRDLKPENILVTSGGTVKLADFGLARIY

SYQMALTPVVVTLWYRAPEVLLQSTYATPVDMWSVGCIFAEMFRRKPLFCGNSE

ADQLGKIFDLIGLPPEDDWPRDVSLPRGAFPPRGPRPVQSVVPEMEESGAQLLLEM

LTFNPHKRISAFRALQHSYLHKDEGNPE

Human CCND1
mRNA: NM_053056

SEQ. ID. NO. 15

1 cacacggact acaggggagt tttgttgaag ttgcaaagtc ctggagcctc cagagggctg 61 tcggcgcagt agcagcgagc agcagagtcc gcacgctccg gcgaggggca gaagagcgcg 121 agggagcgcg gggcagcaga agcgagagcc gagcgcggac ccagccagga cccacagccc 181 tccccagctg cccaggaaga gccccagcca tggaacacca gctcctgtgc tgcgaagtgg 241 aaaccatccg ccgcgcgtac cccgatgcca acctcctcaa cgaccgggtg ctgcgggcca 301 tgctgaaggc ggaggagacc tgcgcgccct cggtgtccta cttcaaatgt gtgcagaagg 361 aggtcctgcc gtccatgcgg aagatcgtcg ccacctggat gctggaggtc tgcgaggaac 421 agaagtgcga ggaggaggtc ttcccgctgg ccatgaacta cctggaccgc ttcctgtcgc 481 tggagcccgt gaaaaagagc cgcctgcagc tgctgggggc cacttgcatg ttcgtggcct 541 ctaagatgaa ggagaccatc cccctgacgg ccgagaagct gtgcatctac accgacaact 601 ccatccggcc cgaggagctg ctgcaaatgg agctgctcct ggtgaacaag ctcaagtgga 661 acctggccgc aatgaccccg cacgatttca ttgaacactt cctctccaaa atgccagagg 721 cggaggagaa caaacagatc atccgcaaac acgcgcagac cttcgttgcc ctctgtgcca 781 cagatgtgaa gttcatttcc aatccgccct ccatggtggc agcggggagc gtggtggccg 841 cagtgcaagg cctgaacctg aggagcccca acaacttcct gtcctactac cgcctcacac 901 gcttcctctc cagagtgatc aagtgtgacc cggactgcct ccgggcctgc caggagcaga 961 tcgaagccct gctggagtca agcctgcgcc aggcccagca gaacatggac cccaaggccg 1021 ccgaggagga ggaagaggag gaggaggagg tggacctggc ttgcacaccc accgacgtgc 1081 gggacgtgga catctgaggg cgccaggcag gcgggcgcca ccgccacccg cagcgagggc 1141 ggagccggcc ccaggtgctc ccctgacagt ccctcctctc cggagcattt tgataccaga 1201 agggaaagct tcattctcct tgttgttggt tgttttttcc tttgctcttt ccccccttcca 1261 tctctgactt aagcaaaaga aaaagattac ccaaaaactg tctttaaaag agagagagag 1321 aaaaaaaaaa tagtatttgc ataaccctga gcggtggggg aggagggttg tgctacagat 1381 gatagaggat tttatacccc aataatcaac tcgtttttat attaatgtac ttgtttctct 1441 gttgtaagaa taggcattaa cacaaaggag gcgtctcggg agaggattag gttccatcct 1501 ttacgtgttt aaaaaaaagc ataaaaacat tttaaaaaca tagaaaaatt cagcaaacca 1561 tttttaaagt agaagagggt tttaggtaga aaaacatatt cttgtgcttt tcctgataaa 1621 gcacagctgt agtggggttc taggcatctc tgtactttgc ttgctcatat gcatgtagtc 1681 actttataag tcattgtatg ttattatatt ccgtaggtag atgtgtaacc tcttcacctt 1741 attcatggct gaagtcacct cttggttaca gtagcgtagc gtgcccgtgt gcatgtcctt -continued

```
1801  tgcgcctgtg accaccaccc caacaaacca tccagtgaca aaccatccag tggaggtttg
1861  tcgggcacca gccagcgtag cagggtcggg aaaggccacc tgtcccactc ctacgatacg
1921  ctactataaa gagaagacga aatagtgaca taatatattc tatttttata ctcttcctat
1981  ttttgtagtg acctgtttat gagatgctgg ttttctaccc aacggccctg cagccagctc
2041  acgtccaggt tcaacccaca gctacttggt ttgtgttctt cttcatattc taaaaccatt
2101  ccatttccaa gcactttcag tccaataggt gtaggaaata gcgctgtttt tgttgtgtgt
2161  gcagggaggg cagttttcta atggaatggt ttgggaatat ccatgtactt gtttgcaagc
2221  aggactttga ggcaagtgtg ggccactgtg gtggcagtgg aggtggggtg tttgggaggc
2281  tgcgtgccag tcaagaagaa aaaggtttgc attctcacat tgccaggatg ataagttcct
2341  ttccatttct ttaaagaagt tgaagtttag gaatcctttg gtgccaactg gtgtttgaaa
2401  gtagggacct cagaggttta cctagagaac aggtggtttt taagggttat cttagatgtt
2461  tcacaccgga aggtttttaa acactaaaat atataattta tagttaaggc taaaaagtat
2521  atttattgca gaggatgttc ataaggccag tatgatttat aaatgcaatc tccccttgat
2581  ttaaacacac agatacacac acacacacac acacacacaa accttctgcc tttgatgtta
2641  cagatttaat acagtttatt tttaaagata gatcctttta taggtgagaa aaaaacaatc
2701  tggaagaaaa aaaccacaca aagacattga ttcagcctgt ttggcgtttc ccagagtcat
2761  ctgattggac aggcatgggt gcaaggaaaa ttagggtact caacctaagt tcggttccga
2821  tgaattctta tcccctgccc cttcctttaa aaaacttagt gacaaaatag acaatttgca
2881  catcttggct atgtaattct tgtaattttt atttaggaag tgttgaaggg aggtggcaag
2941  agtgtggagg ctgacgtgtg agggaggaca ggcgggagga ggtgtgagga ggaggctccc
3001  gaggggaagg ggcggtgccc acaccgggga caggccgcag ctccattttc ttattgcgct
3061  gctaccgttg acttccaggc acggtttgga aatattcaca tcgcttctgt gtatctcttt
3121  cacattgttt gctgctattg gaggatcagt tttttgtttt acaatgtcat atactgccat
3181  gtactagttt tagttttctc ttagaacatt gtattacaga tgcctttttt gtagtttttt
3241  tttttttat gtgatcaatt ttgacttaat gtgattactg ctctattcca aaaaggttgc
3301  tgtttcacaa tacctcatgc ttcacttagc catggtggac ccagcgggca ggttctgcct
3361  gctttggcgg gcagacacgc gggcgcgatc ccacacaggc tggcgggggc cggccccgag
3421  gccgcgtgcg tgagaaccgc gccggtgtcc ccagagacca ggctgtgtcc ctcttctctt
3481  ccctgcgcct gtgatgctgg gcacttcatc tgatcggggg cgtagcatca tagtagtttt
3541  tacagctgtg ttattctttg cgtgtagcta tggaagttgc ataattatta ttattattat
3601  tataacaagt gtgtcttacg tgccaccacg gcgttgtacc tgtaggactc tcattcggga
3661  tgattggaat agcttctgga atttgttcaa gttttgggta tgtttaatct gttatgtact
3721  agtgttctgt ttgttattgt tttgttaatt acaccataat gctaatttaa agagactcca
3781  aatctcaatg aagccagctc acagtgctgt gtgccccggt cacctagcaa gctgccgaac
3841  caaaagaatt tgcaccccgc tgcgggccca cgtggttggg gccctgccct ggcagggtca
3901  tcctgtgctc ggaggccatc tcgggcacag gcccaccccg ccccacccct ccagaacacg
3961  gctcacgctt acctcaacca tcctggctgc ggcgtctgtc tgaaccacgc gggggccttg
4021  agggacgctt tgtctgtcgt gatggggcaa gggcacaagt cctggatgtt gtgtgtatcg
4081  agaggccaaa ggctggtggc aagtgcacgg ggcacagcgg agtctgtcct gtgacgcgca
4141  agtctgaggg tctgggcggc gggcggctgg gtctgtgcat ttctggttgc accgcggcgc
```

-continued 4201 ttcccagcac caacatgtaa ccggcatgtt tccagcagaa gacaaaaaga caaacatgaa 4261 agtctagaaa taaaactggt aaaaccccaa aaaaaaaaaa aaaa Human CCND1
Amino Acid Sequence

SEQ. ID. NO. 16

MEHQLLCCEVETIRRAYPDANLLNDRVLRAMLKAEETCAPSVSYFKCVQKEVLPS

MRKIVATWMLEVCEEQKCEEEVFPLAMNYLDRFLSLEPVKKSRLQLLGATCMFV

ASKMKETIPLTAEKLCIYTDNSIRPEELLQMELLLVNKLKWNLAAMTPHDFIEHFL

SKMPEAEENKQIIRKHAQTFVALCATDVKFISNPPSMVAAGSVVAAVQGLNLRSP

NNFLSYYRLTRFLSRVIKCDPDCLRACQEQIEALLESSLRQAQQNMDPKAAEEEEE

EEEEVDLACTPTDVRDVDI

Mouse CDK4
mRNA: NM_009870

SEQ. ID. NO. 17

1 gtgggggtga gggggcctct ctagctcgcg gcctgtgtct atggtctggc ccgaagcgtc 61 cagctgcccg ggaccgatcc ccggtgtatg gcgccgcagg aaccggctcc cggcccaga 121 taaagggcca cctccagagc tcttagccga gcgtaagatc ccctgcttcg agaatggctg 181 ccactcgata tgaacccgtg gctgaaattg gtgtcggtgc ctatgggacg gtgtacaaag 241 cccgagatcc ccacagtggc cactttgtgg ccctcaagag tgtgagagtt cctaatggag 301 gagcagctgg agggggcctt cccgtcagca cagttcgtga ggtggccttg ttaaggaggc 361 tggaggcctt tgaacatccc aatgttgtac ggctgatgga tgtctgtgct acttcccgaa 421 ctgatcggga catcaaggtc accctagtgt ttgagcatat agaccaggac ctgaggacat 481 acctggacaa agcacctcca ccgggcctgc cggttgagac cattaaggat ctaatgcgtc 541 agtttctaag cggcctggat ttcttcatg caaactgcat tgttcaccgg gacctgaagc 601 cagagaacat tctagtgaca agtaatggga ccgtcaagct ggctgacttt ggcctagcta 661 gaatctacag ctaccagatg gccctcacgc ctgtggtggt tacgctctgg taccgagctc 721 ctgaagttct tctgcagtct acatacgcaa cacccgtgga catgtggagc gttggctgta 781 tctttgcaga gatgttccgt cggaagcctc tcttctgtgg aaactctgaa gccgaccagt 841 tggggaaaat ctttgatctc attggattgc ctccagaaga cgactggcct cgagaggtat 901 ctctacctcg aggagccttt gcccccagag ggcctcggcc agtgcagtca gtggtgccag 961 agatggagga gtctggagcg cagctgctac tggaaatgct gacctttaac ccacataagc 1021 gaatctctgc cttccgagcc ctgcagcact cctacctgca caaggaggaa agcgacgcag 1081 agtgagaaga ggggctgcct ttcccagtct tggtggagaa accctcgctg aagcggcagc 1141 ctctgtttcc ccccaaggct gtggagaatc ctccagtttt ttacagagaa tattttaagc 1201 cttaaataac aagtccccac ctctccttac gaggttcacc cccattaccc tcccctagct 1261 ctacactaaa gggcaggtgt atctgtcttc ttccctccct gatttatact gggatctttt 1321 ttatacagga aaacaagaca agacaaaaaa aaaaaaaaaa aaaaa Mouse CDK4
Amino Acid Sequence

SEQ. ID. NO. 18

MAATRYEPVAEIGVGAYGTVYKARDPHSGHFVALKSVRVPNGGAAGGGLPVST

VREVALLRRLEAFEHPNVVRLMDVCATSRTDRDIKVTLVFEHIDQDLRTYLDKAP

PPGLPVETIKDLMRQFLSGLDFLHANCIVHRDLKPENILVTSNGTVKLADFGLARI

YSYQMALTPVVVTLWYRAPEVLLQSTYATPVDMWSVGCIFAEMFRRKPLFCGNS

-continued

EADQLGKIFDLIGLPPEDDWPREVSLPRGAFAPRGPRPVQSVVPEMEESGAQLLLE

MLTFNPHKRISAFRALQHSYLHKEESDAE

Mouse CCDN1
mRNA: NM_007631.2

SEQ. ID. NO. 19

```
   1  ttttctctgc ccggctttga tctctgctta acaacagtaa cgtcacacgg actacagggg
  61  agttttgttg aagttgcaaa gtcctgcagc ctccagaggg ctgtcggcgc agtagcagag
 121  agctacagac tccgcgcgct ccggagaccg gcagtacagc gcgaggcagc gcgcgtcagc
 181  agccgccacc ggagcccaac cgagaccaca gccctcccca gacggccgcg ccatggaaca
 241  ccagctcctg tgctgcgaag tggagaccat ccgccgcgcg taccctgaca ccaatctcct
 301  caacgaccgg gtgctgcgag ccatgctcaa gacggaggag acctgtgcgc cctccgtatc
 361  ttacttcaag tgcgtgcaga aggagattgt gccatccatg cggaaaatcg tggccacctg
 421  gatgctggag gtctgtgagg agcagaagtg cgaagaggag gtcttcccgc tggccatgaa
 481  ctacctggac cgcttcctgt ccctggagcc cttgaagaag agccgcctgc agctgctggg
 541  ggccacctgc atgttcgtgg cctctaagat gaaggagacc attcccttga ctgccgagaa
 601  gttgtgcatc tacactgaca actctatccg gcccgaggag ctgctgcaaa tggaactgct
 661  tctggtgaac aagctcaagt ggaacctggc cgccatgact ccccacgatt tcatcgaaca
 721  cttcctctcc aaaatgccag aggcggatga gaacaagcag accatccgca agcatgcaca
 781  gacctttgtg gccctctgtg ccacagatgt gaagttcatt tccaacccac cctccatggt
 841  agctgctggg agcgtggtgg ctgcgatgca aggcctgaac ctgggcagcc ccaacaactt
 901  cctctcctgc taccgcacaa cgcactttct ttccagagtc atcaagtgtg acccggactg
 961  cctccgtgcc tgccaggaac agattgaagc ccttctggag tcaagcctgc gccaggccca
1021  gcagaacgtc gaccccaagg ccactgagga ggagggggaa gtggaggaag aggctggtct
1081  ggcctgcacg cccaccgacg tgcgagatgt ggacatctga gggccaccgg gcaggcggga
1141  gccaccaagt agtggcaccc gcaaagagga aggagccagc ccgggtgctc ctgacgacgt
1201  ccccccttggg gacatgttgt taccagaaga ggaagttttg ttctctttgt tggttgtttt
1261  tccttaatct ttctcctttc tatctgattt aagcaaaaga gaaaaaaata tctgaaagct
1321  gtcttaaaga gagagagaga gagatagaat ctgcatcacc ctgagagtag ggagccaggg
1381  ggtgctacaa aaatagaatt ctgtacccca gtaatcaact agttttctat taatgtgctt
1441  gtctgttcta agagtaggat taacacaggg gaagtcttga gaaggagttt tgattctttt
1501  atatgttttt aaaaaaaagc ttaagaaaca ttgctttaaa aaggaaggaa aaaaaataca
1561  gcaaaccatt gttaaagtag aagagttttt aggttgagaa atgtactctg ctttgctgaa
1621  aagccacagc ttaggccctc agcctcactc cctggcttgc tcagtgccta cagccctgtt
1681  acctgatacc tgtgctttat cccaggggtg ggcagacctc ttaaccttat agatggtcag
1741  tgcgacctct agtggtctca tggcgtgtgg cacaaccccc ctcccccaggg ctcagcttaa
1801  tgtgccctct ccccccaaca acctgcaggt tcacagcacc agccacacag cggtagggat
1861  gaaatagtga cataatatat tctatttttg taaccttcct attttgtagc tctgtttaga
1921  gagatgctgg tttttgcctg aaggccctgc agcctgccca catcaggtta aacccacagc
1981  ttttgtgtgt ggtttgtttt gttgtgtttt ctttctctat gttccaaaac cattccattt
2041  caaagcactt ttggtcagct agctggaggc agtgttgctg gtgtgtgttg gggggagggg
2101  ttctaatgga atggatgggg atgtccacac acgcattcag atggctgtac aacaggttgt
```

-continued

```
2161    agggctggta gtatgaggtg cttgggaagt tttgttgggt caagaagaga gaactctgtt

2221    ctcgcaccac cgggatctgt cctgcaaagt tgaagggatc ctttggtgcc agctggtgtt

2281    tggaagtagg aaccatgatg gcattacctg gacaaggaga ttggggacaa ctcttaagtc

2341    tcacacagga ggcttttaaa cactaaaatg tctaatttat acttaaggct acagaagagt

2401    atttatggga aaggctgccc atgaccagtg tgactcaaag caatgtgatc tcccttgatt

2461    caaacgcaca cctctgccct gctggagaag gtttagggcc atgtctgaga gattggtctt

2521    tcattgggca acgggggggg ggggggggtc cttaaaaaaa aaaaaccaca aagacagaga

2581    tttggtctgc ttgactttcc caacccaatt ggccccattg gagagccatc caaactgagg

2641    aaaattaggg gactccaaaa gagtttgatt ctggcacatt cttgccgctg cccccaagtt

2701    aacaacagta ggtaatttgc acacctctgg ctctgtgcct ttctattagg actttttggc

2761    agaaggtgga gagcgggagg cttaagaggg gatgtgaggg aagaggtgaa ggtgggacca

2821    catgggacag gccacggctc ctctcatggc gctgctaccg atgactccca ggatcccaga

2881    cgttcagaac cagattctca ttgctttgta tctttcacgt tgttttcgct gctattggag

2941    ggtcagtttt gattgttttt gttttacaat gtcagactgc catgttcaag ttttaatttc

3001    ctcatagagt gtatttacag atgccctttt ttgtactttt ttttttaatt gtgatctatt

3061    ttggcttaat gtgattaccg ctgtattcca aaaaaaaaaa aaaaacaggt tcctgttcac

3121    aatacctcat gtatcatcta gccatgcacg agcctggcag gcaggtgggc ggtctgcctc

3181    cagggatcct gggaccctga tggcgatcgt cctgtcatgc tgggcccttc atttgatctg

3241    ggacatagca tcacagcagt cagggcacct ggattgttct gttatcgata ttgtttcttg

3301    tagcggcctg ttgtgcatgc caccatgctg ctggcccggg gggatttgct ctgagtctcc

3361    ggtgcatcat ttaatctgtt aggttctagt gttccgtctt gttttgtgtt aattacagca

3421    ttgtgctaat gtaaagactc tgcctttgcg aagccagctg cagtgctgta ggcccccaag

3481    ttccctagca agctgccaaa ccaaaacggg caccaccagc tcagctgagg catcccagcc

3541    aggcaggacc cttgagggcc gctgtatcca tggtgatggg gtgaggtttt ggccaaaagg

3601    ccaaagactg gtggtgggtc cacggaatct gccctgtgac atgaaaggct ttgaggggct

3661    ctggctggtg gccaggttgg ctttttgtat ttctggttga cacaccatgg cgcttcccag

3721    cacagacatg tgaccagcat ggtccaggaa aaaaaaaaag acaaaaaatc tagaaaataa

3781    aattggtaaa atctca
```

Mouse CCND1
Amino Acid Sequence

SEQ. ID. NO. 20

```
MEHQLLCCEVETIRRAYPDTNLLNDRVLRAMLKTEETCAPSVSYFKCVQKEIVPS
MRKIVATWMLEVCEEQKCEEEVFPLAMNYLDRFLSLEPLKKSRLQLLGATCMFV
ASKMKETIPLTAEKLCIYTDNSIRPEELLQMELLLVNKLKWNLAAMTPHDFIEHFL
SKMPEADENKQTIRKHAQTFVALCATDVKFISNPPSMVAAGSVVAAMQGLNLGS
PNNFLSCYRTTHFLSRVIKCDPDCLRACQEQIEALLESSLRQAQQNVDPKATEEEG
EVEEEAGLACTPTDVRDVDI
```

What is claimed is:

1. A method of inducing proliferation and/or cell cycle reentry of an adult postmitotic cell, the method comprising contacting the adult postmitotic cell with an effective amount of a composition comprising cyclin-dependent kinase-1 (CDK1), cyclinB, CDK4, and cyclinD, or equivalents of each thereof, thereby inducing proliferation and/or cell cycle reentry of the adult postmitotic cell.

2. The method of claim 1, further comprising contacting the cell with an effective amount of a CDK activator, a transforming growth factor β inhibitor, or combinations thereof.

3. The method of claim 2, wherein the CDK activator is a CDK1 activator.

4. The method of claim 1, wherein the adult postmitotic cell is selected from the group consisting of a cardiomyocyte, a neural cell, a pancreatic cell, a hair cell, and a skeletal muscle cell.

5. The method of claim 1, wherein the cyclin-dependent kinase-1 (CDK1), cyclinB, CDK4, and cyclinD encoded by at least one heterologous nucleic acid.

6. The method of claim 5, wherein the at least one nucleic acid is a modified mRNA.

7. The method of claim 6, wherein the at least one nucleic acid is constitutively expressed.

8. The method of claim 1, wherein the cyclinB is cyclinB1 (CCNB1), and/or the cyclinD is cyclinD1 (CCND1).

9. The method of claim 1, wherein the CDK1 and/or CDK4 is constitutively expressed.

* * * * *

UNITED STATES PATENT AND TRADEMARK OFFICE

CERTIFICATE OF CORRECTION

PATENT NO. : 10,669,596 B2
APPLICATION NO. : 15/564752
DATED : June 2, 2020
INVENTOR(S) : Mohamed et al.

It is certified that error appears in the above-identified patent and that said Letters Patent is hereby corrected as shown below:

In the Claims

In Column 110, Line 17, in Claim 7, delete “claim 6,” and insert --claim 5,-- therefor Signed and Sealed this
Twenty-second Day of December, 2020

Andrei Iancu
*Director of the United States Patent and Trademark Office*